United States Patent
Bajpayee et al.

(10) Patent No.: US 10,226,427 B2
(45) Date of Patent: Mar. 12, 2019

(54) SURFACE BINDING OF NANOPARTICLE BASED DRUG DELIVERY TO TISSUE

(71) Applicant: Massachusetts Institute of Technology, Cambridge, MA (US)

(72) Inventors: Ambika Goel Bajpayee, Cambridge, MA (US); Alan Grodzinsky, Lexington, MA (US); Cliff Richard Wong, Cambridge, MA (US); Moungi G. Bawendi, Cambridge, MA (US); Rohit N. Karnik, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/071,709

(22) Filed: Mar. 16, 2016

(65) Prior Publication Data

US 2016/0296471 A1    Oct. 13, 2016

Related U.S. Application Data

(62) Division of application No. 14/147,863, filed on Jan. 6, 2014, now Pat. No. 9,289,506.

(60) Provisional application No. 61/870,288, filed on Aug. 27, 2013, provisional application No. 61/748,809, filed on Jan. 4, 2013.

(51) Int. Cl.
| | |
|---|---|
| A61K 9/00 | (2006.01) |
| A61K 31/573 | (2006.01) |
| A61K 38/17 | (2006.01) |
| A61K 38/30 | (2006.01) |
| A61K 9/51 | (2006.01) |
| A61P 19/02 | (2006.01) |
| A61P 19/04 | (2006.01) |
| A61P 19/10 | (2006.01) |
| A61P 21/06 | (2006.01) |
| B82Y 5/00 | (2011.01) |
| A61K 9/16 | (2006.01) |
| A61K 38/18 | (2006.01) |
| A61K 47/60 | (2017.01) |
| A61K 47/55 | (2017.01) |
| A61K 47/64 | (2017.01) |

(52) U.S. Cl.
CPC ............ *A61K 9/167* (2013.01); *A61K 9/0019* (2013.01); *A61K 31/573* (2013.01); *A61K 38/18* (2013.01); *A61K 47/551* (2017.08); *A61K 47/60* (2017.08); *A61K 47/64* (2017.08); *A61K 47/645* (2017.08)

(58) Field of Classification Search
None
See application file for complete search history.

(56) References Cited

U.S. PATENT DOCUMENTS

| 5,908,626 A | 6/1999 | Chang et al. |
|---|---|---|
| 6,958,148 B1 | 10/2005 | Green et al. |
| 7,807,133 B2 | 10/2010 | Rita et al. |
| 8,562,947 B2 | 10/2013 | De Santis et al. |
| 2005/0177118 A1 | 8/2005 | Hoganson et al. |
| 2006/0084794 A1 | 4/2006 | Rosen et al. |
| 2006/0204941 A1 | 9/2006 | Kogo |
| 2007/0269382 A1 | 11/2007 | Santra et al. |
| 2009/0238762 A1 | 9/2009 | Totoritis et al. |
| 2009/0324678 A1 | 12/2009 | Thorne et al. |
| 2010/0015068 A1 | 1/2010 | Karp et al. |
| 2010/0239497 A1 | 9/2010 | DeSantis et al. |
| 2011/0104052 A1 | 5/2011 | Barnett et al. |
| 2012/0015037 A1 | 1/2012 | Hsieh et al. |
| 2012/0156135 A1 | 6/2012 | Farokhzad et al. |
| 2014/0134106 A1 | 5/2014 | De Santis |

FOREIGN PATENT DOCUMENTS

| JP | 2006-526994 | 11/2006 |
|---|---|---|
| JP | 2009-292787 | 12/2009 |
| JP | 2010-505444 | 2/2010 |
| WO | WO 1991/003553 A1 | 3/1991 |
| WO | WO 2004/022718 A2 | 3/2004 |
| WO | WO 2004/111648 A2 | 12/2004 |
| WO | WO 2005/072893 A1 | 8/2005 |
| WO | WO 2008/063291 A2 | 5/2008 |
| WO | WO 2008/144753 A2 | 11/2008 |

OTHER PUBLICATIONS

Genbank NCBI Submission; Gene: ALB albumin. Apr. 14, 2015.
Abramson et al., Biologics in development for rheumatoid arthritis: relevance to osteoarthritis. Adv Drug Deliv Rev. May 20, 2006;58(2):212-25. Epub Feb. 28, 2006.
Abramson, Drug delivery in degenerative joint disease: where we are and where to go? Adv Drug Deliv Rev. May 20, 2006;58(2):125-7. Epub May 2, 2006.
Aigner et al., Drug delivery in degenerative joint disease. Adv Drug Deliv Rev. May 20, 2006;58(2):123-4. Epub Mar. 24, 2006.
Anderson et al., Post-traumatic osteoarthritis: improved understanding and opportunities for early intervention. J Orthop Res. Jun. 2011;29(6):802-9. doi: 10.1002/jor.21359. Epub Feb. 11, 2011.
Bajpayee et al., Avidin as a model for charge driven transport into cartilage and drug delivery for treating early stage post-traumatic osteoarthritis. Biomaterials. Jan. 2014;35(1):538-49. doi: 10.1016/j.biomaterials.2013.09.091. Epub Oct. 10, 2013.
Bendele, Animal models of osteoarthritis. J Musculoskelet Neuronal Interact. Jun. 2001;1(4):363-76.
Bohme et al., Effective charge of bovine serum albumin determined by electrophoresis NMR. Chemical Physics Letters. 2007; 435:342-5. Epub Dec. 28, 2006.
Bonassar et al., Changes in cartilage composition and physical properties due to stromelysin degradation. Arthritis Rheum. Feb. 1995;38(2):173-83.

(Continued)

*Primary Examiner* — Julie Ha
*Assistant Examiner* — Kristina M Hellman
(74) *Attorney, Agent, or Firm* — Wolf, Greenfield & Sacks, P.C.

(57) ABSTRACT

Microparticles and nanoparticles and compositions thereof are provided. The microparticles and nanoparticles and compositions may be used for the treatment of musculoskeletal disease, such as osteoarthritis and injury such as trauma.

8 Claims, 27 Drawing Sheets
Specification includes a Sequence Listing.

(56) References Cited

OTHER PUBLICATIONS

Burt et al., Intra-articular drug delivery systems: Overcoming the shortcomings of joint disease therapy. Expert Opin Drug Deliv. Jan. 2009;6(1):17-26. doi: 10.1517/17425240802647259.
Butoescu et al., Dexamethasone-containing PLGA superparamagnetic microparticles as carriers for the local treatment of arthritis. Biomaterials. Mar. 2009;30(9):1772-80. doi: 10.1016/j.biomaterials.2008.12.017. Epub Jan. 8, 2009.
Byun et al., Transport and equilibrium uptake of a peptide inhibitor of PACE4 into articular cartilage is dominated by electrostatic interactions. Arch Biochem Biophys. Jul. 2010;499(1-2):32-9. doi: 10.1016/j.abb.2010.04.019. Epub May 4, 2010.
Day et al., Pharmacokinetics of nonsteroidal anti-inflammatory drugs in synovial fluid. Clin Pharmacokinet. Mar. 1999;36(3):191-210.
Ellison et al., Limited proteolysis of native proteins: the interaction between avidin and proteinase K. Protein Sci. Jul. 1995;4(7):1337-45.
Elsaid et al., Pharmaceutical nanocarrier association with chondrocytes and cartilage explants: influence of surface modification and extracellular matrix depletion. Osteoarthritis Cartilage. Feb. 2013;21(2):377-84. doi: 10.1016/j.joca.2012.11.011. Epub Nov. 24, 2012.
Evans et al., Progress in intra-articular therapy. Nat Rev Rheumatol. Jan. 2014;10(1):11-22. doi: 10.1038/nrrheum.2013.159. Epub Nov. 5, 2013.
Figge, Figge-Fencl Quantitative Physicochemical Model of Human Acid-Base Physiology (Version 3.0) Oct. 8, 2012. http://www.figge-fencl.org/titrationcurve.html [last accessed May 19, 2015].
Gabrilovich et al., Production of vascular endothelial growth factor by human tumors inhibits the functional maturation of dendritic cells. Nat Med. Oct. 1996;2(10):1096-103. Erratum in: Nat Med Nov. 1996;2(11):1267.
Gardner, Potential and limitations of drug targeting: an overview. Biomaterials. May 1985;6(3):153-60.
Gerwin et al., Intraarticular drug delivery in osteoarthritis. Adv Drug Deliv Rev. May 20, 2006;58(2):226-42. Epub Feb. 23, 2006.
Goldberg et al., Nanostructured materials for applications in drug delivery and tissue engineering. J Biomater Sci Polym Ed. 2007;18(3):241-68.
Greene et al., Changes in pore morphology and fluid transport in compressed articular cartilage and the implications for joint lubrication. Biomaterials. Nov. 2008;29(33):4455-62. doi: 10.1016/j.biomaterials.2008.07.046. Epub Aug. 27, 2008.
Horisawa et al., Size-dependency of DL-lactide/glycolide copolymer particulates for intra-articular delivery system on phagocytosis in rat synovium. Pharm Res. Feb. 2002;19(2):132-9.
Hunter, Pharmacologic therapy for osteoarthritis—the era of disease modification. Nat Rev Rheumatol. Jan. 2011;7(1):13-22. doi: 10.1038/nrrheum.2010.178. Epub Nov. 16, 2010.
Kraus et al., Effects of intraarticular IL1-Ra for acute anterior cruciate ligament knee injury: a randomized controlled pilot trial (NCT00332254). Osteoarthritis Cartilage. Apr. 2012;20(4):271-8. doi: 10.1016/j.joca.2011.12.009. Epub Jan. 10, 2012.
Larsen et al., Intra-articular depot formulation principles: role in the management of postoperative pain and arthritic disorders. J Pharm Sci. Nov. 2008;97(11):4622-54. doi: 10.1002/jps.21346.
Leddy et al., Molecular diffusion in tissue-engineered cartilage constructs: effects of scaffold material, time, and culture conditions. J Biomed Mater Res B Appl Biomater. Aug. 15, 2004;70(2):397-406.
Li et al., IGF-1 Reduced Matrix Degradation and Enhanced Biosynthesis in IL-1α-Treated Injuriously Compressed Cartilage. 58$^{th}$ Trans Orthopedic Research Society. San Francisco. Feb. 3-7, 2012.
Liotta et al., Preferential digestion of basement membrane collagen by an enzyme derived from a metastatic murine tumor. Proc Natl Acad Sci U S A. May 1979;76(5):2268-72.
Lohmander et al., The long-term consequence of anterior cruciate ligament and meniscus injuries: osteoarthritis. Am J Sports Med. Oct. 2007;35(10):1756-69. Epub Aug. 29, 2007.

Lotz et al., New developments in osteoarthritis. Posttraumatic osteoarthritis: pathogenesis and pharmacological treatment options. Arthritis Res Ther. 2010;12(3):211. doi: 10.1186/ar3046. Epub Jun. 28, 2010. Review. Erratum in: Arthritis Res Ther. 2010;12(6):408. Kraus, Virginia B [added].
Lu et al., Effects of short-term glucocorticoid treatment on changes in cartilage matrix degradation and chondrocyte gene expression induced by mechanical injury and inflammatory cytokines. Arthritis Res Ther. 2011;13(5):R142. doi: 10.1186/ar3456. Epub Sep. 2, 2011.
Manz et al., Synthesis of biotin-labelled dexamethasone derivatives. Novel hormone-affinity probes. Eur J Biochem. Mar. 15, 1983;131(2):333-8.
Maroudas, Transport of solutes through cartilage: permeability to large molecules. J Anat. Nov. 1976;122(Pt 2):335-47.
Miller et al., Intraarticular injection of heparin-binding insulin-like growth factor 1 sustains delivery of insulin-like growth factor 1 to cartilage through binding to chondroitin sulfate. Arthritis Rheum. Dec. 2010;62(12):3686-94. doi: 10.1002/art.27709.
Moeini et al., Solute adsorption to surfaces of articular cartilage explants: apparent versus actual partition coefficients. Soft Matter. 2012;8:11880-11888.
Ng et al., Individual cartilage aggrecan macromolecules and their constituent glycosaminoglycans visualized via atomic force microscopy. J Struct Biol. Sep. 2003;143(3):242-57.
Patwari et al., Proteoglycan degradation after injurious compression of bovine and human articular cartilage in vitro: interaction with exogenous cytokines. Arthritis Rheum. May 2003;48(5):1292-301.
Qi et al., Emerging application of quantum dots for drug delivery and therapy. Expert Opin Drug Deliv. Mar. 2008;5(3):263-7. doi: 10.1517/17425247.5.3.263.
Roos et al., Osteoarthritis of the knee after injury to the anterior cruciate ligament or meniscus: the influence of time and age. Osteoarthritis Cartilage. Dec. 1995;3(4):261-7.
Rothenfluh et al., Biofunctional polymer nanoparticles for intra-articular targeting and retention in cartilage. Nat Mater. Mar. 2008;7(3):248-54. doi: 10.1038/nmat2116. Epub Feb. 3, 2008.
Snowden et al., The distribution of serum albumin in human normal and degenerate articular cartilage. Biochim Biophys Acta. May 28, 1976;428(3):726-40.
Tokunou et al., Engineering insulin-like growth factor-1 for local delivery. FASEB J. Jun. 2008;22(6):1886-93. doi: 10.1096/fj.07-100925. Epub Feb. 19, 2008.
Torzilli et al., Diffusive properties of immature articular cartilage. J Biomed Mater Res. Apr. 1998;40(1):132-8.
Tunçay et al., In vitro and in vivo evaluation of diclofenac sodium loaded albumin microspheres. J Microencapsul. Mar.-Apr. 2000;17(2):145-55.
Wang et al., In vivo restoration of full-thickness cartilage defects by poly(lactide-co-glycolide) sponges filled with fibrin gel, bone marrow mesenchymal stem cells and DNA complexes. Biomaterials. Aug. 2010;31(23):5953-65. doi: 10.1016/j.biomaterials.2010.04.029. Epub May 21, 2010.
Wieland et al., Osteoarthritis—an untreatable disease? Nat Rev Drug Discov. Apr. 2005;4(4):331-44. Review. Erratum in: Nat Rev Drug Discov. Jul. 2005;4(7):543.
Zhang et al., OARSI recommendations for the management of hip and knee osteoarthritis: part III: Changes in evidence following systematic cumulative update of research published through Jan. 2009. Osteoarthritis Cartilage. Apr. 2010;18(4):476-99. doi: 10.1016/j.joca.2010.01.013. Epub Feb. 11, 2010.
Chen et al., The Effect of Molecular Weight, Drug Load, and Charge of Gelatin-Mtx Conjugates on Growth Inhibition of HL-60 Leukemia Cells. Pharm Res. Oct. 31, 2008;26(2):338-345.
Koo et al., Actively targeted low-dose camptothecin as a safe, long-acting, disease-modifying nanomedicine for rheumatoid arthritis. Pharm Res. Apr. 2011;28(4):776-87. doi: 10.1007/s11095010-0330-4. Epub Dec. 4, 2010.
Koo et al., Camptothecin in sterically stabilized phospholipid micelles: a novel nanomedicine. Nanomedicine. Mar. 2005;1(1):77-84. Erratum in: Nanomedicine. Jun. 2005;1(2):192.

(56) References Cited

OTHER PUBLICATIONS

Morgen et al., Nanoparticles for improved local retention after intra-articular injection into the knee joint. Pharm Res. Jan. 2013;30(1):257-68. doi: 10.1007/s11095-012-0870-x. Epub Sep. 21, 2012.

Wunder et al., Albumin-based drug delivery as novel therapeutic approach for rheumatoid arthritis. J Immunol. May 1, 2003;170(9):4793-801.

FIG. 1A
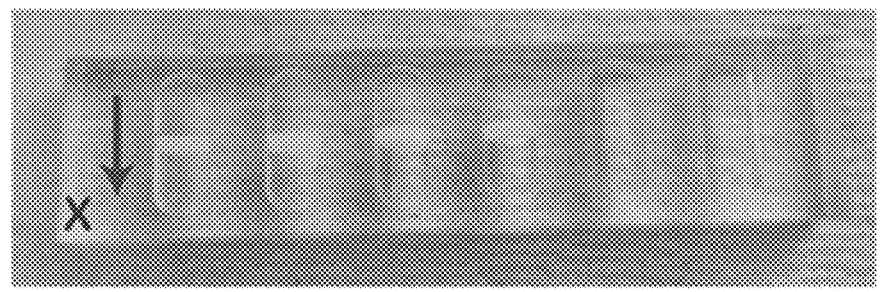
FIG. 1B
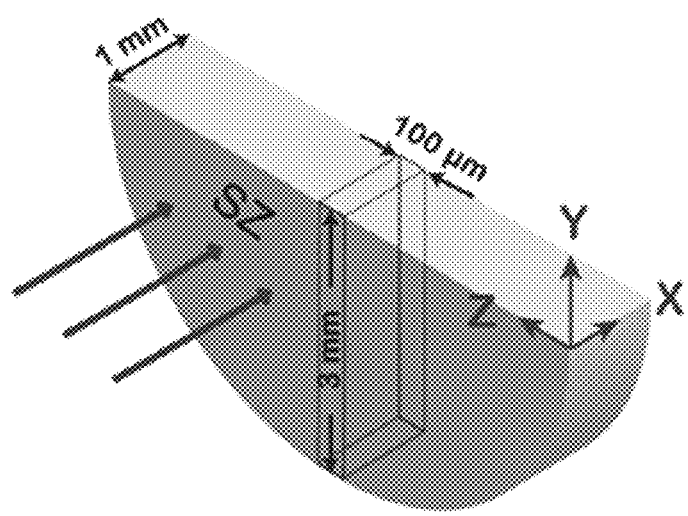
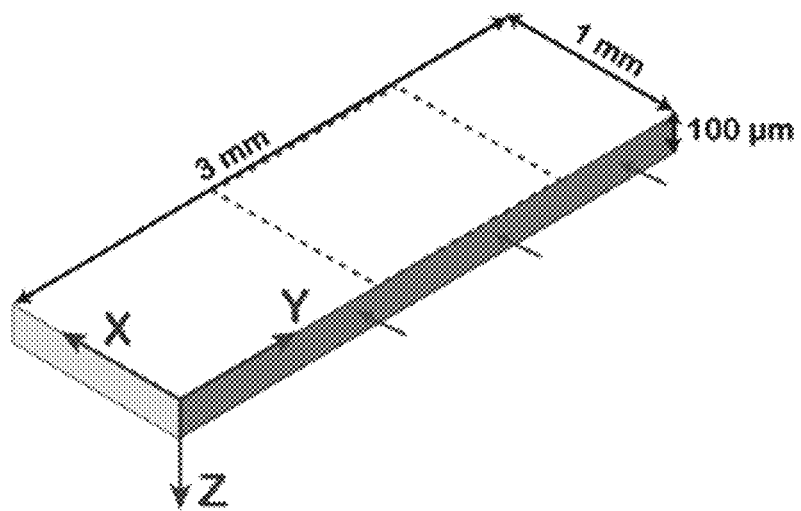

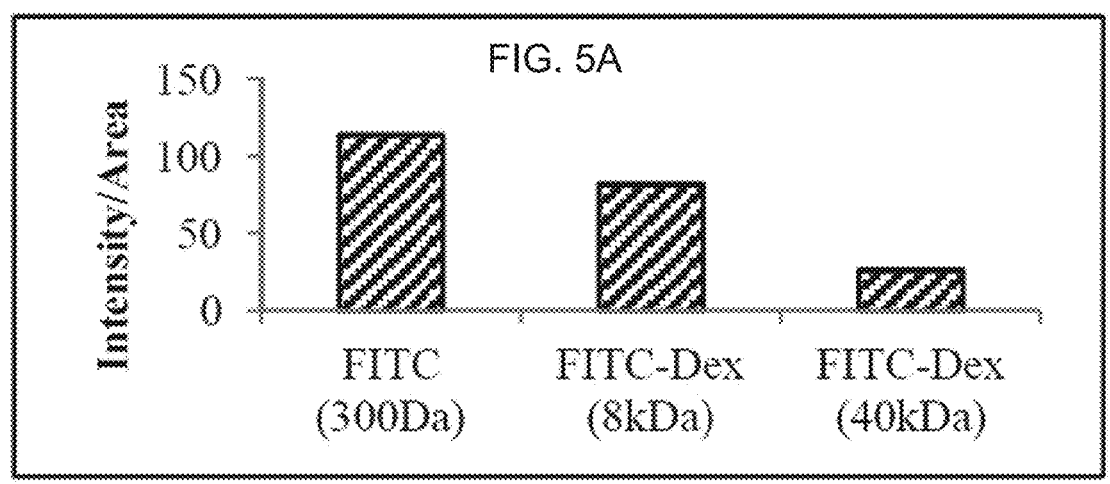
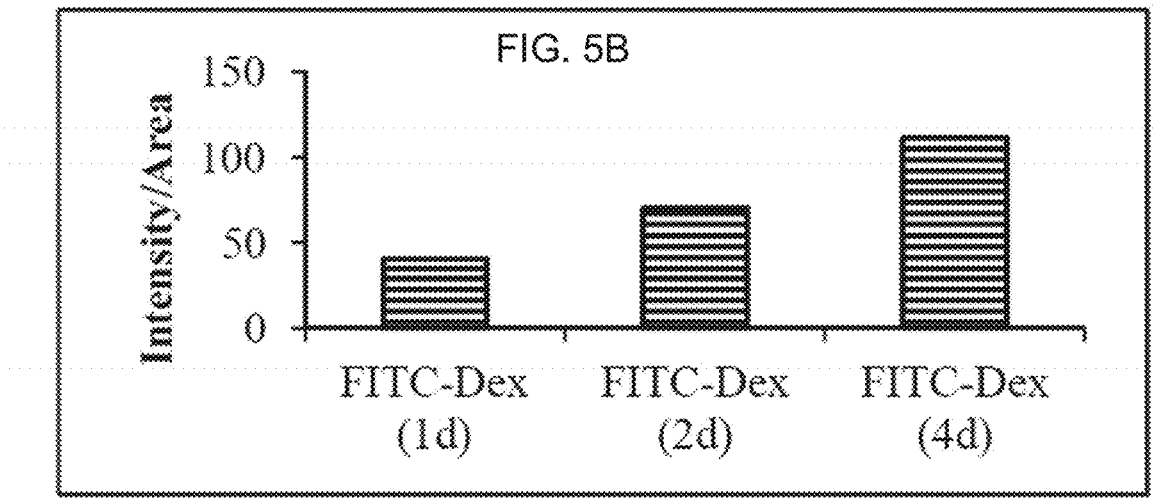

Normal Cartilage
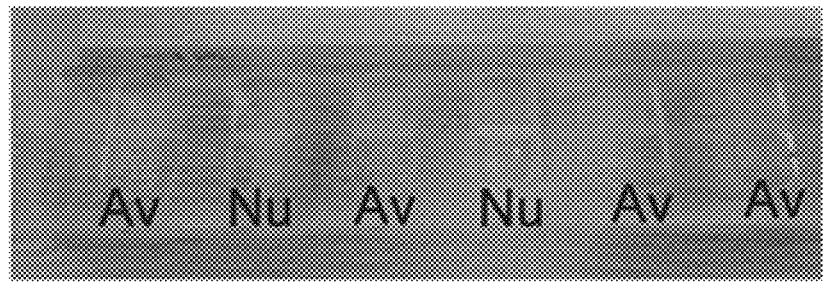
FIG. 11A
FIG. 11B
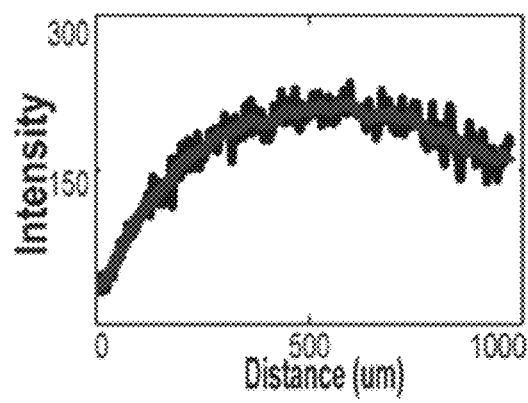
FIG. 11C
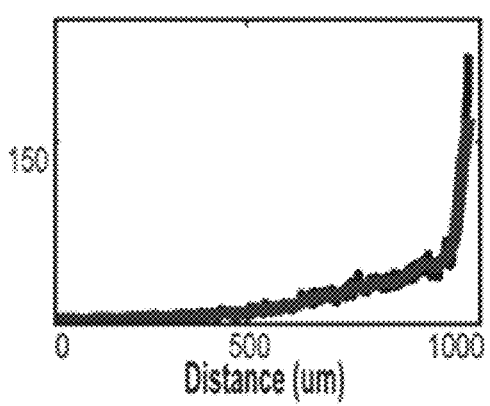
FIG. 11D
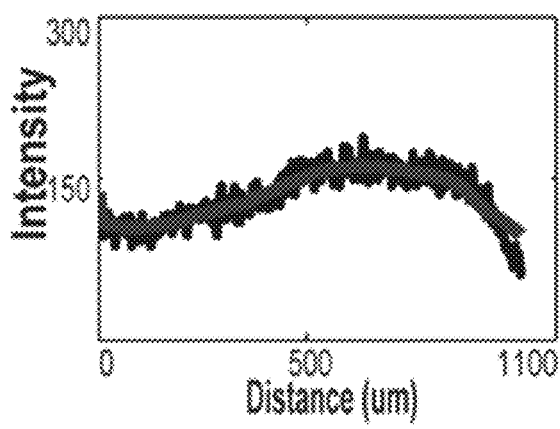
FIG. 11E
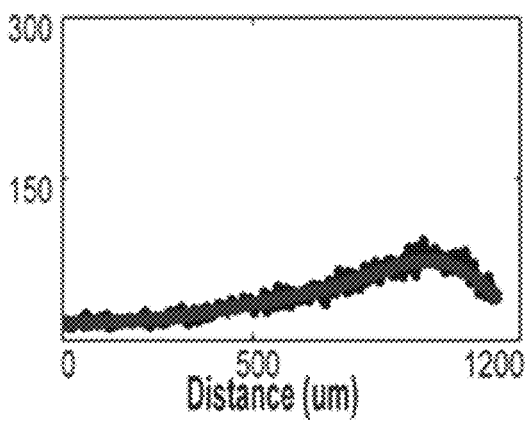

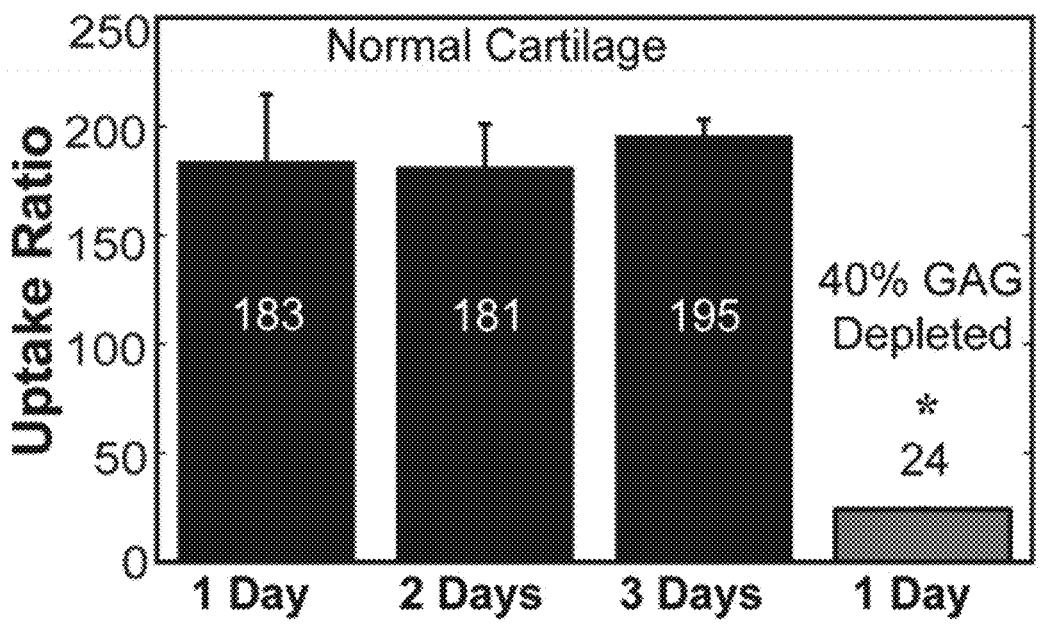
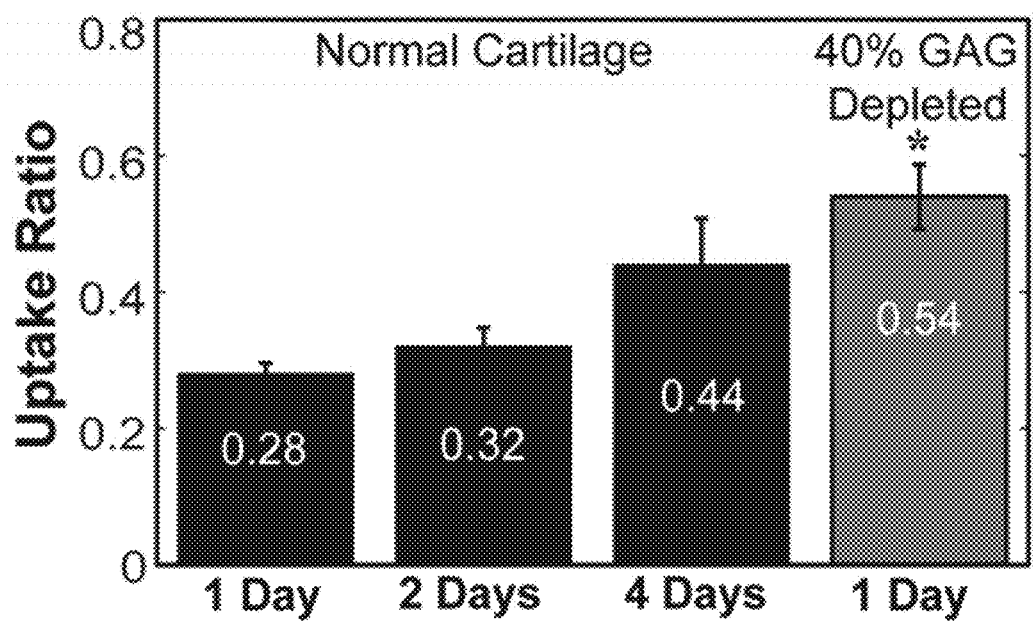

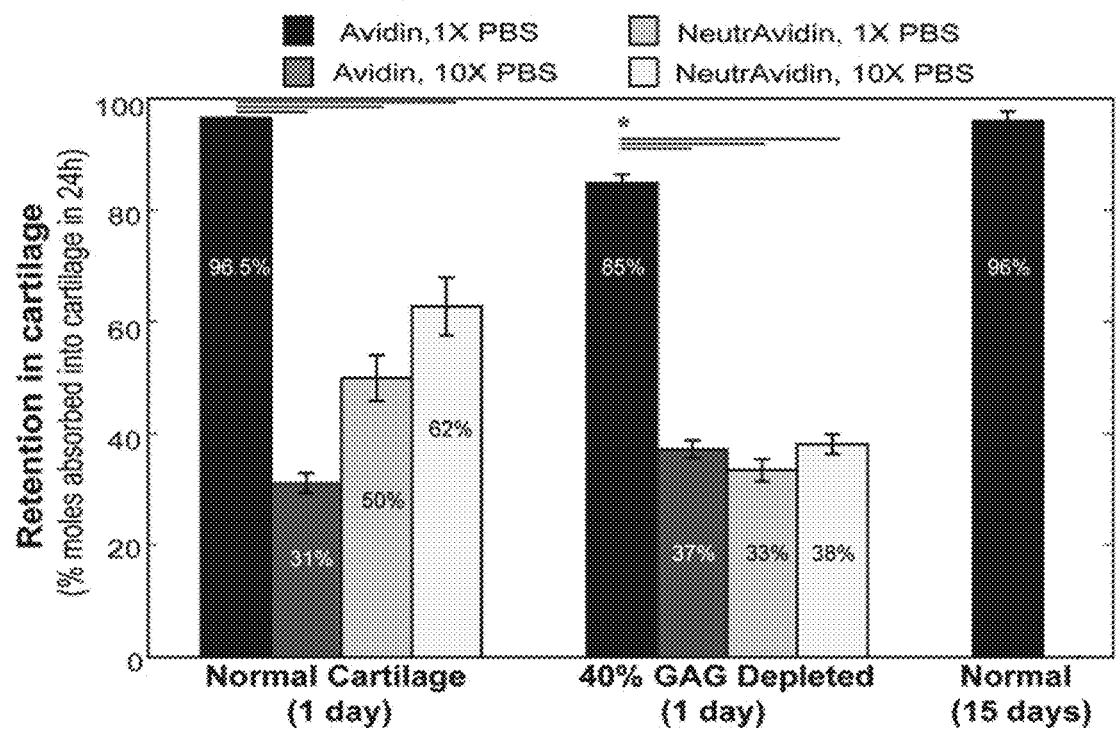

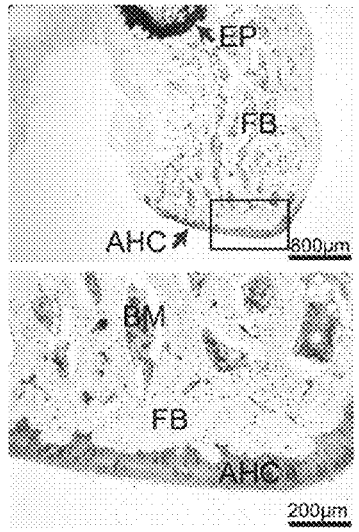
FIG. 19A
FIG. 19B
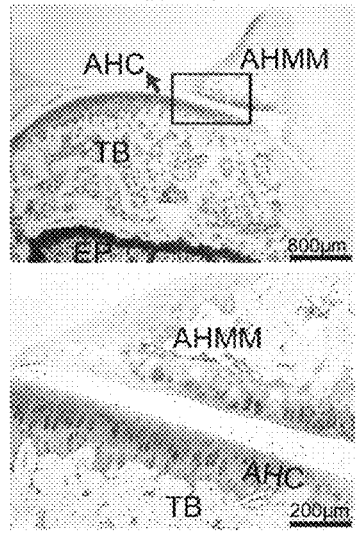
FIG. 19C
FIG. 19D
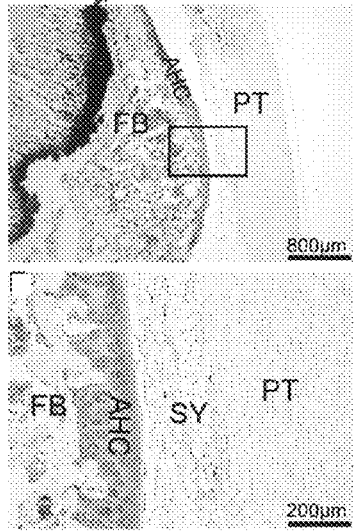
FIG. 19E
FIG. 19F
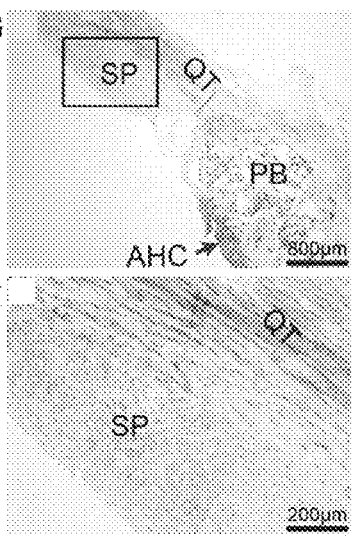
FIG. 19G
FIG. 19H
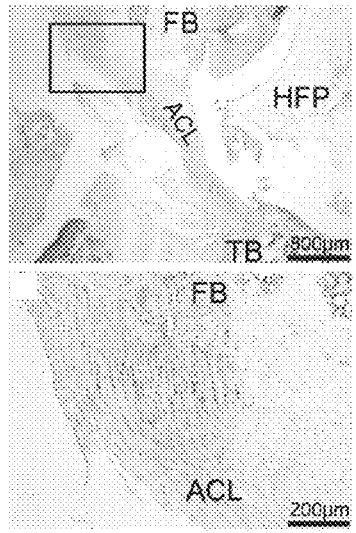
FIG. 19I
FIG. 19J

SEQUENCE LISTING

```
<160> NUMBER OF SEQ ID NOS: 7

<210> SEQ ID NO 1
<211> LENGTH: 152
<212> TYPE: PRT
<213> ORGANISM: Artificial Sequence
<220> FEATURE:
<223> OTHER INFORMATION: Synthetic polypeptide

<400> SEQUENCE: 1

Met Val His Ala Thr Ser Pro Leu Leu Leu Leu Leu Leu Leu Ser Leu
1               5                   10                  15

Ala Leu Val Ala Pro Ser Leu Ser Ala Arg Lys Cys Ser Leu Thr Gly
            20                  25                  30

Lys Trp Thr Asn Asp Leu Gly Ser Asn Met Thr Ile Gly Ala Val Asn
        35                  40                  45

Ser Arg Gly Glu Phe Thr Gly Thr Tyr Ile Thr Ala Val Thr Ala Thr
    50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
    130                 135                 140

Thr Arg Leu Arg Thr Gln Lys Glu
145                 150

<210> SEQ ID NO 2
<211> LENGTH: 17
```

<212> TYPE: PRT
<213> ORGANISM: Artificial Sequence
<220> FEATURE:
<223> OTHER INFORMATION: Synthetic polypeptide

<400> SEQUENCE: 2

Trp Trp Trp Trp Trp His His His His Arg Arg Arg Arg Arg Arg
1               5                   10                  15

Arg

<210> SEQ ID NO 3
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 3

Ile Ile Ile Ile Ile His His His His Arg Arg Arg Arg Arg Arg
1               5                   10                  15

Arg

<210> SEQ ID NO 4
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 4

Phe Phe Phe Phe Phe His His His His Arg Arg Arg Arg Arg Arg
1               5                   10                  15

Arg

<210> SEQ ID NO 5
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 5

Ala Ala Ala Ala Ala Ala Ala Ala Ala Ala Ala Ala His His His His
1               5                   10                  15

Lys Lys Lys Lys Lys Lys Lys Lys Lys Lys
            20                  25

<210> SEQ ID NO 6
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 6

Ala Ala Ala Ala Ala Ala Ala Ala Ala Ala Ala Ala His His His Lys
1               5                   10                  15

Lys Lys Lys Lys Lys Lys Lys Lys Lys Lys Lys Lys Lys Lys
            20                  25                  30

<210> SEQ ID NO 7
<211> LENGTH: 5
<212> TYPE: PRT
<213> ORGANISM: Artificial Sequence

```
<220> FEATURE:
<223> OTHER INFORMATION: Synthetic polypeptide

<400> SEQUENCE: 7

Arg Tyr Lys Arg Thr
1               5
```

SURFACE BINDING OF NANOPARTICLE BASED DRUG DELIVERY TO TISSUE

RELATED APPLICATIONS

This application claims priority under 35 U.S.C. § 119(e) to U.S. Provisional Application Ser. No. 61/870,288, entitled "SURFACE BINDING OF NANOPARTICLE BASED DRUG DELIVERY TO TISSUE" filed on Aug. 27, 2013, which is herein incorporated by reference in its entirety. This application claims priority under 35 U.S.C. § 119(e) to U.S. Provisional Application Ser. No. 61/748,809, entitled "SURFACE BINDING OF NANOPARTICLES-BASED DRUG DELIVERY TO TISSUE" filed on Jan. 4, 2013, which is herein incorporated by reference in its entirety.

FEDERALLY SPONSORED RESEARCH

This invention was made with government support under Grant No. AR060331 awarded by the National Institutes of Health. The government has certain rights in the invention.

FIELD OF THE INVENTION

The invention relates to methods and reagents for particle based drug delivery systems.

BACKGROUND OF INVENTION

Osteoarthritis (OA) attacks the cartilage in human joints, affecting productivity and quality of life, and is extremely disabling to the patient. Osteoarthritis affects over 150 million people worldwide, and yet there is no cure for it available. Current therapies only provide short term pain and inflammation relief but afford no protection against the inevitable further degeneration of joint cartilage, the hallmark of end-stage OA. This results in complete joint dysfunction (including deterioration of bone and other soft tissues), leading to the patient's need for joint replacement.

SUMMARY OF INVENTION

The invention in some aspects is a method for delivering an active agent to a connective tissue in a subject, by administering to a subject, a microparticle or having an average particle size of greater than 10 nm, wherein the microparticle is functionalized with a connective tissue binding compound and includes a first active agent, wherein the active agent is delivered to the connective tissue as it is released from the microparticle. In some embodiments the subject has a musculoskeletal disease or injury.

In some aspects the invention is method for treating musculoskeletal disease, by administering to a subject, a microparticle having an average particle size of greater than 10 nm, wherein the microparticle is functionalized with a connective tissue binding compound and includes a therapeutic agent for the treatment of musculoskeletal disease or injury. In some embodiments the musculoskeletal disease is osteoarthritis. In other embodiments the subject has post traumatic osteoarthritis. In yet other embodiments the subject has late stage osteoarthritis.

The subject may also be administered a nanoparticle having an average particle size of 10 nm or less, wherein the nanoparticle includes a second active agent.

The microparticle or nanoparticle may be constructed from any material used in conventional microparticle technology. For instance the microparticle or nanoparticle may include a polymer, a peptide, such as, for example 5 amino acids or more from the amino acid sequence of SEQ ID NO 1, or combinations thereof.

The first active agent in the microparticle or nanoparticle may be a therapeutic agent for the treatment of osteoarthritis, a therapeutic agent for the treatment of musculoskeletal disease, and/or an analgesic.

In other embodiments the second active agent may be an analgesic, a therapeutic agent for the treatment of osteoarthritis and/or a therapeutic agent for the treatment of musculoskeletal disease or injury.

The microparticle or nanoparticle in some embodiments includes an analgesic and a therapeutic agent for the treatment of osteoarthritis. In other embodiments the nanoparticle includes an analgesic and a therapeutic agent for the treatment of osteoarthritis.

The microparticle and the nanoparticle may be delivered separately to the subject. Alternatively the microparticle and the nanoparticle may be delivered in the same composition to the subject. In other embodiments the microparticle and the nanoparticle are delivered at the same time to the subject.

A composition is provided according to other aspects of the invention. The composition is a microparticle having an average particle size of greater than 10 nm, wherein the microparticle is functionalized with a connective tissue binding compound and includes a first active agent, and a nanoparticle having an average particle size of 10 nm or less, wherein the nanoparticle includes a second active agent.

In other aspects the invention is a microparticle having an average particle size of greater than 10 nm, wherein the microparticle is functionalized with a connective tissue binding compound and includes a therapeutic agent for the treatment of a musculoskeletal disease such as osteoarthritis or injury such as trauma. In some aspects the microparticle is mixed with a nanoparticle having an average particle size of 10 nm or less, wherein the nanoparticle includes a second active agent.

The microparticle or nanoparticle may be constructed from any material used in conventional microparticle technology. For instance the microparticle or nanoparticle may include a polymer, a peptide, such as, for example 5 amino acids or more from the amino acid sequence of SEQ ID NO 1, or combinations thereof.

The first active agent in the microparticle or nanoparticle may be a therapeutic agent for the treatment of osteoarthritis, a therapeutic agent for the treatment of musculoskeletal disease or injury, and/or an analgesic.

In other embodiments the second active agent may be an analgesic, a therapeutic agent for the treatment of osteoarthritis and/or a therapeutic agent for the treatment of musculoskeletal disease or injury.

The microparticle in some embodiments includes an analgesic and a therapeutic agent for the treatment of osteoarthritis. In other embodiments the nanoparticle includes an analgesic and a therapeutic agent for the treatment of osteoarthritis.

In some embodiments the active agent is selected from the group consisting of dexamethasone, Disease Modifying Osteoarthritis Drug (DMOAD), pro-anabolic growth factors including IGF (Insulin like Growth Factors), IGF-1, FGF-15, and BMP7, and anti-catabolic agents including glucocorticoid class of steroid drug such as Triamcinolone, blockers of inflammatory cytokines, inhibitors of TNF, IL-1, Aggrecanases and Matrix Metalloproteinases.

A composition is provided according to other aspects. The composition includes a nanoparticle having an average particle size of 10 nm or less, wherein the nanoparticle includes an active agent, wherein the active agent is a therapeutic agent for the treatment of disease condition of a bone or connective tissue and wherein the nanoparticle comprises a polymer having a net positive charge of greater than 6. In some embodiments the polymer has a molecular weight of less than 90 kd, 10 kd-90 kd, 60-90 kd, 60-80 kd, or 60-70 kd.

The polymer in some embodiments is a peptide. The peptide may be, for instance, 5 amino acids or more from the amino acid sequence of SEQ ID NO 1 or 15 amino acids or more from the amino acid sequence of SEQ ID NO 1.

In some embodiments the nanoparticle comprises a polymer having a net positive charge of 6-20 or a net positive charge of 7-14.

In some embodiments the peptide is selected from the group consisting of avidin, albumin, gelatin, lysozyme and amphilic triblock peptides.

In other embodiments the therapeutic agent is IGF.

In other aspects a composition of a nanoparticle of avidin or a fragment thereof and a therapeutic agent selected from the group consisting of a Disease Modifying Osteoarthritis Drug (DMOAD), a pro-anabolic growth factors and an anti-catabolic agent is provided. The therapeutic agent in some embodiments is dexamethasone.

In some embodiments the avidin or fragment thereof is full length avidin. In other embodiments the avidin or fragment thereof is a fragment of SEQ ID NO. 1. In yet other embodiments the avidin is linked to the therapeutic agent through a covalent linkage such as an ester or hydrazone linkage. In other embodiments the avidin is linked to the therapeutic agent through a non-covalent linkage.

The avidin in some embodiments is associated with 1-4 biotin molecules.

This invention is not limited in its application to the details of construction and the arrangement of components set forth in the following description or illustrated in the drawings. The invention is capable of other embodiments and of being practiced or of being carried out in various ways. Each of the above embodiments and aspects may be linked to any other embodiment or aspect. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

FIGS. 1A and 1B. (FIG. 1A) depicts a transport chamber designed to enable one-way diffusion (X direction) of solutes into cartilage half disks entering from the superficial zone. (FIG. 1B) A slice (100-200 μm thick) was cut from the center of the cartilage half disk (6 mm diameter, 1 mm thick) and imaged via confocal microscopy at 10× magnification in the X-Y plane of the slice to assess penetration and X-directed solute concentration profile after a selected duration of solute transport. Arrows indicate the direction of solute diffusion through the superficial zone (SZ). Images of the middle region of the slice (shown by dotted boundary) were taken to avoid any edge effects from the top and bottom of the half disk. A FITC (fluorescein isothiocyanate) filter cube was used for imaging FITC conjugated solutes. Quantum dots (QDs) were imaged using a filter cube containing 565/30 nm filter for green QDs, 640/50 nm filter for red QDs and a 625 nm LP dichroic mirror.

FIG. 2A depicts 24 h uptake of 15 nm neutral. FIG. 2B depicts positively charged QDs; arrows show cartilage superficial zone. FIG. 2C depicts 24 h desorption (into 1×PBS bath) of 15 nm neutral and FIG. 2D positively charged QDs.

FIG. 3A depicts the profile of FITC (MW 389 Da, diam~0.9 nm) FIG. 3B depicts the profile of FITC-dextran (MW 8 kDa, diam~4.3 nm). FIG. 3C depicts the profile of FITC-dextran (MW 40 kDa, diam~10 nm) after diffusion into cartilage for 24 h. FIG. 3D graphically depicts confocal images of the concentration profile of FITC-dextran (MW 40 kDa, diam~10 nm) inside cartilage explants after diffusion for 24 h, FIG. 3E depicts for 48 h, and FIG. 3F depicts for 96 h. FIG. 3G graphically depicts confocal images of the concentration profile of NeutrAvidin (neutral charge, MW 60 kDa, diam~7 nm) after diffusion into cartilage explants for 24 h, FIG. 3H for 48 h, and FIG. 3I for 96 h.

FIG. 4A depicts the percent of the initial moles of cadmium in the bath of Cd—Se QDs that were absorbed into normal and trypsin treated bovine cartilage explants in 24 h. FIG. 4B depicts the percent of cadmium absorbed in 24 h that was retained inside the cartilage explants after 24 h desorption into 1×PBS or into 10×PBS. The explants were completely digested using $HNO_3$, and the total cadmium was detected using inductively coupled plasma mass spectrometry (ICP-MS). Data are for both normal and trypsin treated cartilage. Values are Mean±SEM, n=6 cartilage samples in each condition. Horizontal lines over bars represent significant differences between treatment groups; * indicates significant difference between trypsin treated and normal cartilage; $p<0.05$.

FIGS. 5A and 5B depict fluorescence intensity normalized by surface area in experiments of diffusion of FITC and FITC-Dextra through cartilage explants. FIG. 5A depicts FITC (300 Da), FITC-Dextran (8 kDa & 40 kDa) in 24 h and FIG. 5B depicts FITC-Dextran (40 kDa) at 24 h-96 h.

FIG. 7A depicts GAG loss from bovine cartilage. FIG. 7B depicts sulfate incorporation in bovine cartilage (Prior Art).

FIG. 10A depicts the molecular structure of PPA, PPA consists of a polyethylene-glycol-derivatized poly-L-glutamic acid backbone conjugated to drugs through an optional linker to control drug release rate. FIG. 10B depicts dynamic light scattering of PPA NPs. Sizes appear smaller than expected based on size selection filters but the trend is consistent. (inset) Gel permeation chromatography of a 5 nm PPA NP after size selection is shown. FIG. 10C depicts non-specific binding of PPA NPs with serum proteins after incubation with 95% fetal bovine serum for 4 h at 37° C. No non-specific binding was observed. FIG. 10D depicts NMR results of PPA NPs. PPA NPs demonstrate high drug loading and PEGylation.

FIGS. 11A-11E depict graphs describing Avidin uptake. FIG. 11A depicts the transport chamber of FIG. 1A showing visual evidence of significantly higher uptake for Avidin compared to NeutrAvidin over a 24 h period. 'Av'=Avidin; 'Nu'=NeutrAvidin. FIG. 11B and FIG. 11C graphically depict of the concentration profile inside normal cartilage explants of Avidin (positive charge, MW 66 kDa, diam~7 nm), and NeutrAvidin after 24 h absorption into normal cartilage explants. FIG. 11D and FIG. 11E graphically depict the effects of 24 h desorption of Avidin into (FIG. 11D) 1×PBS and (FIG. 11E) 10×PBS.

FIGS. 12A-12C depict graphs of the uptake ratios measured for Avidin, NeutrAvidin and desorption results. FIG. 12A and FIG. 12B depict (FIG. 12A) Avidin and (FIG. 12B) NeutrAvidin after 1 to 4 day equilibration periods for normal and 40% GAG-depleted cartilage explants (via chondroitinase-ABC) FIG. 12C depicts the percent of moles absorbed in 24 h that was retained inside the explants after desorption into 1× and 10×PBS for Avidin and NeutrAvidin. Values are Mean±SEM; n=18 cartilage samples (6 disks from each of 3 animals) per treatment group for normal cartilage condition, and n=6 cartilage samples per treatment group (from 1 animal) for 40% GAG-depleted cartilage. Horizontal lines over bars represent statistical significant differences between treatment groups; * indicates significant difference between GAG-depleted and normal cartilage; $p<0.05$.

FIG. 18A depicts sGAG concentration measured using the DMMB assay in different tissue types of rat knee expressed as µg sGAG per mg wet weight of tissue. Data is presented at Mean+/−SD, N=7 animals. * represents statistical significance compared to cartilage; $p<0.05$. FIG. 18B depicts sGAG concentration vs. Avidin half-lives for different tissue types (C—articular cartilage; QT—Quadriceps Tendon; L—Ligaments (ACL & PCL); M—Menisci; PT—Patella Tendon). Diamonds represent experimental data, solid line is the linear least squared fit and dotted lines show 95% confidence interval. $R^2=0.83$ FIGS. 19A-19J depict a set of images showing toluidine blue staining of naïve rat knee tissues, sectioned in either the coronal (FIGS. 19A-19B) or sagittal (FIGS. 19C-19J) plane. Pictures were taken with 2.5× (FIGS. 19A, 19C, 19E, 19G, and 19I) and 10× magnification (FIGS. 19B, 19D, 19F, 19H, and 19J). (FIGS. 19A-19B) Medial femoral condyle with underlying epiphyseal plate. (FIGS. 19C-19D) Medial joint compartment showing tibial plateau and meniscus. (FIGS. 19E-19F) Femoral trochlea and patellar tendon. (FIGS. 19G-19H) Quadriceps tendon and adjacent suprapatella along with proximal portion of patellar bone and cartilage. (FIGS. 19I-19J) Anterior cruciate ligament with tibial and femoral attachments. ACL—anterior cruciate ligament, AHC—articular hyaline cartilage, AHMM—anterior horn of the medial meniscus, BM—bone marrow, EP—epiphyseal plate, FB—femoral bone, HFP—Hoffa's fat pad, PB—patellar bone, PT—patellar tendon, QT—quadriceps tendon, SP—suprapatella, SY—synovium, TB—tibial bone.

FIG. 20A depicts cumulative sGAG loss from bovine cartilage to the medium in response to 4 and 10 day treatment with 0, 100 nM, 1 µM and 100 µM one time dose of Avidin. Media was changed every two days without replenishing Avidin. FIG. 20B depicts bovine chondrocyte protein synthesis and FIG. 20C depicts sGAG synthesis during the last 48 h of culture were measured using Proline (H3) and Sulfate (S35) incorporation rates, respectively, for the same cartilage disks as in FIG. 20A. Values are Mean+/−SEM; N=2 animals (6 disks/animal). * represents statistical significance compared to control untreated condition; $p<0.05$

FIG. 22A depicts drug release rates for supra-molecular entrapment (non-covalent) structures. FIG. 22B depicts comparison of drug release rates from structures with ester linker (covalent) and non-covalent conjugation. FIG. 22C depicts drug release rates for hydrazone (covalent) linker at pH7 and pH 4.

FIG. 25A shows the percent cumulative sGAG loss achieved when cartilage tissue was exposed to either control, IL-1 (1 ng/ml), a single dose of dexamethasone (100 μm), a single dose of avidin-dexamethasone particles (25-100 μm), or a continuous dose of Dexamethasone (100 nM) over the course of 8 days. FIG. 25B shows the rate of sGAG synthesis for each of the same conditions.

DETAILED DESCRIPTION

Figure 2A:
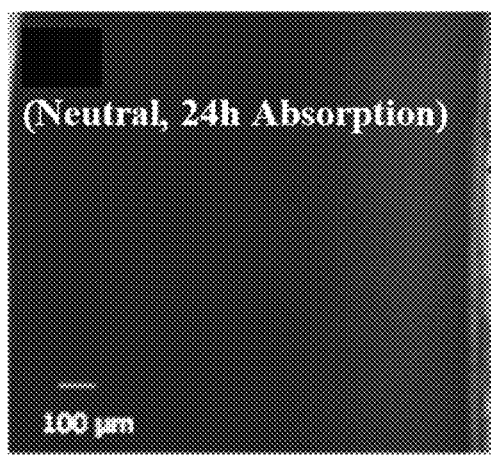
FIGS. 2A-2D depict quantum dot (QD) uptake into cartilage disks.

Methods and reagents facilitating particle based drug delivery systems for the prevention and/or treatment of diseases are provided according to the invention. In particular the particle systems described herein are useful for delivering agents to bone and connective tissues, for example, for the treatment of musculoskeletal disease and/or injury. It is important for a delivery system used in the treatment of musculoskeletal disease and/or injury to enable drug penetration into the deeper zones of cartilage and other connective tissue or bone. The compositions of the invention are effective in enabling drug penetration into deep tissue zones as well as for facilitating retention of the drug within tissue for several weeks to ensure effective treatment. These effects provide a considerable advance in the field, as conventional therapeutics fail to penetrate deeply and provide sustained drug delivery. The particles are also useful for achieving local delivery of any agent which cannot be delivered systemically, for instance because of toxicity or stability issues. For example the particles of the invention can be used to deliver IGF to bone tissue.

The methods of the invention, in some instances, involve the use of larger particles which are unable to penetrate through the connective tissue and/or smaller particles which are able to penetrate the connective tissue. The surface of the larger particles may be functionalized with a connective tissue binding compound to enable binding to the surface of the cartilage. For example, drugs having low molecular weights (e.g. steroids or glucocorticoids (~300 Da)), may be conjugated to or incorporated into nanoparticles of less than 10 nm in size. Larger drugs, such as growth factors like IGF (~7 kDa), may be tethered to the surface of or incorporated into larger particles (10 nm or greater). A combination of the two approaches utilizing different sizes of particles allows for the delivery of multiple drugs into cartilage having anti-catabolic and pro-anabolic properties.

Thus, the invention, in some aspects, relates to microparticles, nanoparticles and compositions thereof as well as uses thereof. A "microparticle" as used herein is a particle having an average particle size of greater than 10 nm. In some embodiments the microparticle has a size of greater than 10 nm to 100 nm. In other embodiments the microparticle has a size of greater than 10 nm to 80 nm, 50 nm, 40 nm, 30 nm, 20 nm, or 15 nm. In some instances the minimum size of the microparticle is 12 nm, 15 nm, 20 nm, 25 nm, or 30 nm. In some instances the maximum size of the microparticle is 500 nm, 250 nm, 200 nm, 100 nm, 50 nm, 20 nm, or 15 nm. The term "micro" in microparticle does not refer to a particle having a micron size. Rather, in the context of this patent application the term microparticle is used to refer to the larger of the two types of particles described herein.

A "nanoparticle" as used herein is a particle having an average particle size of 10 nm or less. An average particle size refers to the average particle diameter within a group of particles. In some embodiments the microparticle has a size of 1-10 nm, 2-10 nm, 3-10 nm, 4-10 nm, 5-10 nm, 6-10 nm, 2-8 nm, 3-7 nm, or 1-9 nm.

In other instances, the particles are composed of a polymer having a net positive charge of greater than 6. The polymer may, for instance, have a molecular weight of less than 90 kd and be a peptide. Peptide based nanoparticles having a net positive charge of great than 6. In some instances the nanoparticle has a net positive charge of 7-14. These nanoparticles are particularly useful for penetrating the connective tissue. Useful peptides include but are not limited to avidin, albumin, gelatin, lysozyme and amiphilic triblock peptides and fragments thereof.

Non-limiting examples of peptide based nanoparticles of the invention are shown in FIG. 21. An exemplary nanoparticle useful according to the invention is an avidin peptide, wherein the avidin is conjugated either covalently or non-covalently to an active agent such as dexamethasone. The avidin may be linked to the dexamethasone directly through an ester or hydrazone linkage to the dexamethasone. Alternatively the avidin may be linked to one or more biotins which are connected to the dexamethasone covalently through one or more of these linkages or non-covalently associated with dexamethasone. Avidin can associate with 1-4 biotin molecules. Structures having avidin linked to no biotin or 1, 2, 3 or 4 biotins are envisioned according to the invention. Each of the biotins may then be linked directly or indirectly through the same or different linkages to the active agent.

The term "particle" is used herein to refer collectively to the microparticles and nanoparticles described herein. The particles of the invention are designed to interact with the connective tissue, which is typically difficult to access with therapeutics. For instance, cartilage is a highly complex, avascular, alymphatic tissue made of a dense network of collagen fibrils, aggrecan proteoglycans containing highly negatively charged GAG chains, and many additional extracellular proteins continually synthesized by a low density of cells (chondrocytes). It is challenging to deliver drugs to cartilage in any form of sustained release system because penetration into the dense networked tissue is so difficult.

Figure 8:
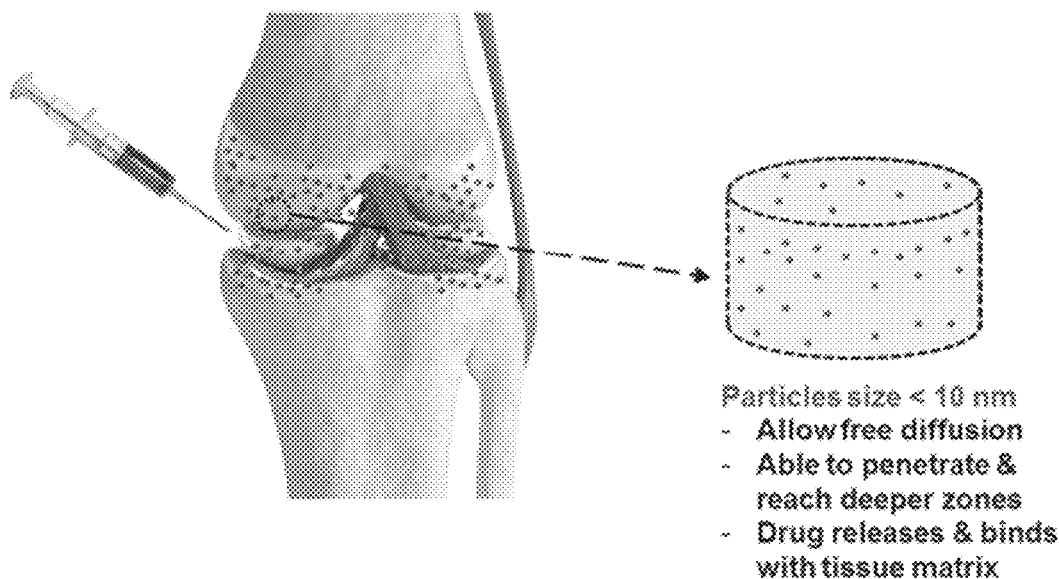
FIG. 8 depicts the free diffusion of nanoparticles approach (FDN) involving 10 nm carrier particles.

Nanoparticles are designed with smaller diameters (approximately 10 nm or less) so that they may be able to penetrate and diffuse into and through the tissue. As these particles gradually degrade, they release drug contained within and bound to the particle surface. Protein drugs may have binding properties that enable them to bind reversibly within the cartilage matrix (e.g., the binding of growth factors with a heparin-like binding domain to chondroitin sulfate and heparan-sulfate GAG chains). A schematic of the use of nanoparticles is depicted in FIG. 8.

Figure 9:
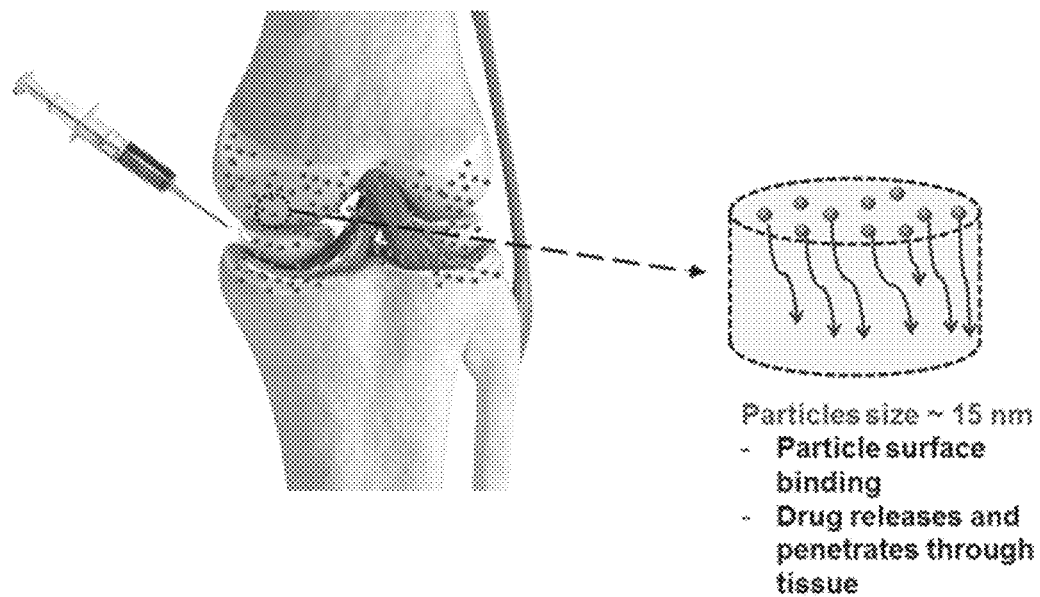
FIG. 9 depicts the surface binding of nanoparticles approach (SBN) involving charged carrier particles of greater than 10 nm in size.

Microparticles are larger than the nanoparticles described herein. The use of microparticles as described herein is depicted in FIG. 9. In this approach particles are enabled to first bind within the surface layers (superficial zone) of the cartilage. As the particles gradually degrade, they release the drugs, providing a sustained drug release over a period of time. Due to the much lower MW (~kDa) of the drugs, they are able to diffuse throughout the thickness of the cartilage tissue.

The particles of the invention may be made from any materials known in the art for preparing particles. For instance, the particles may be made of polymers.

Any polymer may be used in the particles of the invention. In certain embodiments, polymers known to be suitable for use in biological systems are used, such as for instance, biocompatible polymers. The polymer may be FDA approved for use in humans and/or animals. In some embodiments, the polymer is biodegradable. Polymers include but are not limited to pegylated Poly-L glutamic acid (PPA), polyesters, polyanhydrides, polyethers, polyamides, polyacrylates, polymethacrylates, polycarbamates, polycarbonates, polystyrenes, polyureas, polyamines, polyacrylamides, poly(ethylene glycol), poly(hydroxyethylmethacrylate), poly(vinyltoluene), and poly(divinylbenzene). In certain embodiments, the polymer is a mixed polymer, a linear co-polymer, a branched co-polymer, or a dendrimer branched co-polymer. In other embodiments, a synthetic polymer (e.g., poly(lactic-co-glycolic acid) (PLGA), polyglycolic acid (PGA), polyesters, polyanhydrides, polyamides, etc.) is used. In other embodiments, the polymer is poly(lactic acid) (PLA), a poly(glycolic acid) (PGA) or a poly(beta-amino ester).

The polymers may be prepared from one or more of the following monomers: acrylic acid, or any ester thereof, such as methyl acrylate, ethyl acrylate, propyl acrylate, butyl acrylate, 2-ethyl hexyl acrylate or glycidyl acrylate; methacrylic acid, or any ester thereof, such as methyl methacrylate, ethyl methacrylate, propyl methacrylate, butyl methacrylate, lauryl mathacrylate, cetyl methacrylate, stearyl mathacrylate, ethylene glycol dimethacrylate, tetraethylene glycol dimethacrylate, glycidyl methacrylate or N,N-(methacryloxy hydroxy propyl)-(hydroxy alkyl) amino ethyl amidazolidinone; allyl esters such as allyl methacrylate; itaconic acid, or ester thereof; crotonic acid, or ester thereof; maleic acid, or ester thereof, such as dibutyl maleate, dioctyl maleate, dioctyl maleate or diethyl maleate; styrene, or substituted derivatives thereof such as ethyl styrene, butyl styrene or divinyl benzene; monomer units which include an amine functionality, such as dimethyl amino ethyl methacrylate or butyl amino ethyl methacrylate; monomer units which include an amide functionality, such as acrylamide or methacrylamide; vinyl-containing monomers such as vinyl ethers; vinyl thioethers; vinyl alcohols; vinyl ketones; vinyl halides, such as vinyl chlorides; vinyl esters, such as vinyl acetate or vinyl versatate; vinyl nitriles, such as acrylonitrile or methacrylonitrile; vinylidene halides, such as vinylidene chloride and vinylidene fluoride; tetrafluoroethylene; diene monomers, such as butadiene and isoprene; and allyl ethers, such as allyl glycidyl ether.

The polymer may also be a peptide. Peptides include but are not limited to avidin, albumin, gelatin, lysozyme and amphilic triblock peptides and fragments thereof. In some embodiments the particle is made of avidin or fragments thereof. For instance, the amino acid sequence of avidin is: mvhatsplll llllslalva pslsarkcsl tgkwtndlgs nmtigavnsr geft-gtyita vtatsneike splhgtqnti nkrtqptfgf tvnwkfsest tvftgqcfid rngkevlktm wllrssvndi gddwkatrvg iniftrlrtq ke (SEQ ID NO 1). A fragment of avidin is any peptide sequence of at least 5 amino acids in length that is found within the avidin protein. In some embodiments it is at least 6, 7, 8, 9, 10, 11, 12, 13, 14, 15, 16, 17, 18, 19, or 30 amino acids. amphilic triblock peptides include for instance, peptides such as:

[SEQ ID NO: 2]
WWWWWHHHHRRRRRRR;

[SEQ ID NO: 3]
IIIIIHHHHRRRRRRR;

[SEQ ID NO: 4]
FFFFFHHHHRRRRRRR;

[SEQ ID NO: 5]
AAAAAAAAAAAAHHHHKKKKKKKKKK;
and

[SEQ ID NO: 6]
AAAAAAAAAAAAHHHHKKKKKKKKKKKKKKK.

The peptides may be a variety of sizes. In some instances the peptides have a lower size limit of 5, 6, 7, 8, 9, 10, 11, 12, 13, 14, 15, 16, 17, 18, 19, or 30. In other instances the peptides have an upper size limit of 500, 450, 425, 400, 375, 350, 325, 300, 275, 250, 225, 200, 175, 152, 150, 125, 100, 90, 80, 75, 70, 65, 60, 55, 50, 45, 40, 35, 30, 25, 20, 15, 10, or 9. The peptides useful according to the invention include any combination of the stated lower and upper size limits to form a range of size limits.

A "peptide" or "protein" refers to a string of at least three amino acids linked together by peptide bonds which may be used interchangeably. Peptide may refer to an individual peptide or a collection of peptides, including only natural amino acids, as well as, non-natural amino acids (i.e., compounds that do not occur in nature but that can be incorporated into a polypeptide chain) and/or amino acid analogs. Also, one or more of the amino acids may be modified, for example, by the addition of a chemical entity such as a carbohydrate group, a phosphate group, a farnesyl group, an isofarnesyl group, a fatty acid group, a linker for conjugation, functionalization, or other modification, etc. Other modifications may include cyclization of the peptide, the incorporation of D-amino acids, etc.

The particle may be a lipid particle. Some lipid particle systems include a lipid component, a cationic surfactant, a non-ionic surfactant, a polysaccharide and/or a positively charged peptide.

In other embodiments, the polymer is a carbohydrate (e.g., dextran, fructose, fructose, glucose, invert sugar, lactitol, lactose, maltitol, maltodextrin, maltose, mannitol, sorbitol, sucrose, trehalose, isomalt, xylitol, polydextrose, cellulose, methylcellulose, amylose, dextran, dextrin, starch, etc.).

In certain embodiments, the average molecular weight of the polymer ranges from 1,000 g/mol to 50,000 g/mol, preferably from 2,000 g/mol to 40,000 g/mol, more preferably from 5,000 g/mol to 20,000 g/mol, and even more preferably from 10,000 g/mol to 17,000 g/mol.

Blends of polymers may also be used in the particles of the invention. The blends may contain 2, 3, 4, 5, 6, 7, 8, 9, 10, or more different polymers. In certain embodiments, the blend may contain 2 or 3 different polymers, such as poly-lactic-co-glycolic acid (PLGA) and/or poly(beta-amino ester).

The microparticle and nanoparticle may be coformulated as a composition such that particles are designed for long term retention in the joint space and controlled release of the drug at the desired rate for localized treatment with minimized toxicity and immediate release of agents, such as pain relievers from smaller particles. A preferred polymer that may be used includes but is not limited to Pegylated Poly-L Glutamic Acid (PPA), a graft copolymer of FDA approved polymers for therapeutic use.

The ability to design adequately sized and charged particles is important. The first step involves determining the optimal size and surface chemistry of these particles that can either penetrate into and through the cartilage or bind at the tissue surface. As shown in the Examples, we have conducted experiments using nano sized quantum dots. Results demonstrated that 15 nm diameter quantum dots (microparticles) can penetrate the superficial most ~50 microns of the tissue. It was also discovered that positively charged quantum dots were able to bind with the highly negatively charged cartilage matrix.

The particles, and in particular the microparticles may be functionalized with a connective tissue binding compound. A connective tissue binding compound is any compound which is capable of binding to one or more connective tissues. The microparticles (for example, >10 nm) containing functional groups that can enable binding to the cartilage surface and hence, provide a long term sustained drug delivery. These particles will degrade and release the drug, which due to its low molecular weight will be able to diffuse freely throughout the tissue. The connective tissue binding compound facilitates the binding of the microparticle to the connective tissue in vivo. Connective tissue binding compounds include but are not limited to amines, Lysines, Arginines, functional groups that can bind specifically to the macromolecules/proteins found in the connective tissue. Connective tissue includes Cartilage (all types: elastic, hyaline, fibrocartilage which is found in many areas of the body including joints between bones, rib cage, ear, nose, invertebral discs, articular disc of TMJ) and in particular the superficial zone of the cartilage, elements of the synovial capsule like the synovial membrane, synovial lining, meniscus, ligaments, and tendons. The superficial tangential zone of cartilage contains the highest collagen content, about 85% by dry weight. Macromolecules/proteins found in the connective tissue include but are not limited to lubricin, Collagen VI, Collagen IX, proteoglycans, glycoproteins, elastin, fibrillin, fibronectin, and laminin.

In some instances the connective tissue binding compound is a cartilage binding compound. A cartilage binding compound is any compound that binds to cartilage or surrounding tissues to cause the particles to remain in the local area. Cartilage binding compounds can be, for instance, peptides, polysaccharides, or small molecules.

The particles of the invention are useful for delivering agents to the connective tissues. In some instances, a combination of agents in various proportions can be delivered. The timing of drug release can be controlled by controlling the microparticle properties. For instance a first agent can be incorporated into a microparticle designed to release the agent slowly over time. Microparticle release properties are well known in the art. A second agent can be included in the nanoparticle, such that it is delivered quickly to the tissue and release rapidly.

A particle loaded with an active agent refers to a particle that is somehow associated with an active agent. The active agent may be integrated throughout the particle or it may be conjugated on the surface or it may be associated in any other possible way with the particle, such as encapsulated within the particle.

The microparticle includes a first active agent and the nanoparticle includes a second active agent. The first and second active agent may be the same active agents or different active agents. An active agent as used herein refers to any compound which is capable of having an effect in connective tissue. Typically the active agent, first or second active agent, is a therapeutic compound for the treatment of a musculoskeletal disease, a passive agent that is useful for treating symptoms of the disease, such as analgesics or anti-inflammatory agents, or a diagnostic or other research based agent.

Therapeutic agents for the treatment of a musculoskeletal disease are compounds which have an influence on the disease. These agents include but are not limited to Disease Modifying Osteoarthritis Drug (DMOAD), pro-anabolic growth factors and anti-catabolic agents. Pro-anabolic factors include but are not limited to IGF (Insulin like Growth Factors): eg, IGF-1, FGF-15 (fibroblast growth factor), and BMP7 (bone morphogenetic protein). Anti-catabolic agents include but are not limited to the glucocorticoid class of steroid drug (e.g., glucocorticoids such as Triamcinolone, Dexamethasone, etc.), and can include other agents such as blockers of inflammatory cytokines (e.g., inhibitors of TNF (tumor necrosis factor), IL-1 (interleukin), and proteinases such as Aggrecanases and Matrix Metalloproteinases).

Passive agents are compounds that exert a biological effect in the connective tissue, such as pain relief or reduction in inflammation. Passive agents include but are not limited to analgesics, such as clonidine, capsaicin, lidocaine, bupivacaine, mepivacaine, ropivacaine, tetracaine, etidocaine, chloroprocaine, prilocaine, procaine, benzocaine, dibucaine, dyclonine hydrochloride, pramoxine hydrochloride, benzocaine, proparacaine, eptazocine, tramadol and pentazocine, Non Steroid Anti-inflammatory Drugs (NSAIDs), such as aspirin, and ibuprofen.

Diagnostic agents include gases; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium.

The compositions of the invention are useful for treating musculoskeletal diseases. A "musculoskeletal disease" as used herein refers to a disorder that affects the body's muscles, joints, tendons, ligaments and nerves. These diseases include but are not limited to Osteoarthritis, Back pain, Rheumatoid arthritis, Osteoporosis, Septic arthritis, gout, Fibromyalgia, and Systemic lupus erythematosus (SLE).

Rheumatoid arthritis is an autoimmune chronic systemic disease characterized by a symmetrical inflammatory polyarthritis that causes progressive joint damage and disability in young people, and extra-articular involvement of lungs and other organs. Septic arthritis results from infection of joints with pyogenic organisms, the most common being *Staphylococcus aureus*, which can reach the joint via the bloodstream, a local site of infection such as a boil, or occasionally from an adjacent site of osteomyelitis. Gout is an abnormality of uric acid metabolism in which crystals of sodium urate become deposited in the joints, soft tissue, and urinary tract. SLE is characterized by the presence of antibodies against nuclear components. It is a multisystem disease, with arthralgia and rashes the most common clinical features, but vasculitis and disorders of the lung, heart, kidney, nervous system, and eye and involvement of the GI tract can all occur.

In some embodiments the musculoskeletal disease is osteoarthritis. Osteoporosis is a common disorder resulting in a reduction in bone mass. Osteoarthritis is one of the most common chronic illnesses affecting over 150 million people worldwide, making it one of the most prevalent diseases in the world (WHO, 2009). OA attacks body joints, affecting productivity and quality of life, and is extremely disabling to the patient. While great advances have been made in developing drugs for rheumatoid arthritis (RA), there is no disease modifying drug available for OA.

Current therapies only provide short term pain and inflammation relief but afford no protection against the inevitable further degeneration of joint cartilage, the hallmark of end-stage OA. This results in complete joint dysfunction (including deterioration of bone and other soft tissues), leading to the patient's need for joint replacement. It is thus vital to further understand OA disease mechanisms and to develop effective therapeutics and drug-delivery systems for curing it. Importantly, recent interest has focused on post-traumatic OA, involving joint-injured patients (e.g., anterior cruciate ligament (ACL) rupture from sports injury in young individuals). This patient population has a high rate of progression to OA, thereby defining opportunities for early intervention and a population for staging potential clinical trials, since the exact cause and time of the initiating trauma is known (Anderson et. al., J. Orthop. Res. 2011).

However, it is increasingly recognized that cell biological and biochemical (proteolytic) abnormalities within the joint precede radiographic abnormalities in OA progression by many years. The invention provides a new opportunity to intervene early and treat the disease since the exact time of injury is known. This early form of treatment can be considered analogous to a 'vaccine' that is administered immediately following an injury to prevent the development of arthritis and repair injured cartilage. A short term (several months) treatment may be efficacious for treating very early stage OA. It is important that such drugs be delivered locally and safely into the afflicted joint to prevent systemic side effects. Additionally, important that the drug penetrate into and through the cartilage and be retained inside the joint cartilage for several weeks to ensure effective treatment. The particle based drug delivery system of the invention allows for the administration of multiple bioactive molecules to enable local delivery and retention.

Thus, the drug delivery mechanism is not restricted to treating disorders such as post traumatic OA but can be used for delivering therapeutic agents and pain killers into the joint at later stages of OA and/or for any other type musculoskeletal disease requiring localized treatment in humans and animals.

Figure 6:
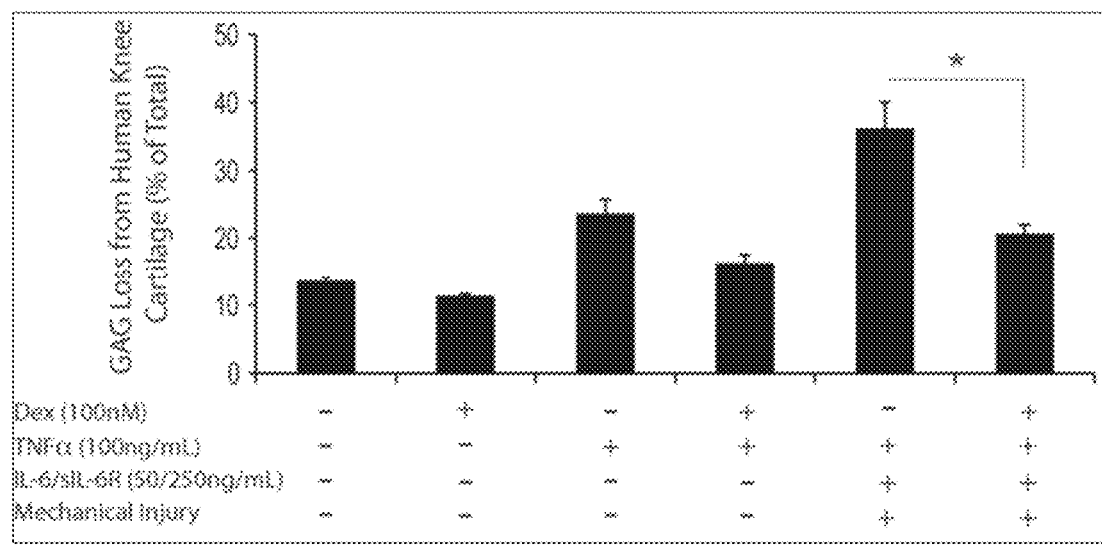
FIG. 6 depicts the effects of dexamethasone on normal human knee cartilage (donor tissue) treated with mechanical injury and a combination of TNFα and IL-6, using the in vitro system to simulate joint injury (Prior Art).
Figure 7A:
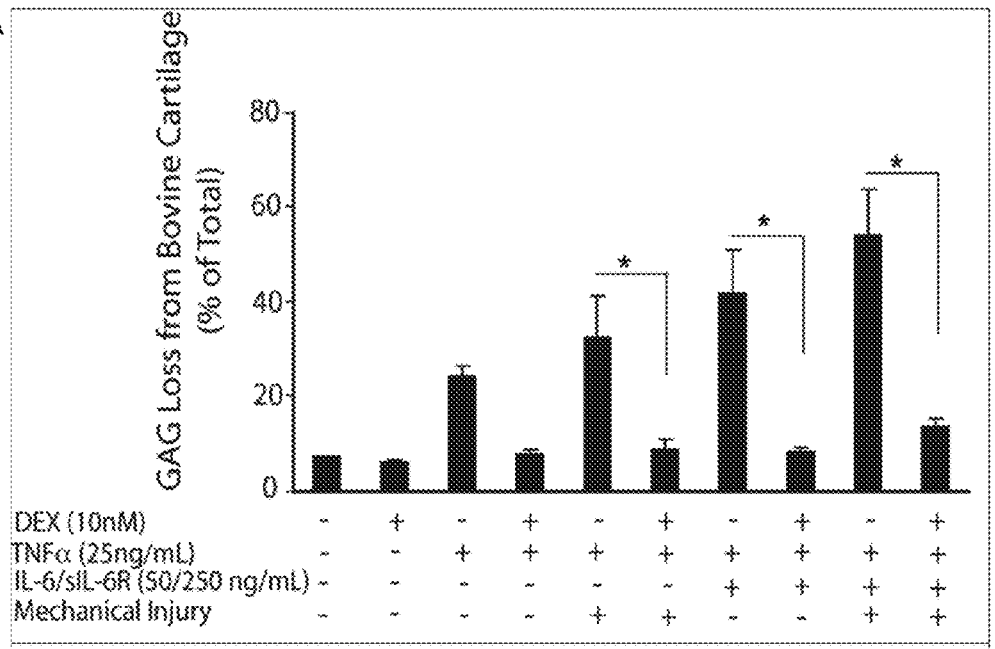
FIGS. 7A and 7B depict the effects of dexamethasone on GAG loss & chondrocyte biosynthesis in normal bovine cartilage.
Figure 7B:
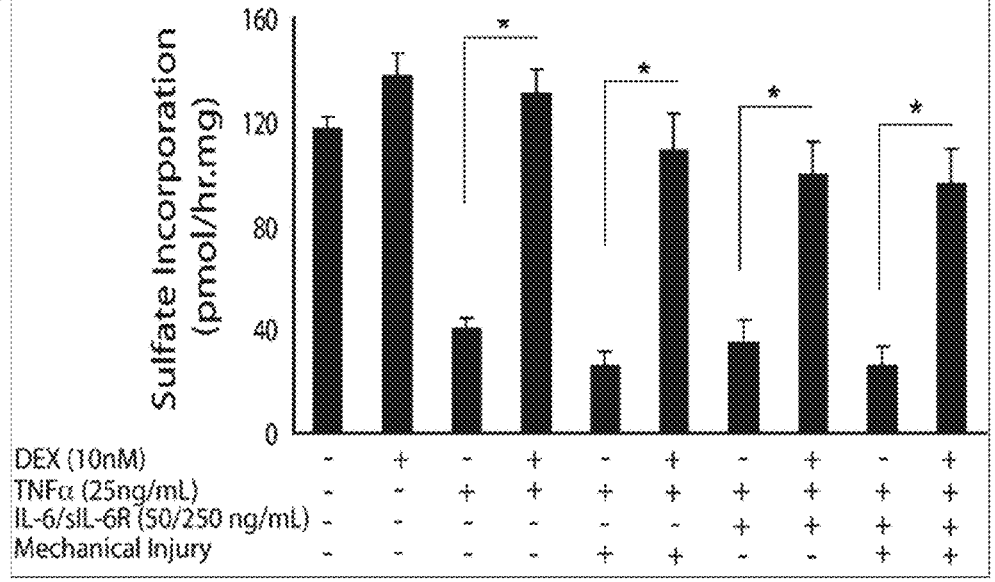

The inventors have recently shown that short term treatment of animal cartilage with dexamethasone and pro-anabolic agents inhibits cartilage degeneration after injury in vitro and restores biosynthesis levels to normal (Lu et. al., Arthritis Res. 2011). Current work (Y Wang, Y Li, P Kopesky, S G Chubinskaya, B Schoeberl, A J Grodzinsky, IGF-1 and Dex Reduced Matrix Degradation in IL-1α-Treated Bovine Cartilage and IL-1α±Injury-treated Human Cartilage, Trans Orthop Res Soc, San Antonio, Jan. 26-29, 2013) show similar positive effects in human cartilage. It was demonstrated that short term treatment of human and bovine cartilage explants in vitro with dexamethasone (DEX) can inhibit the progression of cartilage degradation and maintain tissue synthesis when administered immediately after injury. This treatment may be used to prevent the onset of OA when administered right after an injury. These prior data are shown in FIGS. 6 and 7. 100 nM DEX treatment of human cartilage significantly reduced aggrecan-GAG loss caused by mechanical injury and the inflammatory cytokines TNFα and IL-6 (FIG. 6). FIGS. 7A and 7B show that only 10 nM DEX treatment of bovine cartilage significantly reduced GAG loss, and restored aggrecan-GAG biosynthesis levels back to normal. The in vitro cartilage organ culture system was set up in a manner that simulates the conditions in the microenvironment of joint cartilage in the weeks immediately following a joint injury (such as ACL rupture) (Lu et. al., Arthritis Res. 2011).

While these studies provided a great advance in the field, problems remain with the therapeutic treatment of musculoskeletal disease. For instance, chronic systemic use of DEX and growth factors causes negative systemic side effects. There are no drug delivery techniques currently available for sustained, local delivery of such compounds to specific target tissues in the joint. A persistent problem in the development of OA treatment is that oral or IV-injection distributes drugs to the entire circulatory system, thereby reducing their specificity to the affected joint tissues and causing systemic adverse effects.

The findings of the invention solve prior art problems. For instance, the invention involves the development of a drug delivery system that results in the administration of drugs such as glucocorticoids and biologic formulations locally to specific joint tissues, thereby enabling optimum drug concentration in the affected region while minimizing delivery elsewhere. The compositions of the invention also have an advantage of increased drug retention time and controlled drug release rates. In particular the compositions enable drug penetration into the deeper zones of cartilage and retention of the drug inside the cartilage for several weeks to ensure effective treatment.

The compositions are administered to a subject. A subject shall mean a human or other mammal including but not limited to a dog, cat, horse, cow, pig, sheep, goat, turkey, chicken, and primate, e.g., monkey. In some embodiments the subject has musculoskeletal disease or osteoarthritis.

The active agent is delivered to the connective tissue as it is released from the microparticle or nanoparticle. In some instances the compositions of the invention are delivered to a joint of a subject. Joints include but are not limited to knee, hip, ankle, spine, shoulder, and elbow joints. Arthroscopic procedures are now routinely done on these joints.

As used herein, the term treat, treated, or treating when used with respect to a disorder such as osteoarthritis refers to a therapy that at a minimum prevents further damage associated with the connective tissue when compared to the absence of the treatment in order to prevent the osteoarthritis from becoming worse. In some instances the treatment will result in an improvement in symptoms in the subject and in some instances a complete therapeutic recovery such that the subject becomes symptomless. It also refers to the treatment of a subject that is at risk of developing osteoarthritis to prevent or lessen the impact of such a disorder if the subject does develop it.

The term effective amount of an active agent refers to the amount necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular active agent being administered the size of the subject, or the severity of the disease or condition. One of ordinary skill in the art can empirically determine the effective amount of a particular active agent without necessitating undue experimentation.

Subject doses of the active agents to be used in the particles described herein typically range from about 0.1 µg to 10 mg per administration, which depending on the application could be given daily, weekly, or monthly and any other amount of time there between. More typically doses range from about 10 µg to 5 mg per administration or particle, and most typically from about 100 µg to 1 mg. More typically, doses range from 1 µg to 10 mg per administration, and most typically 10 µg to 1 mg.

For any compound described herein the therapeutically effective amount can be initially determined from animal models. A therapeutically effective dose can also be determined from human data for active agents which have been tested in humans. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the particles and active agents associated therewith can be administered to a subject by any mode that delivers the particle to the desired connective tissue surface. In some embodiments intra-articular injection is a preferred mode of administration for the particles of the invention. Depending on the particular drug, other routes of administration include but are not limited to oral, parenteral, intramuscular, intranasal, sublingual, intratracheal, inhalation, ocular, vaginal, and rectal.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

The experiments described herein demonstrate that particles that can bind to the tissue surface are capable of providing sustained delivery by gradually degrading and releasing their drug payload. These drugs (pro-anabolic+ anti-catabolic) can diffuse throughout the cartilage and reach their targets, (cells and matrix) even in the deepest zones.

Example 1

Development of Compact Biocompatible Polymeric Particles

Polyethylene-glycol-derivatized poly-L-glutamic acid (PPA) NPs are engineered in (i) distinct sizes between 5 to 15 nm, (ii) that have narrow size distribution, (iii) have high drug loading, (iv) have controllable PEGylation, (v) have variable surface charge, (vi) have surface functionalization, (vii) are amenable to scale-up and manufacture, (viii) are versatile for conjugation to various drugs, (ix) and have high safety.

Figure 10A:
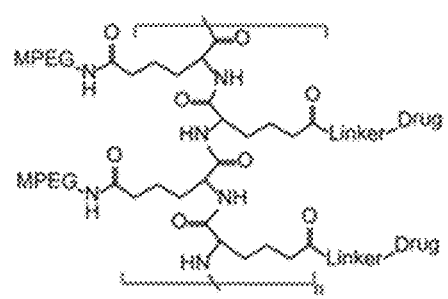
FIGS. 10A-10D depict the characteristics of the PPA drug polymer conjugate.
Figure 10B:
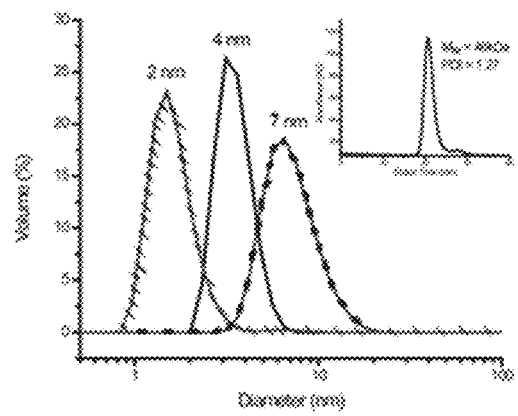
Figure 10C:
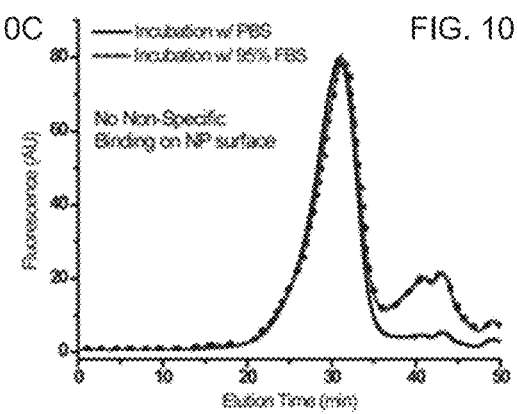
Figure 10D:
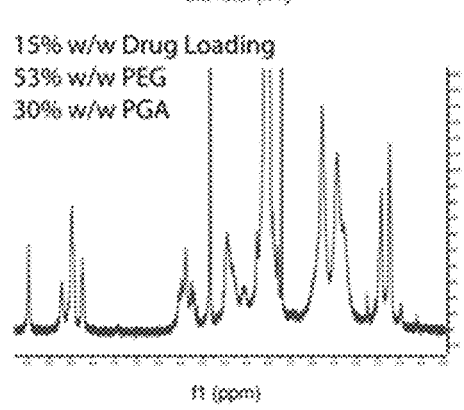

For optimal therapeutic efficacy, the particles can be designed to maximize penetration, drug concentration time and the spatial profile in cartilage. Some preferred nanoparticles are manufactured smaller than 10-nm for penetration, yet are big enough that they do not quickly clear from synovial fluid. A set of nanoparticles having a narrow size distribution was developed using filtration through a series of different membrane pore sizes (FIG. 10B inset). Additionally, a technique referred to as "living polymerization" was used to work with and synthesize monodisperse poly-L-glutamic acid (PGA). This technique may be used to synthesize PGA from 3 kDa to 120 kDa with a PDI between 1.01 to 1.04. PEG was added up to 60% w/w which is important for allowing higher MW polymers to be water soluble. Up to 60% w/w PEG allows drug loading to be increased up to 38% w/w depending on the amount of PEGylation. The surface charge may be altered and functionalization may be added to the particles by replacing methoxy-PEG with amino-PEG.

Example 2

Determination of Optimal Size of Particles

Studies were conducted using nano sized quantum dots to understand the transport of particles into living bovine cartilage explants. It is preferable for the drug to penetrate through the thickness of cartilage and be retained for effective treatment. Bovine explants were incubated in 15 nm neutral quantum dots for different time periods in a specialized transport chamber such that the particles entered the cartilage surface zone (right hand side of FIGS. 2A and 2B, Transport from right to left of neutral (FIG. 2B) and positively charged (FIG. 2A) quantum dots in 24 h showed penetration into the top 50 microns of the superficial zone of 1 mm-thick cartilage explants.

The data demonstrate that 15 nm diameter particles are too big to penetrate into and through the complex full-thickness meshwork of cartilage. However, these results demonstrated the ability of particles of this size to remain within the cartilage surface and, upon biodegradation, unload a drug payload: i.e., sometimes referred to herein as the surface binding nanoparticle (SBN) approach.

Figure 3A:
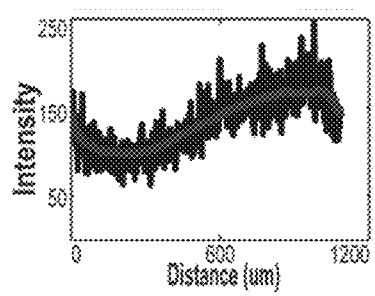
FIGS. 3A-3I graphically depict confocal images of the concentration profile inside bovine cartilage explants. The graphs depict average fluorescence intensities across the thickness of each slice (X direction of the confocal image—not shown) are plotted as a function of distance from the left edge of the confocal images.
Figure 3B:
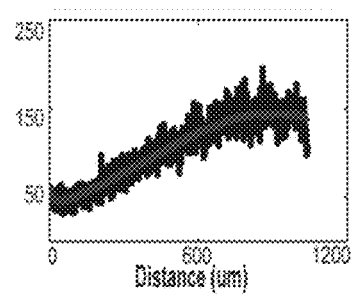
Figure 3C:
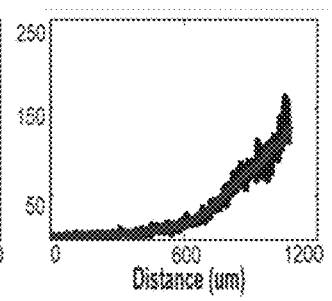

FIGS. 3A, 3B, and 3C show fluorescence graphs of diffusion of FITC-dextran (300 Da, 8 kDa, and 40 kDa) through bovine cartilage explants in 24 h. Size dependent transport was observed: 300 Da solutes were able to penetrate throughout the tissue while a penetration gradient was evident for the 40 kDa molecule. This indicates that a smaller size particle (e.g., the 7 nm nanoparticles of FIG. 10B) are sufficient to penetrate through the deeper zones of cartilage. This is sometimes referred to herein as the FDN approach.

Determination of optimal surface chemistry of particles to enable binding. Particles were developed to examine the effect of surface chemistry on binding to the cartilage matrix. Since the cartilage is heavily negatively charged, particles which contain positive amine groups which enable them to bind to the tissue have been developed and tested. The results are shown in FIG. 2. FIGS. 2C and 3D show desorption results of these samples after 24 h incubation in 1×PBS. Neutral quantum dots diffused out of the sample while the charged quantum dots did not.

Example 3

Size Dependent Transport of Nanoparticles and Macromolecules into Cartilage

Sample Preparation: Cartilage disks (6 mm diam, 1 mm thick) were harvested from the femoropatellar grooves of 1-2 week old bovine calf knee joints as described previously (Patwari et al., Arth. Rheum. 2003). Disks were pre-equilibrated in PBS (without $Ca^{2+}/Mg^{2+}$) supplemented with protease inhibitors (Roche Complete in 50 mL PBS) in 37° C., 5% $CO_2$ incubator for 48 h.

Solute Types: Two types of 15 nm diameter (MW-300 kDa) Quantum Dots (QD) were used: (i) positively charged, and (ii) charge-neutral; same concentration. Transport of FITC (MW~300 Da, diam~0.9 nm) and dextrans (Dex) conjugated with FITC (Sigma Aldrich) of different MW (~8 kDa, diam~4.3 nm; ~40 kDa, diam~10 nm) were also investigated.

Transport Studies: A special PMMA transparent transport chamber was designed to allow diffusion of solutes into only one side (superficial zone) of the cartilage disk. The chamber was treated with Casein to block non-specific binding of solutes to chamber surfaces. The equilibrated cartilage disks were then cut into halves and placed in the middle of the 'slot chambers' of the fixture. The chamber side facing the superficial zone was filled with ~45 µl of solute-PBS solution; the other side was filled with 1×PBS alone. The fixture was then placed in a petri dish containing DI water, covered, and placed on a slow-speed rocker inside the incubator to minimize stagnant layers at cartilage surfaces. After 24 h, the disks were then removed from the bath, gently rinsed in 1×PBS, and wiped to remove any particles stuck to the sample surfaces. A slice was cut from the center of the sample and imaged using a confocal microscope (Nikon TE2000-U) at 10× magnification. Filters were chosen to eliminate autofluorescence from the cartilage at the gains used for imaging. To ensure proper image comparison, solute concentrations were chosen such that the FITC concentration in each solution was identical. For desorption studies, the solute/particle solution was removed from the chamber and replaced with PBS.

Results

Figure 2B:
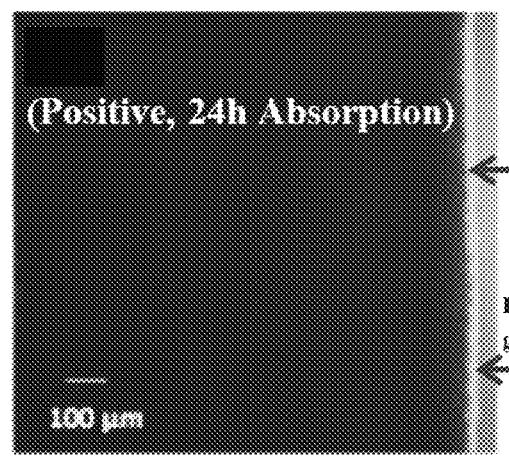
Figure 2C:
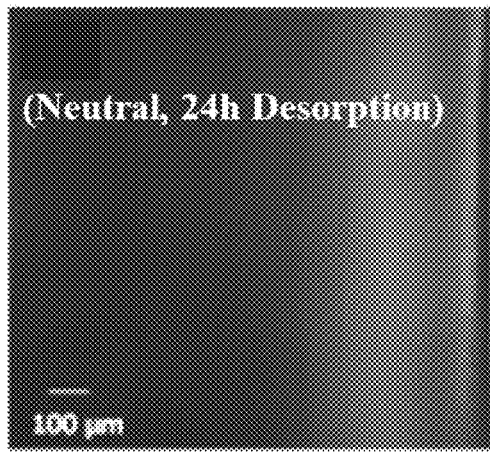
Figure 2D:
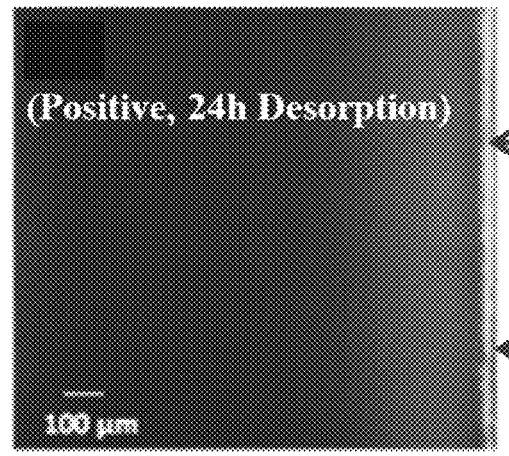
Figure 3D:
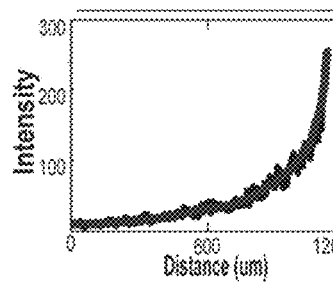

The right edge of confocal images used to generate FIGS. 2A and 2B showed that the 15 nm QDs entered the cartilage superficial zone and penetrated only through the first 40-50 µm of tissue. FIGS. 2C and 2D show desorption of QDs from these same samples after 24 h incubation in 1×PBS. Neutral QDs diffused out of the sample while charged QDs did not. Diffusion of FITC-dextran (300 Da, 8 kDa, & 40 kDa) into and through bovine cartilage explants occurred over 24 h. Size-dependent transport was observed: 300 Da FITC penetrated quickly throughout the tissue while a penetration gradient was evident for the 40 kDa FITC-dextran. Various penetrating depths of FITC-dextran (40 kDa) at 24 h, 48 h, and 96 h. FIGS. 5A, B show intensity normalized by the surface area of the sample (i.e., area under the curves), further clarifying the observed trends.

Discussion

The results showed that while solutes with MW~40 kDa (diam~10 nm) penetrated and diffused through a major part of the 1 mm thick bovine explant in 4 days, the particles with diameter 15 nm were only able to penetrate through the first 40-50 µm of the superficial zone in 6 days. This indicates that 15 nm diameter may be too large to penetrate through the complex meshwork of cartilage. Results also showed that the neutral particles desorbed in 1×PBS while the positively charged particles did not. The findings further indicated that a nanoparticle diameter of <10 nm may allow for nanoparticles to penetrate through the thickness of cartilage. In-vivo clearance issues associated with smaller sized particles may define a cut off size limit for the smallest practical particle. This indicates that polymeric particles ~10 nm may penetrate and diffuse into and through the tissue. As they gradually degrade, they may release functionalized drugs contained within or bound to their surface. An ideal size range is 7-10 nm.

The drugs themselves may have binding properties that enable them to bind reversibly within the cartilage matrix. This approach is sometimes herein referred to as the "Free Diffusion of Nanoparticles (FDN)."

In another approach disclosed herein, particles may be enabled to first bind within the surface layers (superficial zone) of the cartilage as demonstrated by the QD data (FIG. 2). As the particles gradually degrade, they may release the drugs, providing a sustained drug release over a period of time. Due to the much lower MW (~kDa) of the drugs, they may diffuse throughout the thickness of the cartilage tissue. This approach is sometimes herein referred to as the "Surface Binding of Nanoparticles (SBN)."

Example 4

Avidin as a Model for Charge Driven Transport into Cartilage: Relevance to Post-traumatic Osteoarthritis Drug Delivery Materials and Methods Introduction: In a series of transport studies, cartilage disks were incubated in medium containing a range of fluorescently tagged solutes of varying size and charge. Cross-sections of the cartilage were then imaged using confocal microscopy to determine the depth of penetration and the spatial distribution of each solute type within the tissue. In separate experiments to obtain a measure of total solute uptake, cartilage disks were equilibrated in solutions of selected solutes and then desorbed into phosphate buffered saline (PBS) baths. The measured fluorescence in the absorption and desorption baths were used to quantify the equilibrium solute uptake ratio, solute partition coefficient, and equilibrium binding properties of these solutes within the tissue. Additional studies of non-equilibrium transport through cartilage disks enabled estimation of the effective diffusivity of selected solutes within cartilage.

Bovine Cartilage Harvest and Culture

Cartilage disks were harvested from the femoropatellar grooves of 1-2 week old bovine calf knee joints (obtained from Research 87, Hopkinton, Mass.) as described previously (Patwari et al., Arthritis Rheum, 2003). Briefly, cylindrical cartilage disks (3 mm or 6 mm diameter) were cored using a dermal punch and then sliced to obtain the top 1 mm of cartilage with intact superficial zone. Cartilage disks for all treatment groups were matched for depth and location along the joint surface. The disks were then pre-equilibrated in PBS (without $Ca^{2+}/Mg^{2+}$) supplemented with protease inhibitors (Complete Protease Cocktail tablet in 50 mL PBS, Roche Applied Science, IN) in a 37° C., 5% $CO_2$ incubator for 24-48 h.

Solutes Types

Size exclusion studies: Solutes were used having a wide range of sizes from ~0.9 nm to 15 nm diameter: (i) fluorescein isothiocyanate (FITC, MW 389.3 Da, diam~0.9 nm), (ii) FITC-dextran (8 kDa, hydrodynamic diameter 4.3 nm), (iii) FITC-dextran (40 kDa, diameter~10 nm (all from Sigma Aldrich, MO); (iv) FITC-conjugated NeutrAvidin, an electrically neutral globular protein at pH 7 (60 kDa, diameter~7 nm; Invitrogen, CA) and (v) Cd—Se Quantum Dots 15 nm in diameter (synthesized at MIT (Liu et al., J Am Chem Soc, 2010)).

Binding/Retention studies: Effects of electrostatic interactions on solute transport, uptake and binding were investigated by using (i) FITC-conjugated and non-labeled Avidin (pI 10.5, 66 kDa, diameter~7 nm, Invitrogen, CA), the positively charged counterpart of NeutrAvidin, and (ii) amine functionalized 15 nm diameter Cd—Se quantum dots (QDs) (Invitrogen, CA, USA). FITC-dextran (8 kDa) was dialyzed using 1 kDa MW cut off dialysis tube (Float-A-Lyzer G2, SpectrumLabs Inc., CA) and all other solutes were dialyzed using 3 kDa cutoff MW centrifugal filter (Amicon Ultra-4, Millipore Corp, MA) to determine the amount of free FITC; the fluorescence readings of these solutions after dialysis indicated negligible amounts of free FITC. The solute types with their physical properties are listed in Table 1.

TABLE 1

Solute types and their physical properties

| Solute | Average Molecular Weight (Da) | Hydrodynamic diameter (nm) | Electric Charge in solution | Molecular Structure | References |
|---|---|---|---|---|---|
| Fluorescein Isothiocyanate (FITC) | 389.3 | 0.8-0.9 | Negative | Rigid molecule | (Moeini, Soft Matter, 2012) Sigma Aldrich |
| 8 kDa FITC-Dextran | 8000 | 4-4.3‡ | Negative | Polysaccharide, expandable coil | Sigma Aldrich |
| 40 kDa FITC-Dextran | 40,000 | 9-10‡ | Negative | Polysaccharide, expandable coil | Sigma Aldrich |
| Avidin-FITC | 66,000* | 7 | Positive | Globular protein; tetrameric structure; glycosylated | Invitrogen |
| NeutrAvidin-FITC | 60,000* | 7 | Neutral | Globular protein; tetrameric structure; non-glycosylated | Invitrogen |
| Green Cd—Se Quantum Dots | X | 15 | Slight Positive | Spherical; Cd—Se core functionalized with amine-derivatized PEG | (Liu et al., J Am Chem Soc, 2010) Invitrogen |

TABLE 1-continued

Solute types and their physical properties

| Solute | Average Molecular Weight (Da) | Hydrodynamic diameter (nm) | Electric Charge in solution | Molecular Structure | References |
|---|---|---|---|---|---|
| Red Cd—Se Quantum Dots | X | 15 | Neutral | Spherical; Cd—Se core functionalized with PEG | (Liu et al., J Am Chem Soc, 2010) |

*MW of the tetrameric structure
‡Hydrodynamic diameter in free solution when dextran is coiled (Moeini, Soft Matter, 2012)

Transport Configuration for Confocal Microscopy Imaging

A special poly(methyl methacrylate) (PMMA) transport chamber was designed to study one-way diffusion of solutes entering into cartilage from the tissue's superficial zone (SZ) (i.e., transport in the X direction in FIG. 1). The chamber walls were treated with casein to block non-specific binding of solutes to PMMA surfaces. Pre-equilibrated cartilage disks (6 mm diameter, 1 mm thick) were first cut in half, and the half-disk specimens were placed within holding slots machined into the chamber (FIG. 1A). The upstream chamber side facing the superficial zone was filled with 45 µl of a known concentration of solute in 1×-PBS solution supplemented with protease inhibitors (Roche Applied Science, IN); the downstream chamber side was filled with 45 µl of 1×-PBS containing protease inhibitors alone. The chamber was then placed in a petri dish containing DI water, covered (to minimize evaporation), and placed on a slow-speed rocker inside an incubator at 37° C. to minimize stagnant layers at cartilage surfaces.

Figure 3E:
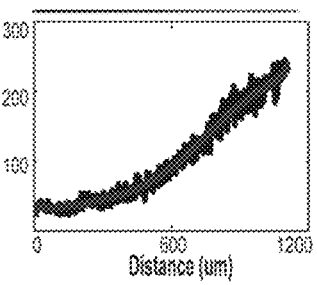
Figure 3F:
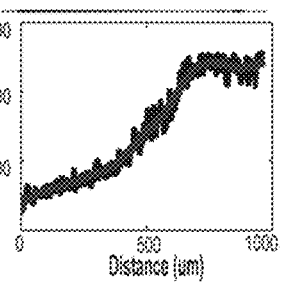

After 24-96 h, the cartilage half-disks were removed from the bath, gently rinsed in 1×PBS, and surface fluid along with any non-absorbed solutes were gently removed with Kimwipes. Using a scalpel, a slice (100-200 µm thick) was then cut from the center of each disk (FIG. 1B). The middle region of the slice (shown by the dotted boundary) was imaged in the X-Y plane using a confocal microscope (Nikon TE2000-U) at 10× magnification to identify the penetration and X-directed solute concentration profile within the tissue. Appropriate filters were chosen to eliminate auto-fluorescence of cartilage at the settings used for imaging. For desorption studies, the solute solution was removed from the chamber of FIG. 1 and replaced with 1× or 10×PBS containing protease inhibitors. To ensure proper image comparison, solute concentrations were chosen such that the FITC concentration in each solution was identical, thereby giving equal fluorescence intensities. Nominal concentrations for the absorption baths were 2.5 µM (FITC), 125 µM (FITC-dextran, 8 kDa), 25 µM (FITC-dextran, 40 kDa), 18 µM (Avidin), and 30 µM (NeutrAvidin). 100 µM (FITC-Dextran, 40 kDa) was also used for a separate 24-96 h transport study (FIG. 3D-F). The concentrations for the two types of QD solutions were chosen such that they exhibited equal fluorescence intensity.

Quantitative Analysis of Solute Uptake into Cartilage

Quantum Dot Uptake using Induced Coupled Plasma Measurement: The total uptake of QDs into cartilage half disks was measured via quantification of the amount of cadmium ($^{111}$Cd) present in the tissue and the absorption/desorption baths that were collected immediately after each QD uptake experiment. (Cd is present in the core of QDs). Inductively coupled plasma-mass spectrometry (ICP-MS) was performed using a ULTIMA 2 ICP Mass Spectrometer (Horiba Scientific, NJ) to quantify the amounts of $^{111}$Cd using a previously published method (Wong et al., PNAS, 2011). The sum of final amounts of Cd in the bath and the cartilage half disks corresponded to the initial amount of Cd in the starting 45 µl of QD-PBS upstream solution. The Cd amounts were converted into QD concentrations using calibration plots made for each QD studied. The background amount of Cd in fresh, untreated cartilage was measured to be zero.

Equilibrium Uptake of Avidin and NeutrAvidin: 3 mm diameter, 1 mm thick cartilage explants were incubated for specific times in 300 µl of known concentration (3 µM) of FITC-Avidin and FITC-NeutrAvidin, supplemented with protease inhibitors at 37° C. in a 96 well plate format. After removal from the absorption baths, the disks were rinsed, gently wiped and then incubated in 1× or 10×PBS supplemented with protease inhibitors for 24 h or longer as specified. At the end of the experiment, the surfaces of each disk were quickly blotted with Kimwipes and the wet weight was measured. The disks were then lyophilized and the dry weight was measured; the water weight was calculated from the tissue wet and dry weights. The fluorescence signal in the absorption and desorption baths was quantified using a plate reader (1400 Wallace Victor, PerkinElmer, MA); the solute content inside the cartilage disk was determined from the difference between the fluorescence reading of the absorption/desorption baths before and after incubation. In establishing standard curves, the fluorescence intensities and solute concentrations for both FITC-Avidin and FITC-NeutrAvidin were found to be linear with bath concentration. The solute uptake ratio was calculated as the concentration of the FITC-solute in the cartilage (per intra-tissue water weight) normalized to the concentration of FITC-solute in the equilibration bath.

Effect of sGAG Depletion on Solute Uptake

To understand the effects of the negatively charged glycosaminoglycan (GAG) chains within cartilage matrix on solute uptake and binding, groups of cartilage disks (3 mm diameter, 1 mm thick) were treated with either chondroitinase-ABC (Sigma Aldrich, MO, USA), or trypsin (Invitrogen, CA). Chondroitinase-ABC digests and removes GAG chains (predominantly the chondroitin sulfate GAG chains of the highly abundant aggrecan proteoglycans in cartilage) while the protease, trypsin, cleaves the core proteins of aggrecan and other GAG-containing proteoglycans and glycoproteins. However, both treatments leave cartilage's collagen network intact (Liotta et al., Proc Natl Acad Sci, 1979). The dimethyl-methylene blue (DMMB) dye binding assay (Farndale et al., Biochim Biophys Acta, 1986) was used to quantify the content of sulfated GAG (sGAG) remaining in the disks after enzyme treatment as well as that lost to the medium as previously described (Lu et al., Arthritis Research & Therapy, 2011), and the percentage of GAG removed by specific enzyme treatments was thereby calculated. For one series of experiments, a 24 h chondroitinase-ABC treatment (0.1 U/ml in 0.15 M NaCl, 0.05 M Na phosphate, pH 7.2 for 24 h at 37° C.) was used, resulting in 38.6% (~40%) depletion of sGAG, primarily from the outer tissue surfaces, which mimics the initial GAG loss caused by traumatic joint injury in vivo (Lotz et al., Arthritis Research & Therapy, 2010) and in models of cartilage injury in vitro (Bendele et al., J Musculoskelet Neuronal Interact, 2001). A second group of disks was treated with trypsin (1 mg/ml, in 0.15 M NaCl, 0.05 M Na phosphate, pH 7.2 for 24 h at 37° C.). Previous studies showed that treatment of similar bovine calf cartilage disks with 1 mg/ml trypsin caused nearly complete loss of measureable sGAG by 24 h (Bonassar et al., Arthritis Rheum, 1995). After enzyme treatments, the disks were washed three times in fresh PBS. Uptake experiments were then conducted using solute-PBS solutions containing protease inhibitors to minimize any additional protease activity. The transport and binding properties were then compared with that in the normal cartilage.

Transport Measurements for Effective Diffusivity

Real-time measurement of diffusive transport of Avidin and NeutrAvidin through young bovine cartilage disks (with intact superficial zone) was measured using a diffusion chamber consisting of two compartments as described previously (Garcia et al., Arch Biochem Biophys, 2003). Groups of three cartilage disks (6 mm diameter, 400 μm thick) were clamped by O-rings between the two compartments of the diffusion chamber (with total exposed tissue area for transport of 0.28 $cm^2$/disk), such that solute transport from the upstream compartment into and across the cartilage disks, simultaneously, could occur only from the superficial zone of the cartilage (schematic shown in the inset of FIG. 14). The compartments were treated with casein to prevent non-specific adsorption of solutes to the chamber surfaces. Each compartment was then filled with 25 ml of 0.15 M NaCl with protease inhibitors and maintained at 20° C. At starting time t=0, FITC tagged Avidin or NeutrAvidin was added to the 'upstream' compartment, resulting in transport through the tissue into the downstream compartment. The baths in both compartments were magnetically stirred to minimize the effects of stagnant layers at the solution-tissue interfaces. Aliquots were taken from each chamber at different time intervals, and fluorescence was measured using a plate reader.

Figure 14:
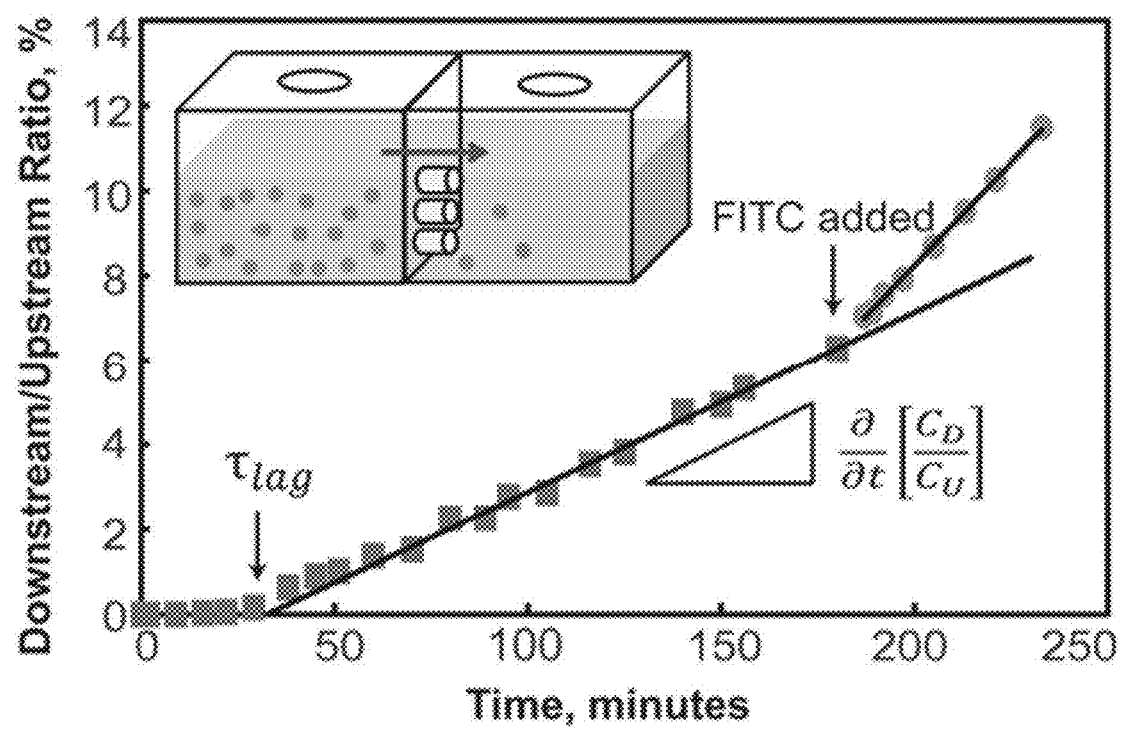
FIG. 14 depicts non-equilibrium diffusive transport of Avidin-FITC across a group of three 6 mm diameter, 400 µm thick cartilage explants, plotted as the measured downstream concentration versus time, normalized to the applied upstream concentration. At t=0 min, Avidin-FITC was added to the upstream chamber. The effective diffusivity was calculated from $\tau_{lag}$ and the steady state diffusivity from the measured diffusive flux of Avidin-FITC (i.e., the slope of the concentration versus time). At t=186 min, free FITC was added to the upstream chamber to estimate the contribution of unbound FITC to the total flux.

The compartment volume of 25 ml is approximately 1,000× larger than the volume of the cartilage plugs in the configuration of FIG. 14 (inset). As a result, the boundary solute concentration at the cartilage-solution interfaces, both upstream and downstream, remained to within ~5% of their starting (t=0) values throughout the course of these transport experiments. This configuration thereby focuses on quantitation of steady state solute flux and assessment of effective solute diffusivity within cartilage. In contrast, the transport chamber compartment volumes in the configuration of FIG. 1 are relatively smaller and closer to the volume of the cartilage disks, a configuration that more closely approximates the relative solid-fluid volumes of cartilage and adjacent synovial fluid in joints in vivo. (For example, human tibial plateau cartilage volume is ~4 ml (Adam et al., J Anat, 1998), and knee joint synovial fluid volume ranges from ~1-4 ml (Huffman et al., Rheumatology, 2007).

Statistical Analysis

Figure 4A:
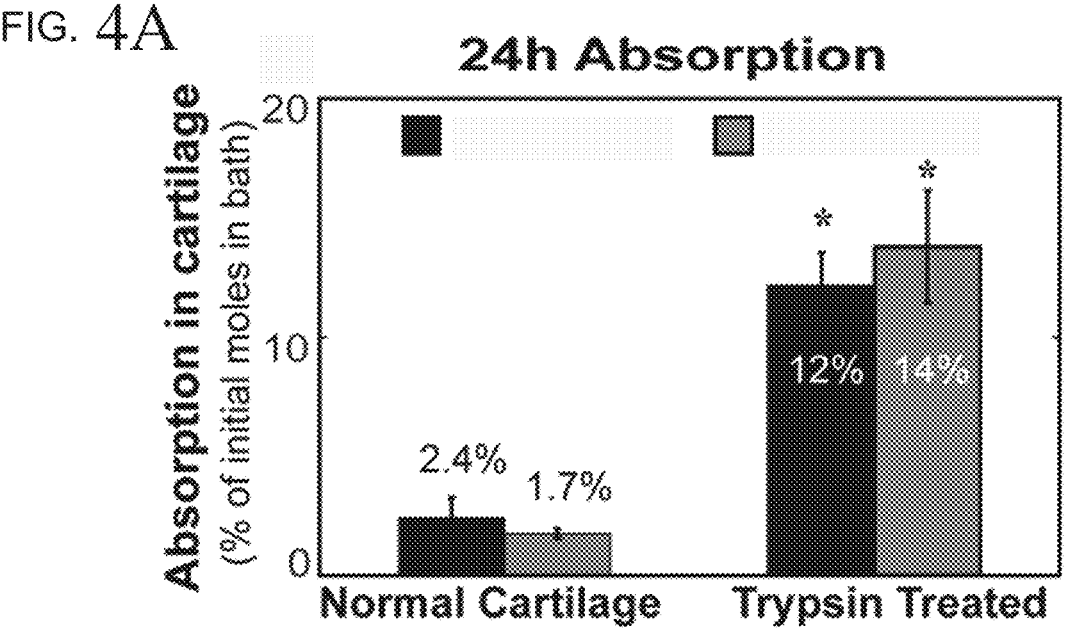
FIGS. 4A and 4B involve analysis of the concentration profile inside normal cartilage explants of 15 nm in diameter. Non-functionalized Cd—Se QDs was measured after 24 h absorption and 24 h desorption (into 1×PBS bath). The concentration profile inside normal cartilage explants of 15 nm amine functionalized QDs was also assessed after 24 h absorption or 24 h desorption (into 1×PBS bath). The concentration profile of 15 nm non-functionalized QDs inside trypsin treated cartilage explants (1 mg/ml, 24 h treatment) after 24 h absorption or 24 h desorption (into 1×PBS bath) was assessed.
Figure 4B:
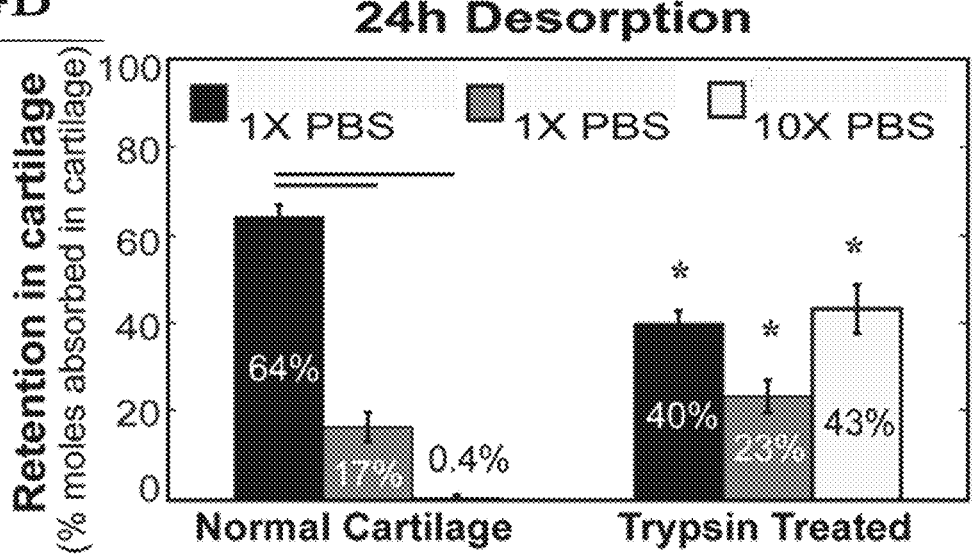

Data on solute uptake and desorption (e.g., FIGS. 4A-B and 12A-C) are presented as Mean±SEM. The general linear mixed effects model with animal was used as a random variable for analysis followed with the Tukey's test for comparisons between multiple treatment conditions. FIG. 4 data are derived from 2 different animals. A total of n=3 cartilage samples per animal in each treatment condition were used. The mean represents the average of 6 samples per treatment condition, as there was no effect of animal. FIG. 12 data were derived from 3 different animals for the normal cartilage condition and 1 animal for the 40% GAG depleted condition. A total of n=6 cartilage samples per animal in each treatment condition was used; the mean represents the average of 18 samples per treatment for the normal cartilage condition (since there was no effect of animal) and the average of 6 samples per treatment for the 40% GAG depleted condition. We used p<0.05 for statistical significance.

Results

Figure 3G:
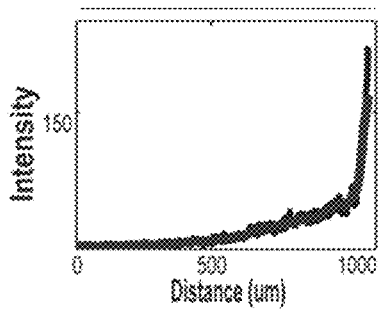
Figure 3H:
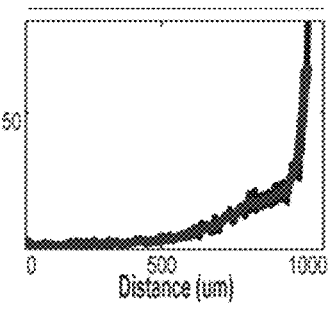
Figure 3I:
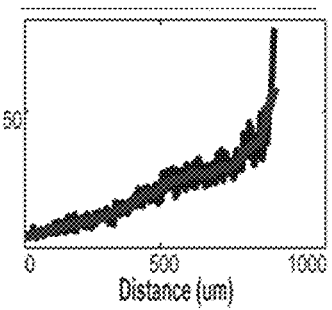

Effect of Solute Size and Molecular Structure on Transport into Cartilage:

Transport studies with FITC (389 Da, diameter~0.9 nm) and FITC-dextran (8 kDa, diameter~4.3 nm) showed that particles with hydrodynamic diameter<5 nm penetrated throughout the full thickness (1 mm) of the cartilage explant within 24 h, while a penetration gradient was still evident at 24 h for 40 kDa FITC-dextran (diameter~10 nm) (FIG. 3A-C). The relative fluorescence intensity vs. penetration distance into cartilage is shown, illustrating size-dependent transport. 40 kDa FITC-dextran solutes (expandable polysaccharide coil) diffused into the major part of the cartilage thickness in 4 days (FIG. 3D-F), while the globular protein, NeutrAvidin (MW 60 kDa, diameter~7 nm) penetrated approximately half the sample thickness (FIG. 3G-I). 15 nm diameter QDs were trapped in the cartilage superficial zone and penetrated only the first 40-50 μm of tissue in 24 h. The penetration depth of these QDs did not change even by 6 days (data not shown), suggesting that 15 nm diameter particles are too large to penetrate through the complex meshwork of cartilage matrix. However, trypsin treated samples allowed the 15 nm QDs to penetrate through the full thickness of the cartilage disk in 24 h. FIGS. 5A, B show fluorescence intensity normalized by the surface area of the sample (i.e., area under the curves), further clarifying the observed trends. FIG. 5A. FITC (300 Da), FITC-Dextran (8 kDa & 40 kDa) in 24 h and FIG. 5B. for FITC-Dextran (40 kDa) at 24 h-96 h.

Effect of Particle Surface Properties on Uptake, Retention and Binding within Cartilage:

Amine functionalized QDs did not desorb after 24 h in 1×PBS while the QDs with no functional group did. Desorption in 10×PBS significantly reduced the retention of QDs in the cartilage disks from 64% to 0.4% of the absorbed amount in 24 h (FIG. 4B). Trypsin treated samples exhibited significantly lower retention (~40%) compared to normal cartilage (~64%) but retained similar amounts with 1× and 10× desorption (FIG. 4B), suggesting charge based interactions. Matrix degradation due to trypsin treatment significantly enhanced the penetration and uptake for both types of QDs, as expected (FIG. 4A).

To further explore the effects of electrostatic interactions, the transport and binding properties of Avidin (a highly positively charged globular protein) were compared to that of its neutral counterpart, NeutrAvidin. Despite their similar sizes, NeutrAvidin penetrated only half the specimen thickness in 4 days (mean uptake~0.44) while Avidin diffused through the full thickness of the cartilage (mean uptake~183) within 1 day, resulting in greater than 400 times higher uptake of Avidin compared to NeutrAvidin (FIG. 11A-C; 12A and 12B). About 50% of the absorbed NeutrAvidin diffused out of the cartilage within 1 day in 1×PBS, while 96% of the absorbed Avidin remained inside the cartilage even by 15 days (the duration of the experiment conducted) in 1×PBS (FIG. 12C). However, a significantly higher percent (~69%) of the absorbed Avidin diffused out of the cartilage in 10×PBS within 24 h, suggesting effects of strong electrostatic interactions. It was held that the Avidin could be binding (reversibly) to the negatively charged GAG chains in the cartilage matrix. Depletion of 40% of the cartilage sGAG (using chondroitinase-ABC) resulted in significantly reduced uptake of Avidin over a 24 h period, from a mean value of 183 in normal cartilage to 24 in GAG-depleted tissue (FIG. 12A). This further confirmed the effects of charge interactions and showed that the negatively charged sGAG chains of cartilage matrix play a critical role in enhancing the transport, uptake and binding properties of large, positively charged globular proteins like Avidin. The uptake of NeutrAvidin, however, increased from 0.28 in the normal cartilage to 0.55 in GAG depleted cartilage by 24 h (FIG. 12B), which may be due to the increase in the matrix pore size resulting from 40% sGAG depletion.

Avidin Uptake as a Function of Bath Avidin Concentration:

The results shown in FIG. 12, found that Avidin may bind to sites within the cartilage. To test this hypothesis, competitive binding experiments were performed in which 3 mm diameter cartilage disks were equilibrated for 3 days in 300 µl buffer containing a fixed amount of (fluorescently labeled) FITC-Avidin (1 µM) and graded amounts of unlabeled Avidin (0, 10, 76, 100, and 203 µM). The disks were split into half disks to reduce the time needed for equilibration, which was performed in 96 well plates at 37° C. The uptake ratio, $R_U$, was measured and plotted versus the total bath concentration of Avidin (labeled+unlabeled, FIG. 13), where $R_U$ is defined as the total concentration of Avidin inside the cartilage (bound ($C_B$) plus free ($C_F$)) per intra-tissue water weight, normalized to the Avidin concentration in the equilibration bath ($C_{Bath}$):

$$R_U = \frac{C_B + C_F}{C_{Bath}} \quad (1)$$

Figure 13:
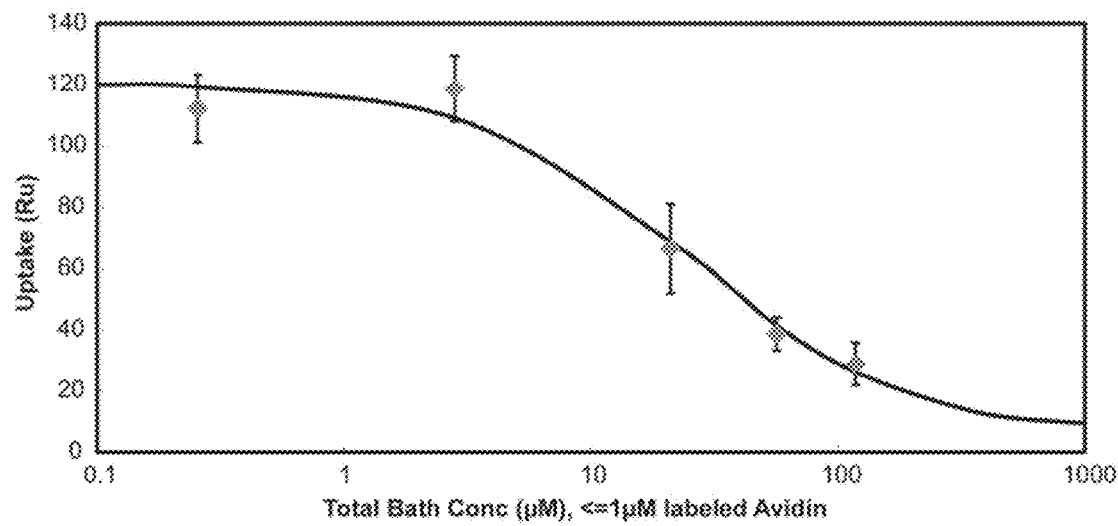
FIG. 13 depicts the concentration dependent uptake ratio of FITC labeled Avidin in cartilage explants after 3 day equilibration at 37° C. in 1×PBS supplemented with protease inhibitors. Graded amounts of unlabeled Avidin was added to a fixed amount of FITC-Avidin (<1 µM). The theoretical curve of Equation (5) (solid line) was fit to the data to obtain best-fit values of K, $K_{EQ}$, and $N_T$. The predicted values are K~6, $K_{EQ}$~150 µM and $N_T$~3000 µM. Total bath Avidin concentration is the sum of labeled and unlabeled Avidin. Data are mean±SD, n=4 disks per condition.

Labeled and unlabeled Avidin were held to partition into the cartilage identically. At very low concentration of the labeled Avidin (≤1 µM), a high uptake of ~120 was observed. When unlabeled Avidin was added to the bath, both species (labeled and unlabeled) could compete for the same (constant) number of binding sites available in the tissue (site density $N_T$). As the concentration of unlabeled Avidin was increased, the uptake of labeled Avidin was observed to decrease dramatically (FIG. 13). To model the data of FIG. 13, a first-order, bimolecular, reversible reaction was produced to describe binding of Avidin to a single dominant binding species within cartilage. A theoretical model was adopted, (Garcia et al., Arch Biochem Biophys, 2003) previously used for characterizing the binding of soluble insulin like growth factor-1 (IGF-1) to IGF-binding proteins (IGF-BPs) that are uniformly enmeshed and fixed within cartilage matrix. According to this model, the equilibrium molar concentration of free solute ($C_F$), bound solute ($C_B$), intra-tissue binding site density ($N_T$) and the equilibrium dissociation constant ($K_{EQ}$) are related by the binding isotherm:

$$\frac{C_B}{C_F} = \frac{N_T}{K_{EQ} + C_F} \quad (2)$$

which is similar in form to a Langmuir adsorption isotherm. In addition, the equilibrium partition coefficient (K) of solute, Avidin, is defined as the concentration of the free solute inside the cartilage disk (per intra-tissue water weight) normalized to the concentration of solute in the bath:

$$K = \left(\frac{C_F}{C_{Bath-final}}\right)_{unlabeled\ Avidin} = \left(\frac{C_F}{C_{Bath-final}}\right)_{FITC-Avidin} \quad (3)$$

In these experiments, the final Avidin bath concentration in Equation (3), $C_{Bath-final}$, is generally different from the initial bath concentration, $C_{Bath-initial}$, because of the very high uptake of Avidin into cartilage. The ratio of final to initial Avidin bath concentration is defined as f:

$$\left(\frac{C_{Bath-final}}{C_{Bath-initial}}\right)_{FITC-Avidin} = \left(\frac{C_{Bath-final}}{C_{Bath-initial}}\right)_{unlabeled} = f$$

Then the partitioning of labeled and unlabeled Avidin into cartilage then becomes:

$$C_F = KfC_{Bath-initial} \quad (4)$$

Combining Equations 1-4 yields:

$$R_U = K\left(1 + \frac{N_T}{K_{EQ} + KfC_{Bath-initial}}\right) \quad (5)$$

Figure 15:
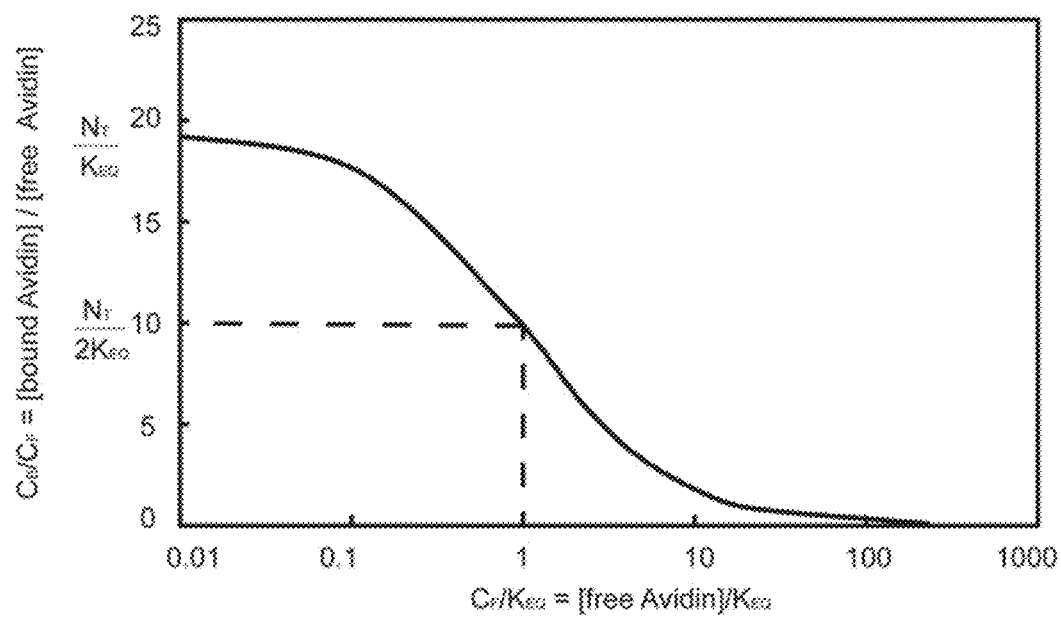
FIG. 15 depicts the competitive binding of fluorescently labeled Avidin to intratissue sites in cartilage. The data of FIG. 13 are re-plotted in the format of the binding isotherm of Eq. (2).

The theoretical curve for $R_U$ was fit to the data of FIG. 13 (solid line) using nonlinear least squares; the best fit values for the three unknown parameters were, K=5.9, $K_{EQ}$=150.3 µM and $N_T$=2920 We note that the partition coefficient K is the value of $R_U$ in Eq. (5) in the limit of very high Avidin bath concentration (i.e., the limit in which all the binding sites are occupied by the unlabeled Avidin). Thus, K is determined by both steric hindrance and electrostatic (Donnan) interactions. (The data of FIG. 13, re-plotted in the form of the binding isotherm of Eq. (2), is presented in FIG. 15.

Characterization of Non-equilibrium Transport of Avidin Across Bovine Cartilage:

The transport cell arrangement shown in the inset of FIG. 14 was used to measure transient transport of Avidin and NeutrAvidin into and across cartilage disks. FIG. 14 shows real time measurements of the downstream concentration of FITC-Avidin (normalized to upstream concentration) that had diffused through a group of three cartilage explants in parallel. Extrapolation of the linear slope of concentration versus time (between t=50 to t=150 minutes) to the time axis gives the time lag $\tau_{lag}$ to achieve the steady state flux (Crank et al., Clarendon Press, 1975) which, for Avidin, was $\tau_{lag}$~35 min. This $\tau_{lag}$ is related to the effective diffusivity, $D_{EFF}$, of Avidin that characterizes the initial transport transient (Crank et al., Clarendon Press, 1975):

$$\tau_{lag} = \frac{\delta^2}{6\ D_{EFF}} \quad (6)$$

where δ is the thickness of the cartilage disk (~400 µm). $D_{EFF}$ for Avidin was calculated to be 3.8×10⁻⁷ cm²/s. It was held that this time lag and, hence, $D_{EFF}$ may be associated in part with the effects of binding of Avidin within the cartilage. Once this binding has reached steady state, a corresponding steady state flux would be achieved, as seen in FIG. 14 from t=35 min to t=186 min. This steady state flux is expressed in terms of the steady state diffusivity $D_{SS}$ by:

$$\Gamma = \Phi K D_{SS} \frac{C_U - C_D}{\delta} \cong \Phi K D_{SS} \frac{C_U}{\delta} \quad (7)$$

where $\Phi$ is the tissue porosity (measured from wet and dry weights to be $\Phi$=0.81), K is the partition coefficient, and $C_U$ and $C_D$ are upstream and downstream bath concentrations, respectively. The time derivative of the normalized downstream concentration (slope) is related to the steady state flux by, $$\frac{\partial}{\partial t}\left(\frac{C_D}{C_U}\right) = \frac{\Gamma A}{V_D C_U} \cong \frac{\Phi K D_{SS} A}{\delta V_D} \quad (8)$$

where A is the total exposed tissue area (0.84 cm$^2$) and $V_D$ (25 cm$^3$) is the volume of the downstream bath. Using Eq. 8, the product $KD_{SS}$ for Avidin was calculated to be $1.4 \times 10^{-5}$ cm$^2$/s. Similarly, $KD_{SS}$ for NeutrAvidin was calculated to be $2.3 \times 10^{-6}$ cm$^2$/s, giving a ratio of $(KD_{SS})_{Avidin}$ to $(KD_{SS})_{NeutrAvidin}$ of ~10. Avidin and NeutrAvidin are of similar size and, hence, are expected to have similar steady state diffusivity, $D_{SS}$. The partition coefficient for NeutrAvidin, $K_{NeutrAvidin}$ was estimated from the data of FIG. 12B to be 0.44. Using these values, we calculated $K_{Avidin}$ to be 4.4 and $D_{SS}$ to be $3.2 \times 10^{-6}$ cm$^2$/s.

To test whether any unbound FITC was present which could affect the measurement of the total flux and thereby the estimate of diffusivity, free FITC (MW 389) was added at t=186 min into the upstream bath. Almost immediately, the diffusive flux of fluorescently labeled species across the cartilage increased dramatically (FIG. 14). The diffusivity of free FITC was thereby estimated to be $2.8 \times 10^{-5}$ cm$^2$/s, one order of magnitude higher than the steady state diffusivity ($D_{SS}$) calculated for Avidin, implying that there was a negligible amount of free FITC present which could affect the measurement of the flux of FITC-Avidin.

Assuming that $D_{EFF}$ includes the effects of binding, modeled using first order, reversible bimolecular reaction kinetics, $D_{EFF}$ can be derived in terms of $D_{SS}$ (Garcia et al., Arch Biochem Biophys, 2003). During the initial addition of labeled Avidin, i.e., in the limit in which $C_F < K_{EQ}$, $D_{EFF}$ is related to $D_{SS}$ by (Garcia et al., Arch Biochem Biophys, 2003):

$$D_{EFF} \cong D_{SS}\left(1 + \frac{N_T}{K_{EQ}}\right)^{-1} \quad (9)$$

From the best fit values (section 3.2), $$\left[1 + \frac{N_T}{K_{EQ}}\right] = 20.4.$$

Using $D_{EFF}$~$3.8 \times 10^{-7}$ cm$^2$/s (from FIG. 14), $D_{SS}$=$7.7 \times 10^{-6}$ cm$^2$/s, which is on the same order of magnitude as that calculated from the transport cell experiment. (See Table 2 for transport properties estimated for Avidin.)

TABLE 2

Transport properties estimated for Avidin

| Avidin Transport Properties | Binding Isotherm | Transport cell |
|---|---|---|
| Partitioning, $K_{Avidin}$ | ~6 | ~4.4 |
| Binding density ($N_T$) | ~2920 μM | X |
| Dissociation Constant ($K_{EQ}$) | ~150 μM | X |
| Effective Diffusivity ($D_{EFF}$) | X | $3.8 \times 10^{-7}$ cm$^2$/s |
| Steady State Diffusivity ($D_{SS}$) | $7.7 \times 10^{-6}$ cm$^2$/s | $3.2 \times 10^{-6}$ cm$^2$/s |
| | $D_{SS} = D_{EFF}\left(1 + \frac{N_T}{K_{EQ}}\right)$ | |
| Effective Charge | +6 | X |

Discussion

Traumatic joint injuries can result in damage to many soft and hard tissues. While joint cartilage sometimes remains undamaged, varying changes are observed, from subtle microdamage to the matrix (not visualizable by MRI or arthroscopy) up to overt fibrillation and cracks (Johnson et al., Am J Sports Med, 1998). Trauma simultaneously increases the levels of inflammatory cytokines in the synovial fluid, which can predispose even undamaged cartilage to rapid chondrocyte-mediated proteolysis and loss of aggrecan and other matrix molecules within the first days/weeks post-injury (Anderson et al., J Orthop Res, 2011; Lu et al., Arthritis Research & Therapy, 2011; Lotz et al., Arthritis Research & Therapy, 2010; Johnson et al., Am J Sports Med, 1998; Sui et al., Arthritis Rheum, 2009), eventually leading to PTOA. With the need to identify drug-carrying nanoparticles that can penetrate rapidly within cartilage to provide sustained delivery of drugs to cell and matrix targets throughout the tissue, a range of particle sizes and types were studied to test their ability for rapid and sustained uptake.

It was found that deep penetration into normal (undamaged) cartilage was achieved at particle diameters<10 nm (FIG. 3-4). If injected intra-articularly, in-vivo clearance would define a practical lowest size limit (Goldberg et al., J Biomater Sci Polym Ed, 2007; Wang et al., Biomaterials, 2010). While 15 nm diameter particles were sterically hindered and trapped in the superficial zone of normal cartilage, they could penetrate into the deeper zones of proteoglycan-depleted cartilage (FIG. 4), consistent with previous reports of solute penetration (Maroudas et al., J Anat, 1976; Snowden et al., Biochim Biophys Acta, 1976; Leddy et al., J. Biomed. Mater. Res., Part B, 2004; Greene et al., Biomaterials, 2008; Torzilli et al., J Biomech, 1997; Torzilli et al., J Biomed Mater Res Part A, 1998).

The high negative fixed charge density of cartilage offers the unique opportunity to utilize electrostatic interactions to augment transport, binding and retention of drug carriers. Recently, transport into cartilage explants of a small cationic peptide therapeutic was investigated (Arg-Tyr-Lys-Arg-Thr (SEQ ID NO: 7); 760 Da, net charge+3; pI=11). The concentration of the peptide was indeed higher in cartilage due to Donnan (electrostatic) partitioning (as would be expected), but the peptide did not bind within the cartilage and therefore rapidly diffused out (Byun et al., Arch Biochem Biophys, 2010). Reversible binding to intra-tissue sites is necessary to maintain enhanced intra-tissue concentration for sustained local delivery, and separate experiments must be performed for any given nanoparticle to test whether electrostatic interactions can simultaneously affect non-equilibrium transport and equilibrium uptake (the latter associated with binding of solutes to matrix and/or upward Donnan partitioning of unbound solutes into intra-tissue fluid).

It was found that that Avidin's structure, due to its size and high positive charge, exemplifies distinct advantages for a particle-based drug delivery system. Avidin penetrated throughout the full thickness of cartilage explants within 24 h, while the same-sized neutral counterpart, NeutrAvidin, took four days to penetrate into half the thickness (FIGS. 3, 11). Avidin showed a 400 times higher equilibrium uptake compared to NeutrAvidin in normal cartilage. Additionally, Avidin was retained within cartilage for at least 15 days, while NeutrAvidin was mostly released when explants were placed in a 1×PBS desorption bath for 24 h (physiological ionic strength) (FIG. 12). When placed in high salt (10× PBS), Avidin, too, was readily desorbed due to the shielding of electrostatic interactions.

The transport of a large, positively charged molecule like Avidin through negatively charged cartilage is influenced by three phenomena (i) steric hindrance from the dense tissue ECM (characterized by $D_{SS}$, Eq. (7)), (ii) binding to the intra-tissue sites (characterized by $D_{EFF}$, which is a function of $D_{SS}$, $N_T$, and $K_{EQ}$, Eq. (9)), and (iii) Donnan partitioning of unbound Avidin due to electrostatic interactions (characterized by K, Eqs. (3,7)). Upon initial addition of Avidin to the bath, electrostatic interactions results in high upward Donnan partitioning of Avidin at the solution-cartilage interface (through K). The resulting steep intra-tissue concentration gradient greatly enhances transient transport of Avidin into the tissue compared to that of similarly sized but neutral, NeutrAvidin, as observed (FIGS. 11, 12). At final equilibrium, the high uptake of Avidin could be due to either intra-tissue binding and/or tissue-wide upward Donnan partitioning. To distinguish between these effects, w additional competitive binding experiments were performed (FIG. 13) which show that Avidin binds weakly and reversibly to sites in cartilage with a $K_D$~150 µM. The predicted high binding site density ($N_T$~2920 µM) is consistent with the high concentration of intra-tissue GAGs, and explains Avidin's long retention time (~15 days) inside the tissue.

Further evidence of the presence of binding interactions was provided by the non-equilibrium transport experiments of FIG. 14: the measured diffusion lag time ($\tau_{lag}$) showed that binding slowed the initial transport of Avidin into cartilage compared with the final steady state diffusive transport across the tissue. The effective diffusivity $D_{EFF}$ (which includes the effects of binding from Eq. (9)) was estimated from the measured $\tau_{lag}$ (Eq. (6)); $D_{EFF}$ was an order of magnitude less than $D_{SS}$, the diffusivity after binding had reached steady state. Nevertheless, this weak, reversible binding did not inhibit Avidin's rapid penetration into the full depth of the explants because of the steep intra-tissue concentration gradient caused by Donnan partitioning.

Because of the importance of electrostatic interactions in the uptake and transport of Avidin in cartilage, several approaches were used to estimate the effective net charge of the Avidin tetramer responsible for the experimental observations presented. First, the amino acid structure of Avidin suggested a net tetrameric charge of +20 based on the net excess of basic over acidic residues.

Net charge was estimated by summing over the basic (lysine, arginine) and acidic (glutamic and aspartic acid) groups which can ionize at pH 7:

TABLE 3

Net charge of Avidin estimated from amino acid sequence

| Basic Groups per chain | | Acidic Groups per chain | |
|---|---|---|---|
| Lysine | +9 | Glutamic | −7 |
| Arginine | +8 | Aspartic | −5 |
| Total positive charge | +17 | Total negative charge | −12 |

Total charge per chain = +5
Tetrameric structure of Avidin → +5 × 4 = +20

However, it is not certain whether the effective charge sensed during transport and uptake would include all these residues, or whether certain residues may be internal and less accessible to charge-charge interactions within the cartilage extracellular matrix. In addition, the unknown extent of Avidin glycosylation may contribute additional net negative charge that would decrease the total net charge. However, this estimate assumes that all such residues are ionized in aqueous solution and that none of these residues are internal (buried) and thereby inaccessible to charge-charge interactions within the cartilage matrix. Furthermore, this estimate neglects the effects of Avidin glycosylation which could add additional negative charge groups to the total sum. For further confirmation of the accuracy of estimates, the Donnan equilibrium theory was applied to the experimental results of FIGS. 12B and 13 to calculate Avidin charge.

Net Charge of Avidin Estimated Using Donnan Equilibrium

With cartilage explants in equilibrium in a bath containing PBS and Avidin, Donnan equilibrium partitioning predicts the distribution of Avidin with charge z to be related to the concentration of Na$^+$ and Cl$^-$ inside the cartilage tissue:

$$\left(\frac{\overline{C}_{Avidin}}{K_{NeutrAvidin} C_{Avidin}}\right)^{\frac{1}{z}} = \frac{\overline{C}_{Na}}{C_{Na}} = \frac{C_{Cl}}{\overline{C}_{Cl}} \tag{10}$$

where $\overline{C}_{Na}$, $\overline{C}_{Cl}$ and $\overline{C}_{Avidin}$, are the intra-tissue concentrations of Na$^+$, Cl$^-$ and free (unbound) Avidin, respectively. $C_{Avidin}$, $C_{Na}$ and $C_{Cl}$ are bath concentrations of Avidin, Na$^+$ and Cl$^-$. The results of FIGS. 12B and 13 give the partition coefficients for Avidin and NeutrAvidin:

$$\frac{\overline{C}_{Avidin}}{C_{Avidin}} = K_{Avidin} \sim 6, K_{NeutrAvidin} \sim 0.44.$$

Since the bath was 1×PBS (i.e., physiological ionic strength), $\overline{C}_{Na}$ and $\overline{C}_{Cl}$~0.15 M. Also, bulk electroneutrality requires that the sum of all the charges inside the tissue is equal to zero:

$$\rho + F(\overline{C}_{Na} - \overline{C}_{Cl} + z\overline{C}_{Avidin}) = 0 \tag{11}$$

where ρ is the fixed charge density of cartilage and F the Faraday constant. Since Avidin is a minority carrier (~µM) compared to Na$^+$ and Cl$^-$, we can safely ignore $C_{Avidin}$ in Eq. (11). Thus, $$\frac{\rho}{F} + \overline{C}_{Na} - \frac{0.15^2}{\overline{C}_{Na}} = 0 \tag{3}$$

The fixed charge density for our femoropatellar groove cartilage from 1-2 week old bovine calves, $$\frac{\rho}{F}$$

(Byun et al., Arch Biochem Biophys, 2010) was measured to be, −0.13 M. Rearranging Eq. (12) gives:

$$z = \frac{\log\left(\frac{\overline{C}_{Avidin}}{K_{NeutrAvidin}C_{Avidin}}\right)}{\log\left(\frac{\overline{C}_{Na}}{C_{Na}}\right)}$$

The effective net charge, z, for Avidin was thereby computed to be ∼+6.2.

Donnan theory (Grodzinsky et al., New York: Garland Science, 2011) is based on the assumptions that (1) all freely moving charged species (i.e., Avidin and bath ions) will partition into a charged tissue according to Boltzmann statistics and, (2) the net charge in the tissue is zero by electroneutrality (i.e., the sum of the tissue fixed charge density and mobile carrier concentrations). By fitting the Donnan theory to the equilibrium uptake data of FIG. 12A, the effective net charge of Avidin was calculated to be +6.2. This value is very close to the effective charge of +7.3 that was obtained by using the reported zeta potential of Avidin (Dougherty et al., Langmuir, 2009) in the Grahame equation for spherical particle electrokinetics.

Net Charge of Avidin Estimated from Reported Electrokinetic Zeta Potential:

The zeta potential of Avidin molecules in dilute solution of DI water at pH 5 has been reported to be 10 mV (Dougherty et al., Langmuir, 2009). Using Grahame Equation of electrokinetics (Grodzinsky et al., New York: Garland Science, 2011) that related zeta potential to particle surface charge density, and assuming that Avidin attains a spherical shape (diameter∼7 nm), the zeta potential of 10 mV corresponds to an effective net molecular charge of ∼+7.3.

A final upper estimate of effective net charge was obtained by assuming that the uptake of Avidin in the experiments of FIG. 13 was entirely due to Donnan partitioning into cartilage in the complete absence of binding to intra-tissue sites. This estimate gave a net charge of +13 to +14.

Upper Bound Estimate of Avidin Charge:

The upper bound estimate of Avidin charge was next investigated, holding that Avidin uptake in FIG. 13 is due to electrostatic interactions (Donnan theory) and not binding Donnan equilibrium partitioning predicts the distribution of Avidin with charge z to be related to the concentration of Na⁺ and Cl⁻ inside the cartilage tissue as:

$$\left(\frac{\overline{C}_{Avidin}}{K_{NeutrAvidin}C_{AvidinBath\text{-}final}}\right)^{\frac{1}{z}} = \frac{\overline{C}_{Na}}{C_{Na}} = \frac{C_{Cl}}{\overline{C}_{Cl}} = r \rightarrow \overline{C}_{Avidin} = r^z K_{NeutrAvidin} C_{AvidinBath\text{-}final} = r^z K_{NeutrAvidin} f\, C_{AvidinBath\text{-}initial}$$ (13)

where $$f = \frac{C_{AvidinBath\text{-}final}}{C_{AvidinBath\text{-}initial}} \quad \text{(See Eqs. (3-4))}$$

It was held that the uptake of Avidin was entirely due to Donnan partitioning into cartilage in the complete absence of binding to intra-tissue sites i.e., all of Avidin inside the cartilage after equilibration is free. Avidin's uptake is defined as $R_u = K_{NeutrAvidin}\, r^z$.

Since the bath was 1×PBS (i.e., physiological ionic strength), $\overline{C}_{Na}$ and $\overline{C}_{Cl}$∼0.15 M, hence $$\overline{C}_{Cl} = \frac{0.15^2}{\overline{C}_{Na}} \text{ and } \overline{C}_{Na} = 0.15r$$ (14)

Also, bulk electro-neutrality requires that the sum of all the charges inside the tissue is equal to zero:

$$\rho + F(\overline{C}_{Na} - \overline{C}_{Cl} + z\overline{C}_{Avidin}) = 0$$ (15)

Using the measured value of $$\frac{\rho}{F}$$

as −0.13 and $K_{NeutrAvidin}$ as 0.44 from S2, rearranging Eqs. (13-15) gives:

$$-0.13 + 0.15r - \frac{0.15}{r} + 0.44zr^z f\, C_{AvidinBath\text{-}initial} = 0$$ (16)

Figure 16:
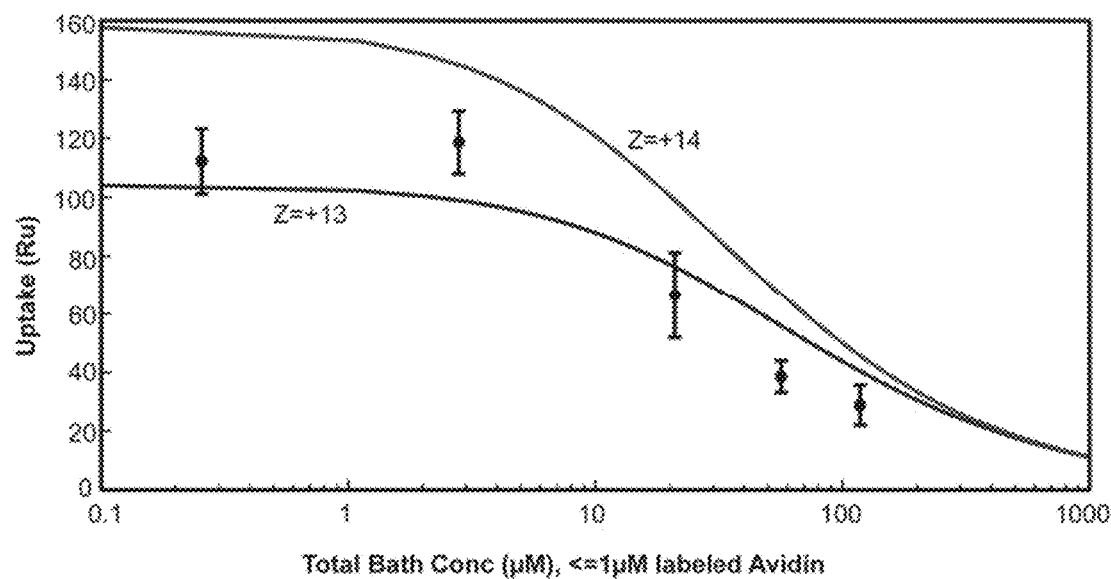
FIG. 16 depicts a best fit graph where Avidin's uptake, $R_u$ ($K_{NeutrAvidin} r^2$) is plotted on the Y axis and $C_{AvidinBath-final}$ on the X axis.

Z was varied for different values of $C_{AvidinBath\text{-}initial}$ and calculated r. The best fit was obtained for Z between +13 and +14 as depicted in the graph of FIG. 16. Avidin's uptake, $R_u$ ($K_{NeutrAvidin}\, r^z$) is plotted on the Y axis and $C_{AvidinBath\text{-}final}$ on the X axis.

The loss of the negatively charged GAGs soon after a joint injury may limit the extent of electrostatic interactions available for binding and retention of cationic solutes within the tissue. A post-injury condition was simulated using chondroitinase-ABC to remove ∼40% of explant GAG chains. Avidin uptake was not as high as in normal cartilage, but still achieved a very high value of 24 (FIG. 12A), and remained bound to intra-tissue sites even when placed in 1×PBS desorption bath. Together, these observations show that Avidin may be useful in-vivo as a model drug delivery mechanism for cartilage, and that therapeutic drug carriers with properties similar to Avidin (∼7 nm diameter and a high positive charge) might enable rapid, high uptake inside the cartilage, bind within the tissue, and thereby providing sustained local drug delivery.

Conclusion: Based on the results, a mechanism for nanoparticle based drug delivery into cartilage is proposed, involving highly positively charged drug carrying particles with diameter<10 nm, which can diffuse through the full thickness of cartilage and are capable of binding to sites within the ECM. Avidin provides an excellent example of such a nanoparticle, which may release and deliver low molecular weight functionalized drugs. A second approach may utilize slightly larger sized particles that can bind within the superficial zone of cartilage and then release functionalized drugs. The QD data of FIG. 2 exemplifies this approach. As these particles gradually degrade, they release drugs which may then diffuse and/or bind to sites within the cartilage over time. With both approaches, electrostatic interactions between positively charged nanoparticles and the negative fixed charge of cartilage ECM may by optimized to augment transport, uptake and intra-tissue binding of such drug carriers.

Example 5

Electrostatic Interactions Enable Rapid Penetration, Enhanced Uptake and Retention of Intra-Articular Injected Avidin in Rat Knee Joints Introduction:

Intra-articular drug delivery for local treatment of osteoarthritis remains inadequate due to rapid clearance of drugs from the vasculature or lymphatics with half-lives reported within a few hours. Local therapy of specific target tissues like cartilage is further complicated by its dense meshwork of collagen and negatively charged proteoglycans, which can prevent even the nano-sized solutes from entering. Previous examples showed that Avidin due to its ideal size (7 nm diameter) and a high positive charge (pI 10.5) penetrated through the full thickness of bovine cartilage and retained inside for 15 days. With the goal of using Avidin as a nano-carrier for local delivery of drugs into cartilage, its in-vivo transport properties were investigated using a rat model. Avidin penetrated through the full thickness of cartilage within 6 h with a half-life of 29 h and a dwell time of 7 days inside the joint. Highest concentration of Avidin was found in cartilage, least in patella tendon and none in the femoral bone while there was no Neutravidin (neutral counterpart of Avidin) present in cartilage at 24 h. A positive correlation between tissue sGAG content and Avidin's uptake ($R^2$=0.83) confirmed effects of electrostatic interactions. The biological toxicity test showed that Avidin doses up to at least 1 µM were safe.

Avidin is a globular 66 kDa (diameter~7 nm), highly glycosylated and positively charged protein (pI 10.5). In this example we used Avidin as a model for charge driven transport and showed that it penetrated through the full thickness of bovine cartilage within 1 day, while its neutral same-sized counterpart, Neutravidin, penetrated only half the sample thickness in 4 days. Avidin had a 400-fold higher uptake and greater than 90% of the absorbed Avidin remained bound to the negatively charged groups within cartilage explants for at least 15 days as shown herein. Avidin was found to bind with intra-tissue sites in cartilage due to reversible and weak electrostatic interactions with a dissociation constant, $K_D$, of 150 µM. The large effective binding site density ($N_T$~2920 µM) of negatively charged groups, however, facilitated retention of Avidin, making its structure suitable for particle based drug delivery into cartilage.

With the goal of using Avidin as a drug delivery carrier, fluorescently labeled Avidin was injected into the knee joints of healthy rats. The objectives of this study were: (i) to investigate Avidin's kinetics, distribution and retention throughout the joint space over 7 days by using an in vivo rat model where the convective transport and lymphatic systems are present and (ii) to study dose dependent effects of Avidin on chondrocyte viability, sGAG content, and biosynthesis levels using bovine cartilage explants to determine the safe limit of Avidin dose for drug delivery.

Materials and Methods

In-vivo Study Design

Animal studies were performed as pre-approved by the Institutional Animal Care and Use Committee at BIDMC. Intra-articular (i.a.) injections of 50 µl of 50 µM Avidin (pI 10.5, 66 kDa, diameter~7 nm) or Neutravidin (neutral at pI 7, 60 kDa, diameter~7 nm) conjugated with Texas Red (both from Invitrogen, CA) were administered in the right knee joints of healthy 18-20 weeks old Fischer-344 rats (Charles River Laboratories). Following the injection, rat knees were flexed and extended to distribute the injected solute throughout the intra-articular space. Contralateral left knees were used as controls. Avidin injected rats were sacrificed at 4 different time points (6 h, 1 d, 4 d, 7 d) and Neutravidin injected rats were sacrificed after 1 day. The following tissue types were extracted from each joint: articular cartilage removed from the patellar groove, femoral condyle and tibial plateau using a scalpel; medial and lateral menisci; i.a. ligaments (ACL & PCL); patellar and quadriceps tendons; and femoral bone. 6 rats were used per treatment condition for a total of 30 rats. Using a digital caliper (Fisher Scientific), the joint thickness was measured before and after the injection at each time point to check for joint swelling indicating an inflammatory response to the injection.

Confocal Microscopy

Tissue samples extracted from the rat joints injected with Avidin-Texas Red (Excitation at 595 nm and emission at 615 nm) and sacrificed at 6 h were imaged using a confocal microscope (OLYMPUS, FluoView FV1000) at 10× magnification by taking Z stacks. Images were taken in X-Y plane, which represents the surface through which Avidin diffused. 3D images were reconstructed using Z stacking (slice thickness~4.5 µm) and cross-sections in the X-Z plane of these 3D images were taken. Confocal images of tissue specimen from the contralateral control knees exhibited no fluorescence.

Quantitative Analysis of Avidin/Neutravidin Uptake into Tissue Samples

Tissue samples from all treatment conditions were then desorbed in 10×PBS for 48 h in 37° C. incubator to disrupt electrostatic interactions and release Avidin/Neutravidin into the desorption bath. Desorption for longer than 48 h did not increase the fluorescence signal in the bath. At the end of the experiment, tissue samples were removed from the bath, lyophilized and the dry weight was measured. Fluorescence signal from desorption bath was quantified using a plate reader (Synergy HT, BioTek). In establishing standard curves, the fluorescence intensities and solute concentrations for both Avidin-Red and Neutravidin-Red were found to be linear with bath concentration. The solute uptake was calculated as the concentration of labeled solute in the tissue samples normalized by tissue dry weight.

sGAG Measurement and Histological Analysis

To understand the effects of the negatively charged glycosaminoglycan (GAG) chains on Avidin uptake and binding within different tissue types, the sulfated GAG (sGAG) concentration was measured in each tissue by using the dimethyl-methylene blue (DMMB) dye binding assay (Farndale et al., *Biochim. Biophys. Act,* 1986). Naïve rat joints or dissected joint tissues were simultaneously fixed and decalcified in Formical-4 (Decal Chemical Corporation) for 24-72 h, depending on the bone content of the tissue specimen. Following decalcification, specimens were dehydrated and embedded in paraffin, and either sagittal or coronal sections (5 µm) were made at 300 µm intervals throughout the specimen. Sections were stained with Toluidine Blue to image the amount and distribution of sGAG, staining all sections simultaneously to minimize variation in staining among specimens.

Dose Dependent Avidin's Biological Response Using Bovine Cartilage (in-vitro study)

Dose dependent biological response to Avidin was tested using bovine cartilage explants. Bovine cartilage disks were harvested from the femoropatellar grooves of 1-2 week old bovine calf knee joints (obtained from Research 87, Hopkinton, Mass.). Briefly, cylindrical cartilage disks (3 mm) were cored using a dermal punch and then sliced to obtain the top 1 mm of cartilage with intact superficial zone. Cartilage disks for all treatment groups were matched for depth and location along the joint surface. They were equilibrated in serum free medium (low glucose Dulbecco's Modified Eagle's Medium [DMEM; 1 g/L]) supplemented with 10 mM HEPES buffer, 0.1 mM nonessential amino acids, 0.4 mM proline, 20 g/ml ascorbic acis, 100 units/ml penicillin G, 100 g/ml streptomycin and 0.25 g/ml amphotericin B (all from Sigma Aldrich, MO) for 48 h in a 5% $CO_2$ incubator at 37° C. prior to any treatment. The disks were then cultured with the following one time dose of Avidin: 0, 100 nM, 1 μM and 100 μM for 48 h. The medium was changed every 2 days without replenishing Avidin. This simulated the in-vivo condition of one time Avidin injection. The experiment was conducted for three time periods: 2, 4 and 10 days.

Chondrocyte Viability

Upon termination of culture at these time points, 100-200 μm thick slices were cut from the center of disks from each treatment condition. The slices were immediately stained for 2-3 minutes in the dark with fluorescein diacetate (FDA; 4 mg/ml in PBS) and propidium iodide (PI; 40 mg/ml in PBS) (both from Sigma Aldrich, MO). FDA was used to stain the viable cells green, while PI stained the non-viable cells red. The slices were washed with PBS and then imaged using Nikon fluorescence microscope with a 4× objective.

Measurement of sGAG Loss to Media, Chondrocyte Protein and sGAG Biosynthesis

Two days before the termination of culture of day 4 and day 10 experiments, the medium was supplemented with 5 μCi/mL [$^{35}$S]-sulfate and 10 μCi/mL [$^{3}$H]-proline (both from PerkinElmer, Norwalk, Conn.). After 48 h radiolabeling, disks were washed 4 times over 80 minutes with cold PBS to completely remove the free label. The wet weight was measured for each disk and then digested with proteinase K (Roche, Indianapolis, Minn.) overnight. The cumulative sGAG content in the medium and digested explants was measured using the DMMB assay. The amount of radiolabel in each digested sample and medium standards ($^{35}$S and $^{3}$H) were measured using a liquid scintillation counter. Radiolabeled concentration was calculated from the standards and then normalized to the wet weight.

Statistical Analysis

Figure 17:
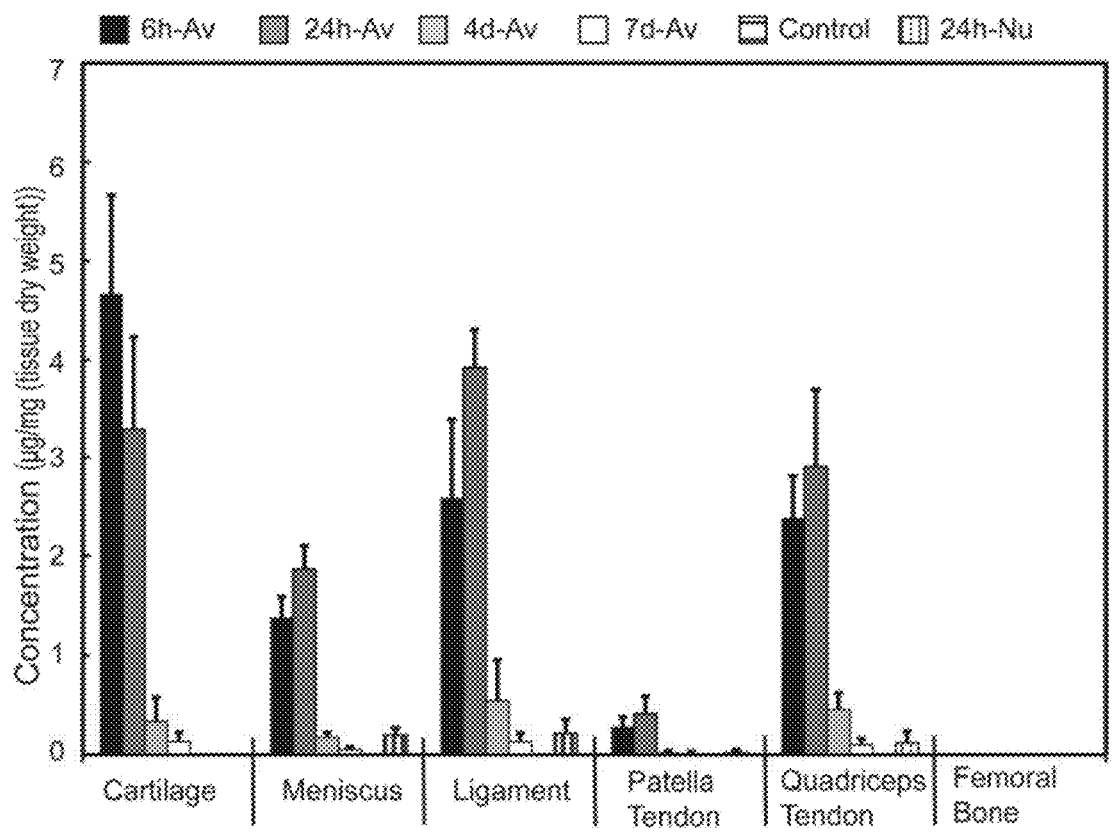
FIG. 17 depicts Avidin (Av) and Neutravidin (Nu) uptake and retention in different tissue types from rat knee joints at 6 h, 24 h, 4 days and 7 days for Av and 24 h for Nu. Each treatment condition represents tissue specimens from the right knee joints of six rats. Tissue specimens from the contralateral (left) knee joints were used as controls for each treatment condition and showed zero fluorescence. Data is presented at Mean+/−SD.
Figure 18A:
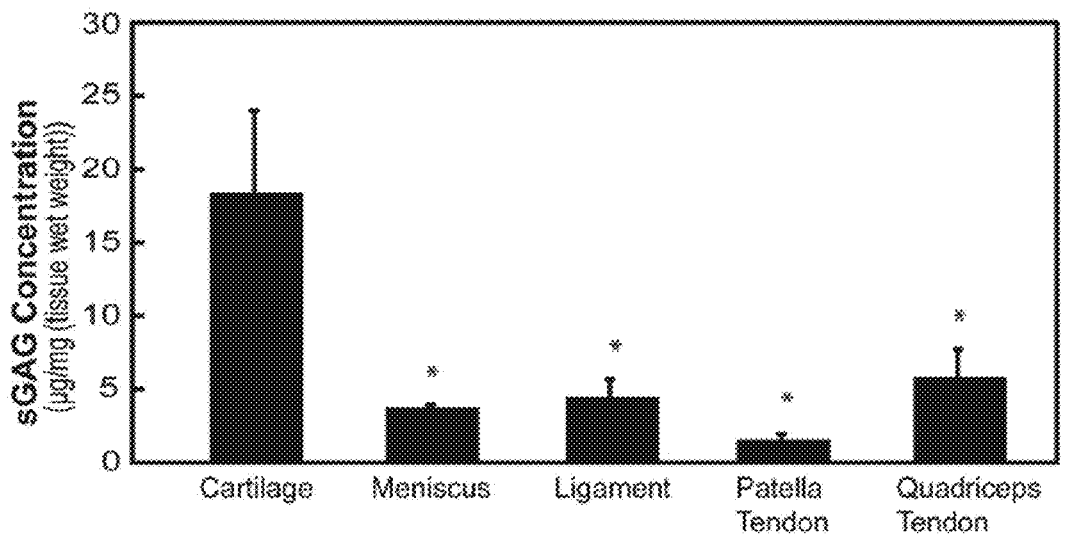
FIGS. 18A-18B depict a series of graphs describing sGAG concentration measurements.
Figure 18B:
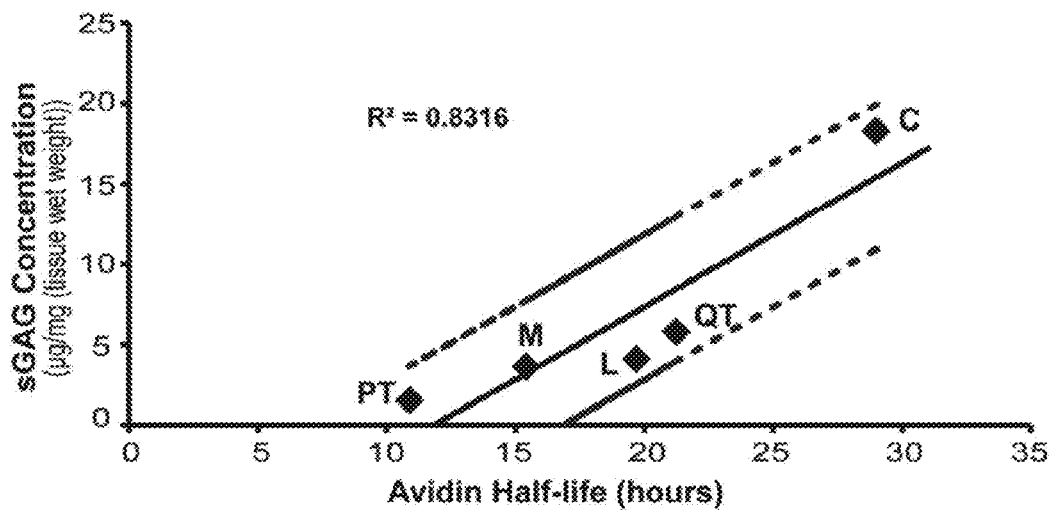

Data in FIG. 17 and FIG. 18A are presented as Mean±SD and were derived from 6 and 7 animals, respectively, for each treatment condition. The general linear mixed effects model was used with animal as a random variable for analysis followed with the Tukey's test for comparisons between multiple treatment conditions. There was no effect of animal found. FIG. 20 data is derived from 2 different animals and a total of 6 explants per animal in each treatment condition were used; data is expressed as Mean±SEM of 12 samples per treatment condition (there was no effect of animal). $p<0.05$ was used for statistical significance. In FIG. 18B, diamonds represent experimental data (mean value), solid line is the linear least square fit and the dotted lines are the 95% confidence intervals.

Results

Intra-articular (i.a.) Injection of Avidin in Rat Joints:

Following i.a. injection of Avidin, rat knee joints were check for inflammation after different time points (6 h, 1 d, 4 d and 7 d). The knee joints did not present any signs of swelling or joint stiffness. After the rats were sacrificed, the articular cartilage, menisci, i.a. ligaments, and patellar and quadriceps tendons were harvested to investigate the depth of penetration and retention of Avidin. The purple staining of Avidin-Texas Red in the rat knee joint (Texas red powder is dark purple to the naked eye) and ex tracted tissues was visible at the 6 h and 24 h time points. Confocal images showed that Avidin diffused through the full thickness of these tissues within 6 h after the i.a. injection (data not shown). Contralateral control knees did not show any fluorescence.

The mean concentration of Avidin was reported as 4.7 μg/mg tissue dry weight in articular cartilage at 6 h, which was reduced to 3.3 μg/mg by 24 h (FIG. 17). Avidin concentration further decreased to 10.3% of 24 h value (0.34 μg/mg) at 4 days and 4.1% of 24 h value at 7 days (0.13 μg/mg). Similar rates of reduction in Avidin concentration were observed in other tissue types over 7 days. The half-life of Avidin was calculated by fitting an exponential curve to the experimental data:

$$C(t)=C_0 e^{-\lambda t}$$

Where, $C_0$ is the initial and $C(t)$ is the final Avidin concentration in tissue after time t and $\lambda$ is the decay constant. Table 4 shows the mean lifetime, $\tau$ ($\tau=1/\lambda$) and half-lives calculated for each tissue type. Avidin's neutral counterpart, Neutravidin, was used, and its transport rate and binding in rat knee tissues was compared with that of Avidin at the 24 h time point. There was no Neutravidin present in rat cartilage and patellar tendon at 24 h, while small but very insignificant amounts were present in meniscus, ligaments and quadriceps tendon as compared to Avidin (FIG. 17). Neither Avidin nor Neutravidin was detected in the femoral bone at any time point.

Correlation of Avidin Uptake with sGAG Content:

sGAG concentration was measured using DMMB assay (FIG. 18A) for rat cartilage (mean concentration 18.3 μg/mg tissue wet weight), quadriceps tendon (5.8 μg/mg), ligaments (4.1 μg/mg), menisci (3.6 μg/mg) and patella tendon (1.5 μg/mg); consistent with the data reported by others in the literature (Kamisan., BMC Vet. Res., 2013; Malda et al., PloS One, 2013; Moyer et al., Acta Biomater, 2013; Amiel et al., J. Orthop. Res. Off. Publ. Orthop., 984; Rumian et al., J. Orthop. Res. Off. Publ. Orthop. Res. Soc., 2007). The high sGAG concentration in the quadriceps tendon may be due to the presence of sesamoid fibrocartilage, called the suprapatella, embedded in the deep surface of rat's quadriceps tendon immediately above the patella. It was shown previously that the rat suprapatella comprised of aggrecan along with its link protein and glycosaminoglycans. Suprapatella is present in many mammals, including mouse, rats, rabbits, and dogs, but is absent in humans (Tischer et al., J. Histochem. Cytochem. Off. J. Histochem. Soc., 2002; Ralphs et al., Anat. Rec., 1991). The half-life of Avidin retention in different tissue types (Table 4) directly correlated with the respective sGAG concentration ($R^2=0.83$), confirming the effects of strong electrostatic interactions (FIG. 18B). 95% confidence interval lines had positive slope indicating that trends were significant. Toluidine Blue staining of the knee tissues (FIG. 19) revealed the relative concentration and spatial distribution of sGAG within the different joint compartments. The metachromatic shift in shades of gray specified sGAG within the articular cartilage of the femoral condyle (FIG. 19A-B), tibial plateau (FIG. 19C-D), and femoral trochlea (FIG. 19 E-F). The suprapatella could be distinguished from the adjacent quadriceps tendon by increased sGAG staining and decreased presence of parallel collagen fibers (FIG. 19G-H). Less intense staining was also observed in the patella tendon (FIG. 19E-F) and also within the mid-length of the i.a. ligaments (FIG. 19I-J). These observations were all consistent with DMMB assay results (FIG. 18A).

Effect of Avidin Dose on Chondrocyte Viability:

To estimate the safe limit of Avidin dose, cell viability was assessed via live-dead fluorescence in bovine explants after 2, 4, and 10 days treatments for a one time dose of 0-100 µM Avidin. There was minimal cell death in the control over 10 days and no significant difference in cell viability was observed among the different treatment groups during this time period (data not shown). Note that variable cell death in the soft superficial zone is typically observed even in untreated explants (due to its vulnerability to compressive injury), depending on which location along the joint surface they were harvested from.

Figure 20A:
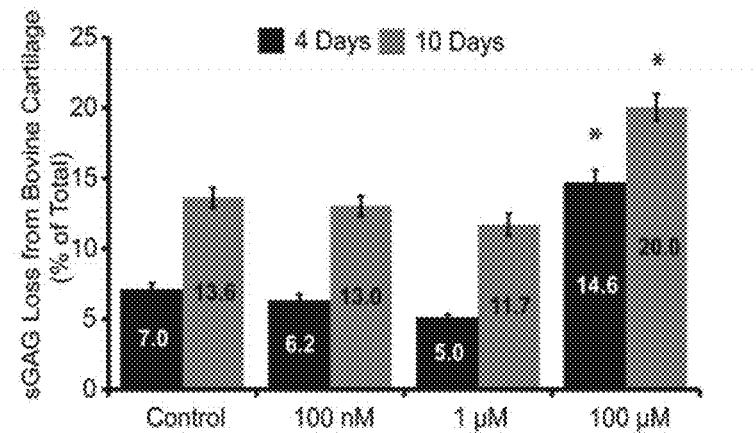
FIGS. 20A-20C depict a series of graphs.
Figure 20B:
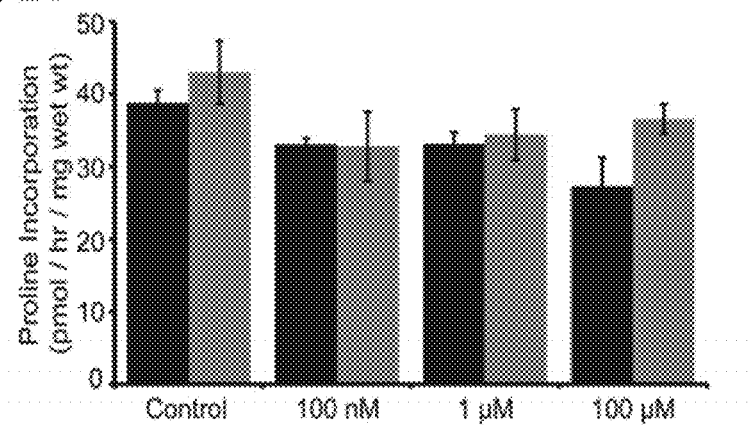
Figure 20C:
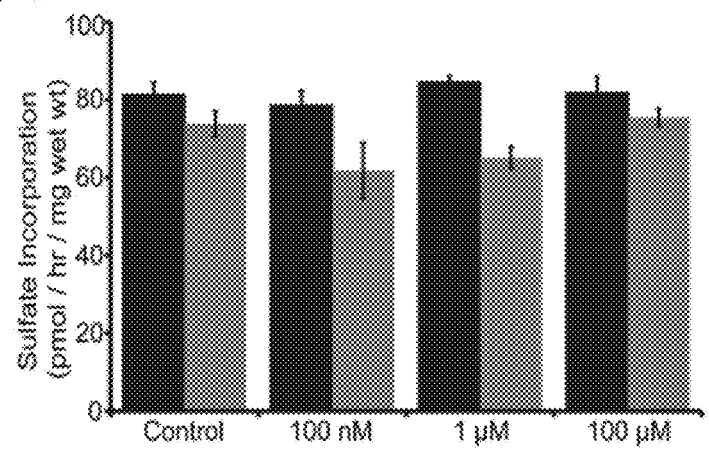

Cumulative sGAG Loss and Biosynthesis:

There was no significant difference in the cumulative sGAG loss to medium between the untreated control, 100 nM and 1 µM Avidin treated conditions when measured at 4 and 10 days (FIG. 20A). The 100 µM condition resulted in higher sGAG loss compared to the control during 4 days (7% for control vs. 14.6% for 100 µM) and 10 days (13.6% vs. 20%). There were no significant changes in the rate of protein and sGAG synthesis with increasing Avidin dose (FIGS. 20B and 20C).

Discussion

The complex architecture of cartilage can prevent even nano-sized solutes from entering into its deeper zones, making local delivery of drugs into specific target tissues a challenge (Larsen, J. Pharm. Sci., 2008). Avidin, due to its ideal size and high positive charge (+6 to +14) exhibited a fast rate of transport, 400× higher uptake than its neutral counterpart and >90% retention for over 10 days in bovine cartilage[8]. This shows that Avidin may offer an ideal structure as a carrier for local drug delivery into cartilage.

The in vivo rat studies presented here account for the presence of lymphatics and convective flow and revealed similar transport properties for Avidin as in the in vitro bovine experiments. The data showed that Avidin penetrated throughout the full thickness of different tissue types within 6 h, resulting in highest uptake within cartilage, least within the patella tendon and none within the femoral bone (FIG. 17). A positive correlation ($R^2=0.83$) between the sGAG concentration in different tissues (FIG. 18A) and their respective Avidin half-lives (Table 4) confirmed the effects of strong electrostatic interactions between positively charged Avidin and the negatively charged groups in these tissues. The electrostatic interactions augmented Avidin's transport rate due to Donnan partitioning, enabling distribution throughout the joint and penetration deep into the tissues before being cleared by the lymphatic system. Avidin was retained inside the rat joint for 7 days with a half-life of 29 h in cartilage, whereas its neutral counterpart, Neutravidin, exhibited almost complete clearance within 24 h of i.a. injection. Half-lives of similar sized solutes like albumin have been reported to range between 1.23-3.9 h in the rabbit knee (Larsen, J. Pharm. Sci., 2008).

Intra-articular injections of corticosteroid and hyaluronate preparations are prescribed for management of osteoarthritis related pain and inflammation when NSAIDs are not effective. However, short half-lives for corticosteroids have been reported as 1-4 h due to their low molecular weight (<700 Da)[3] and for hyaluronate preparations as 12-24 h (MW~300 kDa) in human joint space[17], hence requiring the need for multiple injections. Several drugs have been identified as potentially useful to reverse or prevent post-traumatic osteoarthritis (PTOA) with the associated breakdown of cartilage, including anti-catabolic glucocorticoids (e.g., dexamethasone) and pro-anabolic growth factors (e.g., IGF-1, FGF-18, and BMP-7) (Hunter et al., Nat. Rev. Rheumatol., 2011; However, no drug has yet passed important safety and efficacy requirements of preventing its rapid clearance into systemic circulation and reducing the systemic drug side-effects. As shown in the instant invention a vehicle like Avidin, however, can transport such drugs into cartilage at a fast rate, reversibly binding within the tissue and creating a drug depot inside cartilage. Furthermore, Avidin's high uptake in ligaments can be utilized for delivering pro-anabolic growth factors following ligament injury.

The concentration of Avidin in rat cartilage was 3 times lower than reported for bovine cartilage in vitro. This may be due to the 2.5-3× lower sGAG concentration of cartilage in the rat than in the young bovine. >90% retention of Avidin was reported in bovine cartilage (in vitro) for at least 15 days. A drop in retention is expected because of the absence of convective transport within the in vitro system. However, the 4.1% retention at 7 day in the rat study is likely due to the 10× lower thickness of rat cartilage as compared to bovine. Since the diffusion-binding time constant scales as square of thickness, the transport rate through rat cartilage is expected to be 100 times faster, explaining the shorter retention duration. An animal model having a thicker cartilage like rabbit or goat (Kamisan., BMC Vet. Res., 2013) may be a closer representation of human physiology. Moreover, the sGAG concentration gradient is larger between cartilage and other i.a. tissues, such as the ligaments, within human compared to rat joints, so that Avidin transport in the former should more heavily favor cartilage. This may have implications for specificity of action following Avidin-mediated drug delivery within the joint.

The dose dependent biological effects of Avidin was also examined to estimate its safe dose. A one-time dose of 0-100 µM Avidin did not cause any change in chondrocyte viability in bovine cartilage explants during 10 days. While the sGAG loss to medium did not change for a 0-1 µM dose range over 10 days, about 2 folds increase in sGAG loss for 100 µM dose at both 4 and 10 days was observed as compared to the untreated control condition. 100 µM concentration of Avidin, which is highly positively charged, may shield the electrostatic interactions between the negatively charged groups in cartilage thereby reducing the osmotic pressure. This may force out both water molecules and proteoglycans. The cell biosynthesis rates (both sGAG and protein), however, were not affected for this dose range, suggesting that Avidin did not cause chondrotoxicity. This shows that Avidin doses up to at least 1 µM are safe. Recently, it was shown that a continuous dose of 100 nM dexamethasone was able to significantly reduce the catabolic effects of mechanical injury and increased levels of inflammatory cytokines in an in-vitro human cartilage explant study (Lu et al., Arthritis Res. Ther., 2011) Biotinylated dexamethasone can be conjugated to the 4 biotin binding sites of Avidin (Ellison et al., Protein Sci. Publ. Protein Soc., 1995) providing at least a 4:1 molar ratio of dexamethasone to Avidin. Thus <1 µM doses of Avidin are estimated to be able to provide a sustained release of 100 nM dexamethasone.

In summary, in vivo rat data showed that electrostatic interactions can be utilized for augmenting transport and increasing retention of small MW drugs, such as dexamethasone, inside cartilage. Avidin exhibits an ideal structure (due to its size and a high positive charge) that can be conjugated with small MW therapeutics to enable their safe and effective intra-articular delivery.

TABLE 4

The half-life of Avidin retention in different tissue types

| Tissue type | τ(mean lifetime) = 1/λ (hours) | Half-life (hours) |
|---|---|---|
| Cartilage | 41.8 | 29.0 |
| Meniscus | 30.9 | 21.4 |
| Ligament | 37.0 | 25.7 |
| Patella Tendon | 24.4 | 16.9 |
| Quadriceps Tendon | 39.3 | 27.2 |

Example 6

Design and Development of Avidin Conjugated Dexamethasone Structures

Methods
Synthesis of Dexamethasone Conjugated to Avidin Through Ester Linkage:

Synthesis of Dexamethasone Hemisuccinate (2): An amount equivalent to 0.030 g of dexamethasone (1, 0.076 mmol, 1.0 equiv.) was completely dissolved in 1 mL of pyridine (non-anhydrous) and 0.038 g of succinic anhydride (0.382 mmol, 5.0 equiv.) was added to the clear solution. Then 1-2 mg of DMAP (7.6 mol, 0.1 equiv.) was added to the solution and reaction was allowed to run for 48 h at r.t. under $N_2$-flow. After 48 h, pyridine was evaporated under reduced pressure (in a rotary evaporator). A volume equivalent to 10 mL of $H_2O$ was added to the evaporated residue. A white precipitate was observed which was stirred for 10 minutes and then centrifuged. The resulting precipitate was washed again with 10 mL of $H_2O$ and the washed residue was lyophilized to yield the target product (2).

Figure 23:
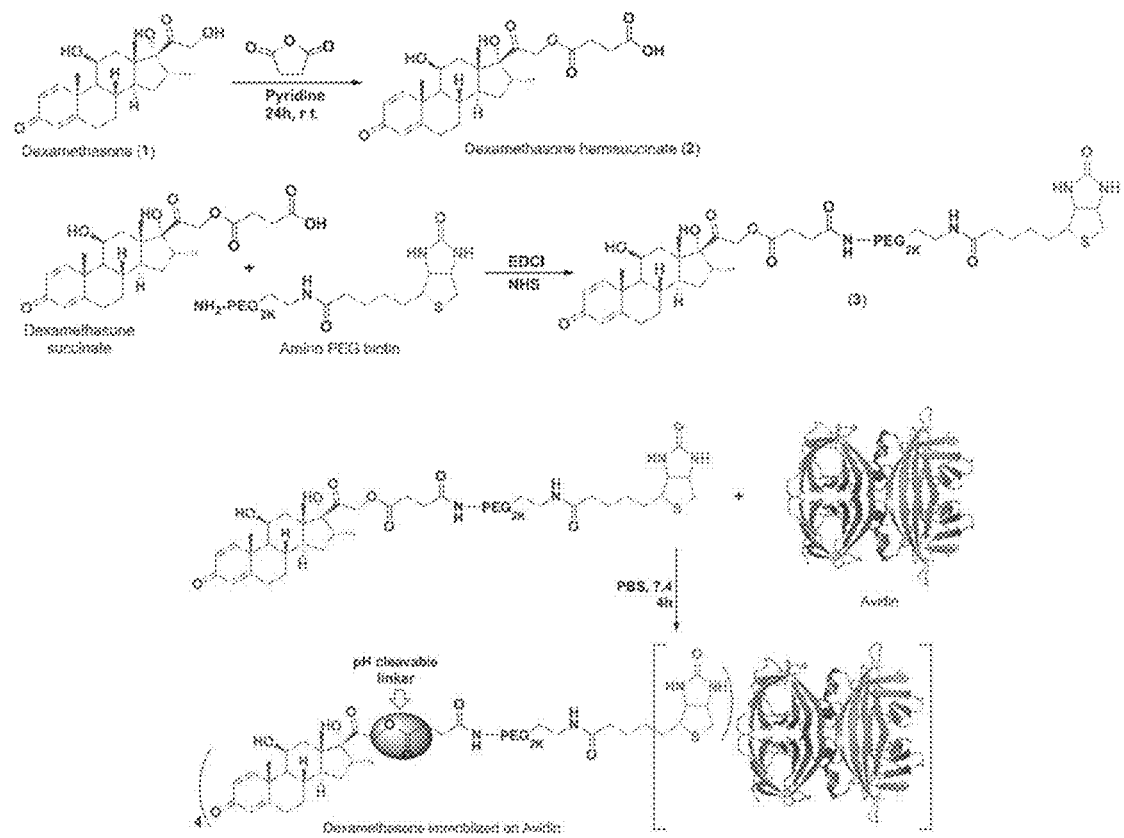
FIG. 23 depicts a scheme of a synthetic pathway towards dexamethasone immobilized Avidin (ester bond).

Conjugation of Dexamethasone Hemisuccinate with Biotinylated PEG-amine:

Dexamethasone hemisuccinate (2, 0.020 g, 0.0406 mmol, 1.0 equiv.) was completely dissolved in anhydrous DMF. An amount equivalent to 0.244 g (0.048 mmol, 1.2 equiv.) of biotinylated PEG amine was added to the DMF solution of 2. Subsequently 0.0187 g (4.0 equiv) of NHS was added to the same solution and the reaction was activated for 15 minutes, after which 0.039 g (5.0 equiv.) of EDCI was added to the solution. The reaction was allowed to run for 48 h under $N_2$-flow. After 48 h, DMF was evaporated, and the reaction mixture was redissolved in minimum volume of DMF again, which was passed through size exclusion chromatography with Sephadex LH20. Eluted fractions which are positive to amines (due to biotin secondary amines) towards Ninhydrin reagent, are collected and pooled. DMF was evaporated from the collected fractions to yield viscous yellowish product of biotinylated PEG-dexamethasone (3) FIG. 23 depicts a scheme of a synthetic pathway towards dexamethasone immobilized Avidin (ester bond)

Synthesis of Dexamethasone Conjugated to Avidin Through pH Sensitive Hydrazone Linkage:

Synthesis of (6-maleimido Proprioyl) Hydrazone of Dexamethasone (4): Dexamethasone hydrochloride (1) and N-β-maleimidopropionic acid hydrazide trifluoroacetate salt (BMPH) were dissolved in 5 mL of methanol. Trifluoroacetic acid (1.92 uL) was added and the solution was stirred at r.t. for 24 h. The methanolic solution was concentrated under reduced pressure at 31° C. to a volume of 0.96 mL. To this concentrated solution, 5 mL PBS (pH 7.4) was added and the resulting suspension was allowed to stand at 4° C. for 48 h for crystallization of the product. The solid hydrazone was isolated by centrifugation, washed with fresh PBS and lyophilized to yield (β-maleimidopropioyl) hydrazone of dexamethasone (4).

Figure 24:
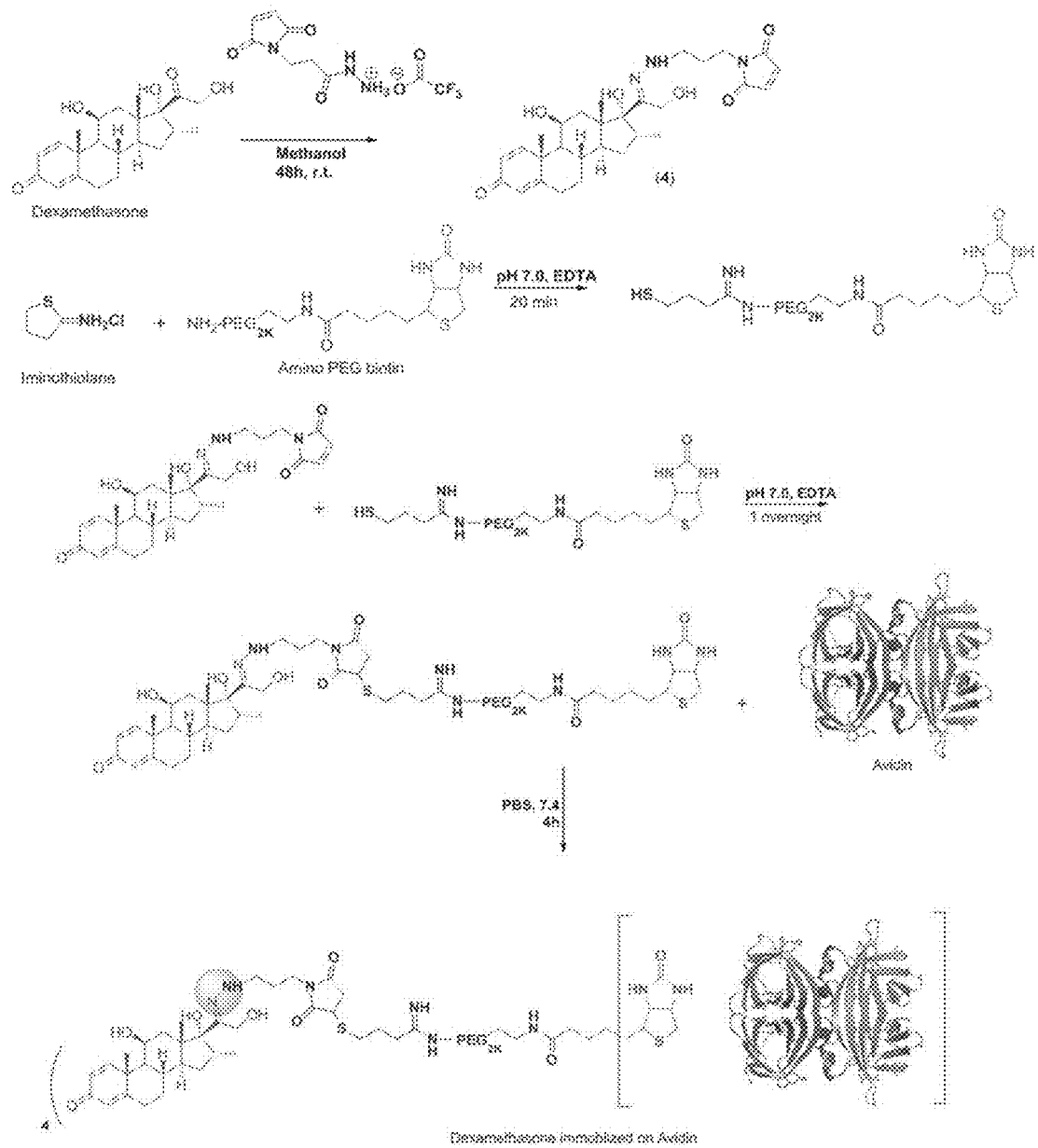
FIG. 24 depicts a scheme of a synthesis of dexamethasone immobilized avidin through formation of hydrazone bond.

Conjugation of (β-maleimidopropioyl) Hydrazone of Dexamethasone to Biotinylated-PEG Amine:

Iminothiolane hydrochloride (0.002 mg, 20 mol, 5.0 equiv.) was dissolved in 1 mL of sodium phosphate buffer with EDTA (pH 7.0). Biotinylated PEG amine (0.020 g, 4.0 mol, 1.0 equiv.) was dissolved in 0.5 mL of the same buffer. Iminothiolane hydrochloride solution prepared before is added to the PEG solution and the reaction is allowed to stir for 20 min. (β-maleimidopropioyl) hydrazone of dexamethasone was dissolved in minimum volume of DMSO and is added to the buffer solution containing iminothiolane activated biotinylated PEG amine. The reaction was allowed to run for 1 overnight. The precipitate was centrifuged out and discarded. A short dialysis of the supernatent of 4 h was carried out against PBS (pH 7.4) to remove DMSO, and the solution was lyophilized to yield the final product. FIG. 24 depicts a scheme of a synthesis of dexamethasone immobilized avidin through formation of hydrazone bond.

Results

It is important for a drug delivery system to enable a burst release of drug inside the joint to provide an instant pain and inflammation relief after a mechanical injury followed by a sustained release of small doses of drugs for several days to reduce the catabolic effects of injury and increased levels of inflammatory cytokines. Following acute joint injury, there is an immediate increase in synovial fluid levels of inflammatory cytokines (e.g., IL-1, IL-6, TNFα), which can diffuse into cartilage and rapidly initiate proteolysis and loss of cartilage matrix. Herein presented are a variety of structures that have been designed using Avidin as the drug carrier and dexamethasone as an example drug.

Broadly, non-covalent conjugation between Avidin and dexamethasone was used to enable burst release of drug (to provide immediate effect) and a direct covalent conjugation was used to enable drug release over a period of time, thereby providing a sustained long term effect to elicit a biological response. For the non-covalent conjugation, drug was entrapped inside Avidin structure supra-molecularly, while an ester linker and/or pH sensitive hydrazone linker was utilized for the covalent conjugation. Additionally, in one construct, a pegylated Avidin was used as a drug carrier.

Supra-molecular Entrapment using non-covalent bonds was achieved using Avidin+Dexamethasone and Avidin-$PEG_{2K}$+Dexamethasone. Covalent conjugation was achieved for Avidin–Dexamethasone and Avidin-$PEG_{2K}$–Dexamethasone. Numerous other combinations are within the skill of the ordinary artisan and can be achieved using the invention described herein.

Figure 21A:
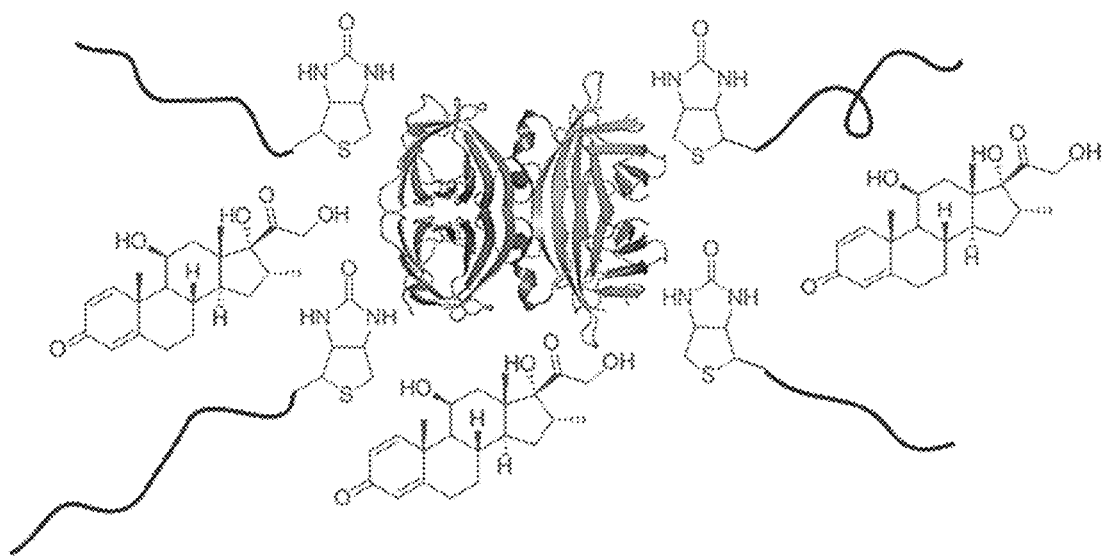
FIG. 21A depicts the supra-molecular entrapment of dexamethasone within PEG Avidin.
Figure 22A:
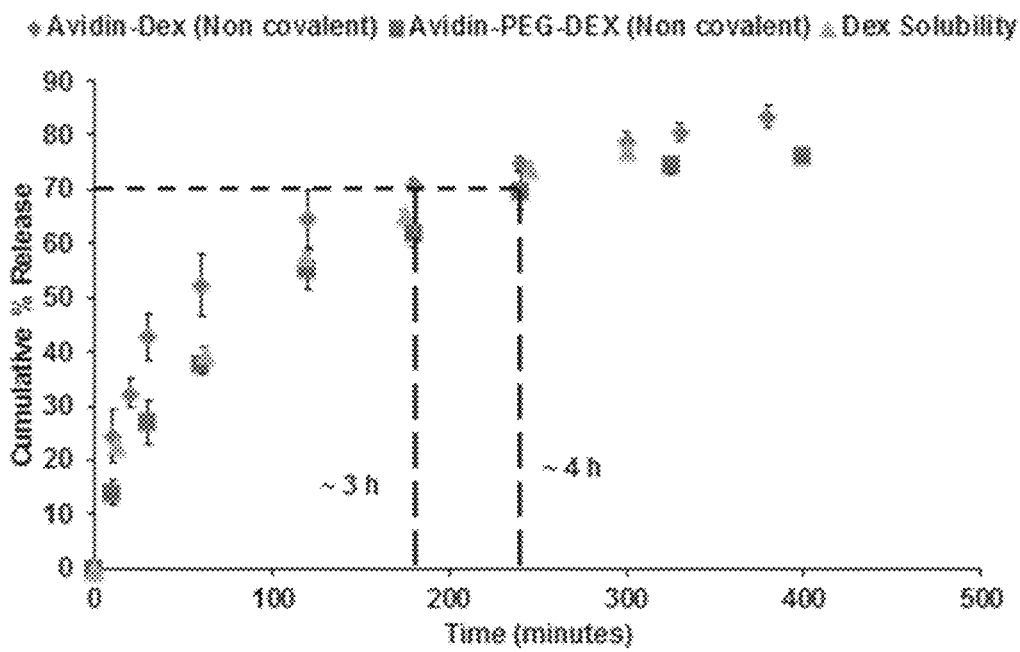
FIGS. 22A-22C.

Supra-molecular entrapment (non-covalent encapsulation) is shown for instance, in FIG. 21A. FIG. 21A shows supra-molecular entrapment of dexamethasone within pegylated Avidin. A ~33% drug loading content was achieved with both configurations (pegylated and non-pegylated versions). Both structures resulted in a burst release of dexamethasone; 70% of the drug was released within 3-4 h at pH7, 37 C (FIG. 22A).

Figure 21B:
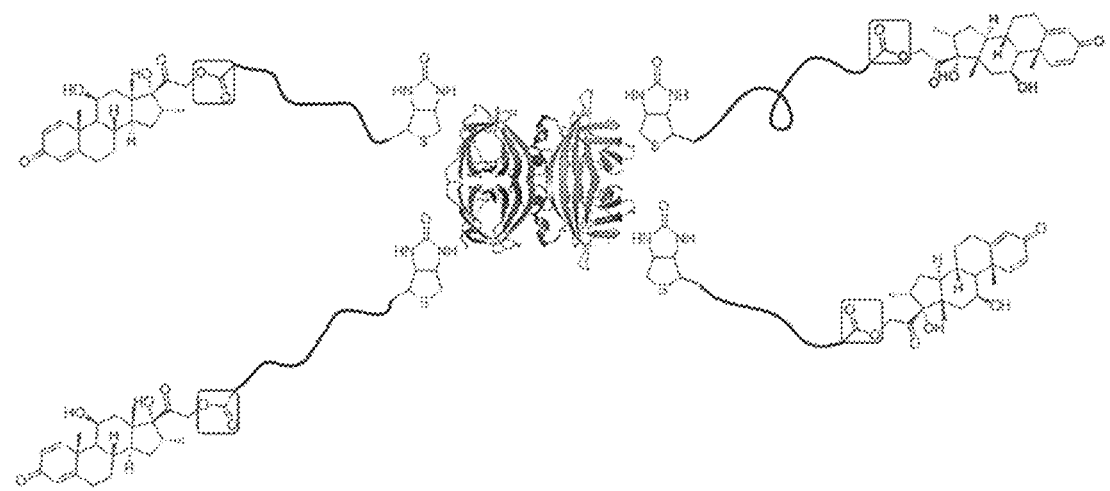
FIG. 21B depicts the ester-linked dexamethasone within the PEG Avidin.
Figure 21C:
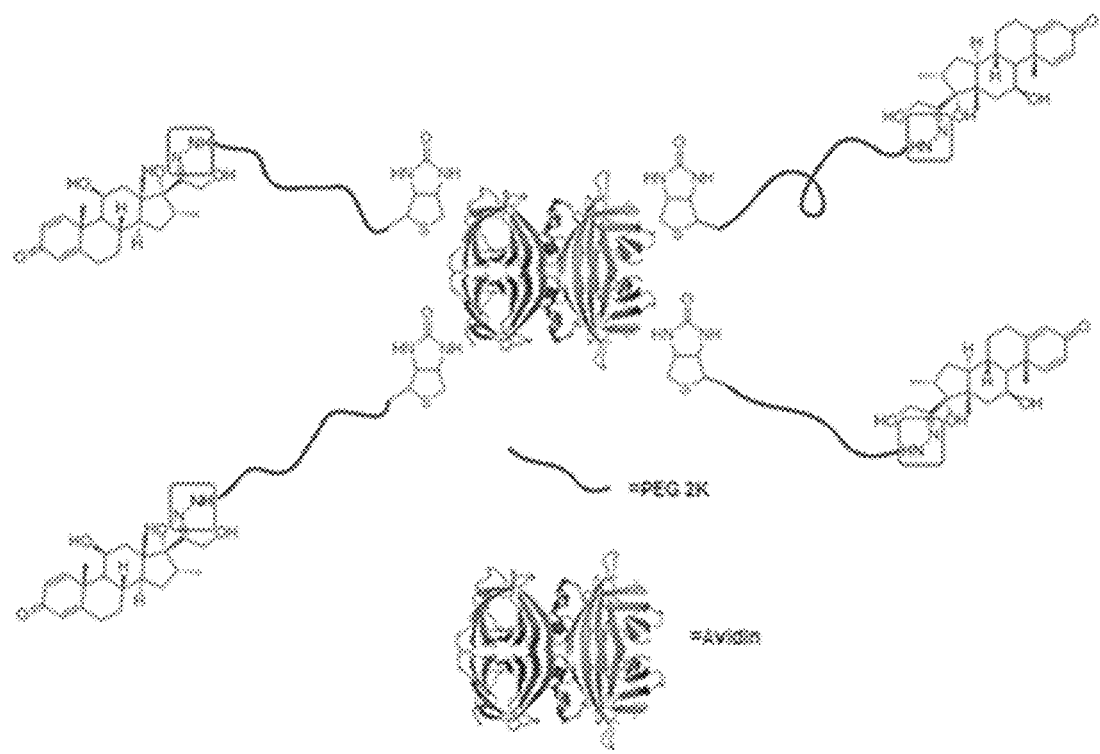
FIG. 21C depicts Hydrazone linked dexamethasone within PEG Avidin.
Figure 22B:
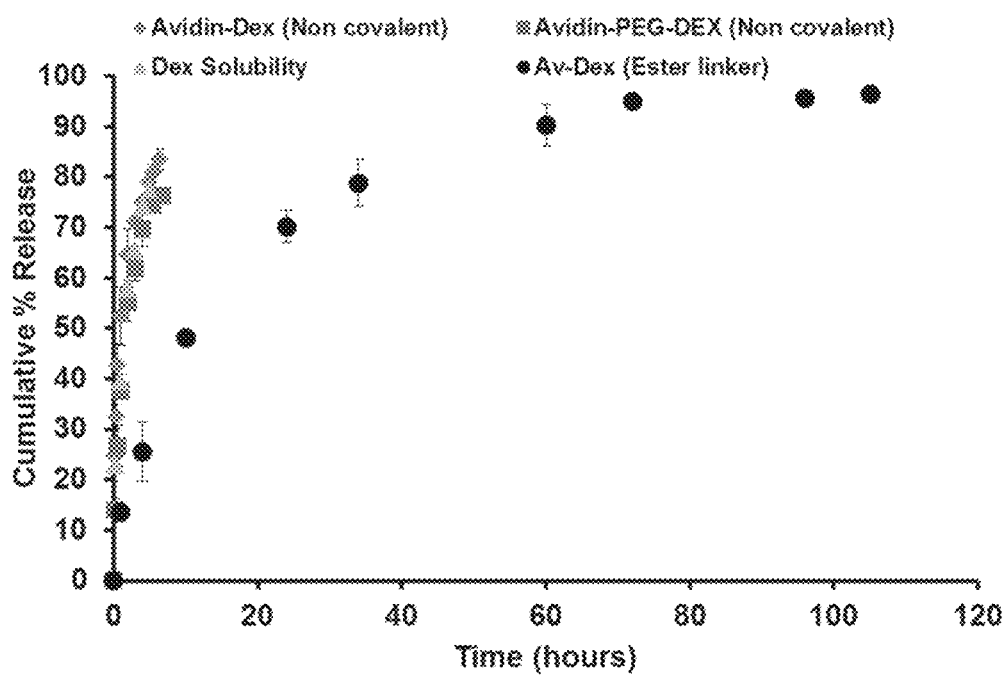
Figure 22C:
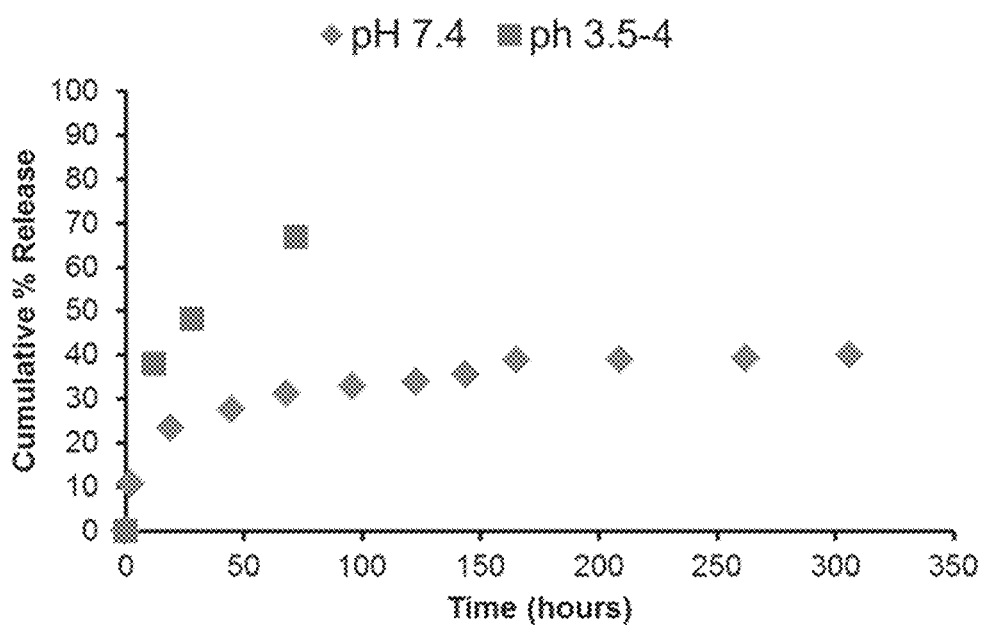

FIG. 21B-C show Avidin conjugated with dexamethasone with an ester and hydrazone linker respectively. The ester linker resulted in mean lifetime of 20.8 h (half-life~14.4 h) while the hydrazone linker was extremely stable at pH 7. FIG. 22B compares drug release profiles for non-covalent conjugation chemistry and ester linker. FIG. 22C compares the release profiles of hydrazone linker at pH 7 and pH4. The end product is Avidin (pegylated or non-pegylated) which is non-covalently loaded with dexamethasone as well as covalently conjugated via ester and/or hydrazone linker.

PLGA/polymeric particles greater than 40 nm in diameter that either have Avidin-Dex covalent structures tethered on their surface or encapsulated within were produced. Such structures will act as drug depot inside the joint thereby increasing the mean half-life. As Avidin-Dex structures are released from the polymeric particles, due to electrostatic interactions, they will penetrate into cartilage.

Example 7

Biological Responses of Avidin Conjugated Dexamethasone Through an Ester Linkage The avidin-dexamethasone structure created using ester linkages as shown in Example 6 was tested for biological activity in an in vitro cartilage tissue system.

Figure 25A:
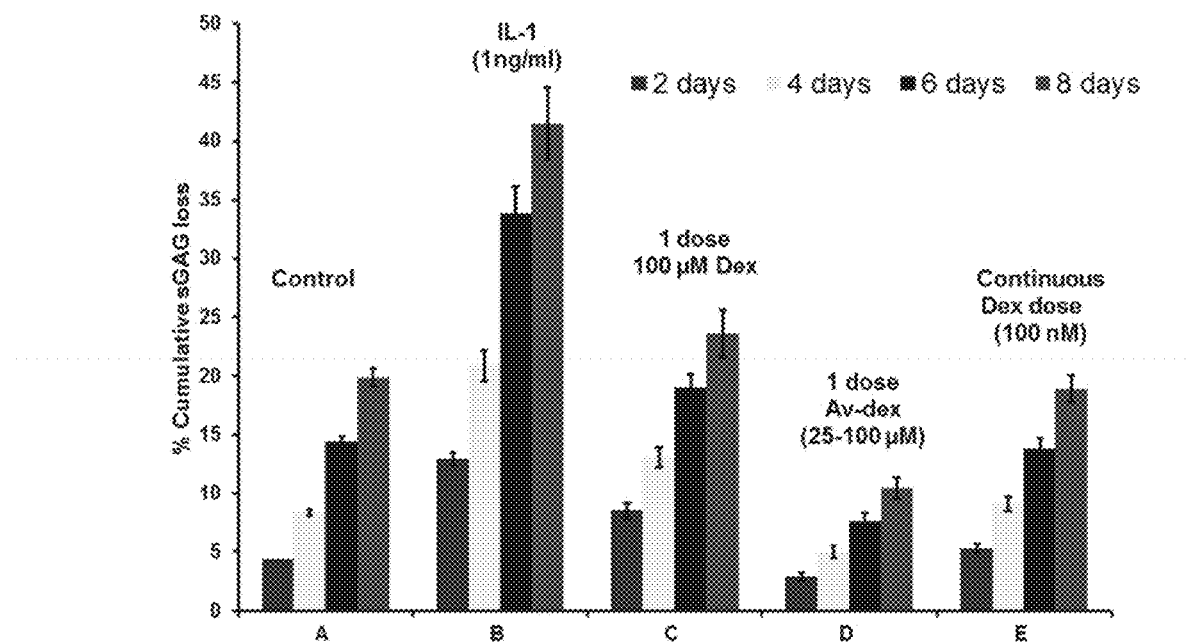
FIGS. 25A and 25B depict the avidin-dexamethasone structure created using ester linkages as shown in FIG. 23.
Figure 25B:
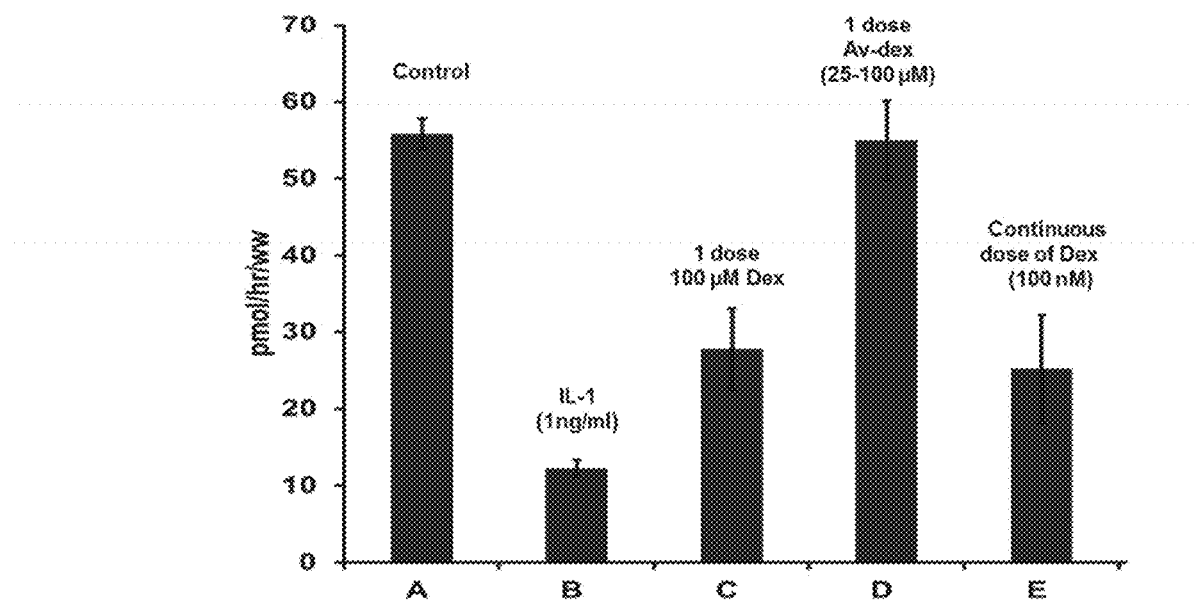

In an in vitro system, cartilage tissue was exposed to either control, IL-1 (1 ng/ml), a single dose of dexamethasone (100 μm), a single dose of avidin-dexamethasone particles (25-100 μm), or a continuous dose of Dexamethasone (100 nM) over the course of 8 days. The percent cumulative sGAG loss (FIG. 25A) was measured after 2 days, 4 days, 6 days and 8 days. The rate of sGAG synthesis was also measure for each (FIG. 25B) The single dose of avidin-dexamethasone particles significantly reduced cumulative GAG loss even compared to the continuous dose of Dexamethasone.

REFERENCES

N. Gerwin, C. Hops, A, Lucke, Intraarticular drug delivery in osteoarthritis, Advanced Drug Delivery Reviews, 2006 May 20; 58(2):226-42

S B. Abramson, Y. Yazici, Biologics in development for rheumatoid arthritis: relevance to osteoarthrits, Advanced Drug Delivery Reviews, 2006 May 20; 58(2):212-25

P. Patwari, M N. Cook, M A. DiMicco, S M. Blake, I E. James, S. Kumar, A A. Cole, M W. Lark, A J. Grodzinsky, Proteoglycan degradation after injurious compression of bovine and human articular cartilage in vitro: interaction with exogenous cytokines, Arthritis and rheumatism, 2003 May; 48(5):1292-301

H. Roos, T. Adalberth, L. Dahlberg, Osteoarthritis of the knee after injury to the anterior cruciate ligament or meniscus: the influence of time and age, Osteoarthritis Cartilage, 1995; 3: 261-267

D. D. Anderson, S. Chubinskaya, F. Guilak, J. A. Martin, T. R. Oegema, S. A. Olson, J. A. Buckwalter, Post traumatic osteoarthritis: Improved understanding and opportunities for early intervention, Journal of Orthopedic Research, 2011; 29: 802-809

Y. C. S. Lu, C. H. Evans, and A. J. Grodzinsky, Effects of short-term glucocorticoid treatment on changes in cartilage matrix degradation and chondrocyte gene expression induced by mechanical injury and inflammatory cytokines, Arthritis Research & Therapy, 2011; 13:1-15, R142

T. Tokunou, R. Miller, P. Patwari, M. E. Davis, V. F. M Segers, A. J. Grodzinsky, R. T. Lee, Engineering Insulin like growth factor for local delivery, The FASEB Journal, 2008, 22:1886-1893

Qi et al, Emerging Applications for Quantum Dots for Drug Delivery and Therapy, Expert Opin. Drug Deliv. 2008, v. 5: 263-267

R. E. Miller, A. J. Grodzinsky, K. Cummings, A. H. K. Plaas, A. A. Cole, R. T. Lee, P. Patwari, Arthritis & Rheumatism, Intra-articular injection of HB-IGF-1 sustains delivery of IGF-1 to cartilage through binding to chondroitin sulfate, 2010, 62:3686-3694

V. B. Kraus, J. Birmingham, T. V. Stabler, S. Feng, D. C. Taylor, C. T. Moorman III, W. E. Garrett, and A. P. Toth, Effects of intra-articular IL1-Ra for acute anterior cruciate ligament knee injury: a randomized controlled pilot trial (NCT00332254), Osteoarthritis and Cartilage, 2012, 20:271-278

Y. Li, P. Kopesky, B. Schoeberl and A. J. Grodzinsky, IGF-1 reduced matrix degradation and enhanced biosynthesis in IL-1α-treated injuriously compressed cartilage, 58th Trans Orthopedic Research Society, San Francisco, Feb. 3-7, 2012

American Academy of Orthopedic Surgeons, American College of Rheumatology, Orthopedic Research Society et al., The burden of musculoskeletal diseases in the United States: Prevalence, societal and Economic Cost, 2008.

Wieland H A, Michaelis M, Kirschbaum B J, Rudolphi K A. Osteoarthritis—an untreatable disease? Nat Rev Drug Discov. 2005 April; 4(4):331-44.

Lohmander L S, Englund P M, Dahl L L, Roos E M. The long-term consequence of anterior cruciate ligament and meniscus injuries: osteoarthritis. Am J Sports Med. 2007 October; 35(10):1756-69.

Brown T D, Johnston R C, Saltzman C L, Marsh J L, Buckwalter J A. Posttraumatic Osteoarthritis: A First Estimate of Incidence, Prevalence, and Burden of Disease. Journal of Orthopaedic Trauma. 2006 November; 20(10):739-44.

Hunter D J. Pharmacologic therapy for osteoarthritis—the era of disease modification. Nat Rev Rheumatol. 2011 January; 7(1):13-22.

Lu Y C, Evans C H, Grodzinsky A J. Effects of short-term glucocorticoid treatment on changes in cartilage matrix degradation and chondrocyte gene expression induced by mechanical injury and inflammatory cytokines. Arthritis Research & Therapy. 2011 Sep. 2; 13(5):R142.

Nixon A J, Brower-Toland B D, Bent S J, Saxer R A, Wilke M J, Robbins P D, et al. Insulinlike growth factor-I gene therapy applications for cartilage repair. Clin. Orthop. Relat. Res. 2000 October; (379 Suppl):S201-213.

Gerwin N, Hops C, Lucke A. Intraarticular drug delivery in osteoarthritis. Adv. Drug Deliv. Rev. 2006 May 20; 58(2): 226-42.

Gardner C R. Potential and limitations of drug targeting: An overview. Biomaterials. 1985 May; 6(3):153-60.

Rothenfluh D A, Bermudez H, O'Neil C P, Hubbell J A. Biofunctional polymer nanoparticles for intra-articular targeting and retention in cartilage. Nat Mater. 2008 March; 7(3):248-54.

Butoescu N, Seemayer C A, Foti M, Jordan O, Doelker E. Dexamethasone-containing PLGA superparamagnetic microparticles as carriers for the local treatment of arthritis. Biomaterials. 2009 March; 30(9):1772-80.

Horisawa E, Kubota K, Tuboi I, Sato K, Yamamoto H, Takeuchi H, et al. Size-dependency of DL-lactide/glycolide copolymer particulates for intra-articular delivery system on phagocytosis in rat synovium. Pharm. Res. 2002 February; 19(2):132-9.

Tunçay M, Caliş S, Kaş H S, Ercan M T, Peksoy I, Hincal A A. In vitro and in vivo evaluation of diclofenac sodium loaded albumin microspheres. J Microencapsul. 2000 April; 17(2):145-55.

Vemula P K, Boilard E, Syed A, Campbell N R, Muluneh M, Weitz D A, et al. On-demand drug delivery from selfassembled nanofibrous gels: a new approach for treatment of proteolytic disease. J Biomed Mater Res A. 2011 May; 97(2):103-10.

Burt H M, Tsallas A, Gilchrist S, Liang L S. Intra-articular drug delivery systems: overcoming the shortcomings of joint disease therapy. Expert Opinion on Drug Delivery. 2009 January; 6(1):17-26.

Elsaid K A, Ferreira L, Truong T, Liang A, Machan J, D'Souza G G. Pharmaceutical nanocarrier association with chondrocytes and cartilage explants: influence of surface modification and extracellular matrix depletion. Osteoarthr. Cartil. 2013 February; 21(2):377-84.

Comper W D. Cartilage: Molecular Aspects. Hall B K, Newman S A, editors. Boston: CRC Press; 1991.

Ng L, Grodzinsky A J, Patwari P, Sandy J, Plaas A, Ortiz C. Individual cartilage aggrecan macromolecules and their constituent glycosaminoglycans visualized via atomic force microscopy. J. Struct. Biol. 2003 September; 143(3):242-57.

Maroudas A. Transport of solutes through cartilage: permeability to large molecules. J Anat. 1976 November; 122(Pt 2):335-47.

Snowden J M, Maroudas A. The distribution of serum albumin in human normal and degenerate articular cartilage. Biochim. Biophys. Acta. 1976 May 28; 428(3):726-40.

Byun S, Sinskey Y L, Lu Y C S, Ort T, Kavalkovich K, Sivakumar P, et al. Transport of anti-IL-6 antigen binding fragments into cartilage and the effects of injury. Arch. Biochem. Biophys. 2013 Apr. 1; 532(1):15-22.

Garcia A M, Szasz N, Trippel S B, Morales T I, Grodzinsky A J, Frank E H. Transport and binding of insulin-like growth factor I through articular cartilage. Arch. Biochem. Biophys. 2003 Jul. 1; 415(1):69-79.

Yao Z, Zhang M, Sakahara H, Saga T, Arano Y, Konishi J. Avidin targeting of intraperitoneal tumor xenografts. J. Natl. Cancer Inst. 1998 Jan. 7; 90(1):25-9.

Patwari P, Cook M N, DiMicco M A, Blake S M, James I E, Kumar S, et al. Proteoglycan degradation after injurious compression of bovine and human articular cartilage in vitro: interaction with exogenous cytokines. Arthritis Rheum. 2003 May; 48(5):1292-301.

Liu W, Greytak A B, Lee J, Wong C R, Park J, Marshall L F, et al. Compact biocompatible quantum dots via RAFT-mediated synthesis of imidazole-based random copolymer ligand. J. Am. Chem. Soc. 2010 Jan. 20; 132(2):472-83.

Wong C, Stylianopoulos T, Cui J, Martin J, Chauhan VP, Jiang W, et al. Multistage nanoparticle delivery system for deep penetration into tumor tissue. PNAS [Internet]. 2011 Jan. 18 [cited 2013 Jul. 8]; Available from: pnas.org/content/early/2011/01/13/1018382108

Liotta L A, Abe S, Robey P G, Martin G R. Preferential digestion of basement membrane collagen by an enzyme derived from a metastatic murine tumor. Proc Natl Acad Sci USA. 1979 May; 76(5):2268-72.

Farndale R W, Buttle D J, Barrett A J. Improved quantitation and discrimination of sulphated glycosaminoglycans by use of dimethylmethylene blue. Biochim. Biophys. Acta. 1986 Sep. 4; 883(2):173-7.

Lotz M K. New developments in osteoarthritis. Posttraumatic osteoarthritis: pathogenesis and pharmacological treatment options. Arthritis Research & Therapy. 2010 Jun. 28; 12(3):211.

Bendele A M. Animal models of osteoarthritis. J Musculoskelet Neuronal Interact. 2001 June; 1(4):363-76.

Bonassar L J, Frank E H, Murray J C, Paguio C G, Moore V L, Lark M W, et al. Changes in cartilage composition and physical properties due to stromelysin degradation. Arthritis Rheum. 1995 February; 38(2):173-83.

Adam C, Eckstein F, Milz S, Putz R. The distribution of cartilage thickness within the joints of the lower limb of elderly individuals. J Anat. 1998 August; 193(Pt 2):203-14.

Huffman K M, Bowers J R, Dailiana Z, Huebner J L, Urbaniak J R, Kraus V B. Synovial fluid metabolites in osteonecrosis. Rheumatology (Oxford). 2007 March; 46(3):523-8.

Crank J. The mathematics of diffusion. Oxford, [Eng]: Clarendon Press; 1975.

Johnson D L, Urban W P Jr, Caborn D N, Vanarthos W J, Carlson C S. Articular cartilage changes seen with magnetic resonance imaging-detected bone bruises associated with acute anterior cruciate ligament rupture. Am J Sports Med. 1998 June; 26(3):409-14.

Sui Y, Lee J H, DiMicco M A, Vanderploeg E J, Blake S M, Hung H-H, et al. Mechanical injury potentiates proteoglycan catabolism induced by interleukin-6 with soluble interleukin-6 receptor and tumor necrosis factor $\alpha$ in immature bovine and adult human articular cartilage. Arthritis & Rheumatism. 2009; 60(10):2985-96.

Goldberg M, Langer R, Jia X. Nanostructured materials for applications in drug delivery and tissue engineering. Journal of Biomaterials Science, Polymer Edition. 2007; 18(3):241-68.

Wang W, Li B, Li Y, Jiang Y, Ouyang H, Gao C. In vivo restoration of full-thickness cartilage defects by poly (lactide-co-glycolide) sponges filled with fibrin gel, bone marrow mesenchymal stem cells and DNA complexes. Biomaterials. 2010 August; 31(23):5953-65.

Leddy H A, Awad H A, Guilak F. Molecular diffusion in tissue-engineered cartilage constructs: Effects of scaffold material, time, and culture conditions. Journal of Biomedical Materials Research Part B: Applied Biomaterials. 2004; 70B(2):397-406.

Greene G W, Zappone B, Zhao B, Soderman O, Topgaard D, Rata G, et al. Changes in pore morphology and fluid transport in compressed articular cartilage and the implications for joint lubrication. Biomaterials. 2008 November; 29(33):4455-62.

Torzilli P A, Arduino J M, Gregory J D, Bansal M. Effect of proteoglycan removal on solute mobility in articular cartilage. J Biomech. 1997 September; 30(9):895-902.

Torzilli P A, Grande D A, Arduino J M. Diffusive properties of immature articular cartilage. Journal of Biomedical Materials Research. 1998; 40(1):132-8.

Byun S, Tortorella M D, Malfait A-M, Fok K, Frank E H, Grodzinsky A J. Transport and Equilibrium Uptake of a Peptide Inhibitor of PACE4 into Articular Cartilage is Dominated by Electrostatic Interactions. Arch Biochem Biophys. 2010 July; 499(1-2):32-9.

Grodzinsky A J. Fields, forces, and flows in biological systems. New York: Garland Science; 2011.

Dougherty S A, Zhang D, Liang J. Fabrication of Protein Nanotubes Using Template-Assisted Electrostatic Layer-by-Layer Methods. Langmuir. 2009 Nov. 17; 25(22): 13232-7.

Moeini M, Quinn T M. Solute adsorption to surfaces of articular cartilage explants: apparent versus actual partition coefficients. Soft Matter. 2012 Nov. 14; 8(47): 11880-8.

Larsen, C. et al. Intra-articular depot formulation principles: role in the management of postoperative pain and arthritic disorders. *J. Pharm. Sci.* 97, 4622-4654 (2008).

Evans, C. H., Kraus, V. B. & Setton, L. A. Progress in intra-articular therapy. *Nat. Rev.*

Day, R. O., McLachlan, A. J., Graham, G. G. & Williams, K. M. Pharmacokinetics of nonsteroidal anti-inflammatory drugs in synovial fluid. *Clin. Pharmacokinet.* 36, 191-210 (1999).

Owen, S. G., Francis, H. W. & Roberts, M. S. Disappearance kinetics of solutes from synovial fluid after intra-articular injection. *Br. J. Clin. Pharmacol.* 38, 349-355 (1994).

Kamisan, N., Naveen, S. V., Ahmad, R. E. & Tunku, K. Chondrocyte density, proteoglycan content and gene expressions from native cartilage are species specific and not dependent on cartilage thickness: a comparative analysis between rat, rabbit and goat. *BMC Vet. Res.* 9, 62 (2013).

Malda, J. et al. Of mice, men and elephants: the relation between articular cartilage thickness and body mass. *PloS One* 8, e57683 (2013).

Moyer, J. T., Priest, R., Bouman, T., Abraham, A. C. & Donahue, T. L. H. Indentation properties and glycosaminoglycan content of human menisci in the deep zone. *Acta Biomater.* 9, 6624-6629 (2013).

Amiel, D., Frank, C., Harwood, F., Fronek, J. & Akeson, W. Tendons and ligaments: a morphological and biochemical comparison. *J. Orthop. Res. Off. Publ. Orthop. Res. Soc.* 1, 257-265 (1984).

Rumian, A. P., Wallace, A. L. & Birch, H. L. Tendons and ligaments are anatomically distinct but overlap in molecular and morphological features—a comparative study in an ovine model. *J. Orthop. Res. Off. Publ. Orthop. Res. Soc.* 25, 458-464 (2007).

Tischer, T., Milz, S., Maier, M., Schieker, M. & Benjamin, M. An immunohistochemical study of the rabbit suprapatella, a sesamoid fibrocartilage in the quadriceps tendon containing aggrecan. *J. Histochem. Cytochem. Off. J. Histochem. Soc.* 50, 955-960 (2002).

Ralphs, J. R., Benjamin, M. & Thornett, A. Cell and matrix biology of the suprapatella in the rat: A structural and immunocytochemical study of fibrocartilage in a tendon subject to compression. *Anat. Rec.* 231, 167-177 (1991).

Fraser, J. R., Kimpton, W. G., Pierscionek, B. K. & Cahill, R. N. The kinetics of hyaluronan in normal and acutely inflamed synovial joints: observations with experimental arthritis in sheep. *Semin. Arthritis Rheum.* 22, 9-17 (1993).

Ellison, D., Hinton, J., Hubbard, S. J. & Beynon, R. J. Limited proteolysis of native proteins: the interaction between avidin and proteinase K. *Protein Sci. Publ. Protein Soc.* 4, 1337-1345 (1995).

We claim:

1. A composition comprising:
a nanoparticle having an average particle size of 10 nm or less, wherein the nanoparticle includes an active agent, wherein the active agent is a therapeutic agent for the treatment of a disease condition of a bone or a connective tissue, and wherein the nanoparticle comprises a polymer having a net positive charge of 6-20, wherein the polymer is a peptide selected from the group consisting of multimeric avidin, lysozyme and amphiphilic triblock peptides.

2. The composition of claim 1, wherein the polymer has a molecular weight of less than 90 kd.

3. The composition of claim 1, wherein the polymer has a molecular weight of 10 kd-90 kd.

4. The composition of claim 1, wherein the therapeutic agent is insulin-like growth factor (IGF).

5. The composition of claim 1, wherein the polymer has a molecular weight of 60-90 kd.

6. The composition of claim 1, wherein the polymer has a molecular weight of 60-90 kd.

7. The composition of claim 1, wherein the polymer has a molecular weight of 60-90 kd.

8. The composition of claim 1, wherein the nanoparticle comprises a polymer having a net positive charge of 714.

* * * * *

UNITED STATES PATENT AND TRADEMARK OFFICE
CERTIFICATE OF CORRECTION

PATENT NO. : 10,226,427 B2
APPLICATION NO. : 15/071709
DATED : March 12, 2019
INVENTOR(S) : Ambika Goel Bajpayee et al.

Page 1 of 1

It is certified that error appears in the above-identified patent and that said Letters Patent is hereby corrected as shown below:

In the Claims

At Column 50, Line 22, Claim 8:
"comprises a polymer having a net positive charge of 714."
Should read:
—comprises a polymer having a net positive charge of 7-14.—

Signed and Sealed this
Eighteenth Day of February, 2020

Andrei Iancu
*Director of the United States Patent and Trademark Office*